US009040059B2

(12) United States Patent
Curtiss, III et al.

(10) Patent No.: US 9,040,059 B2
(45) Date of Patent: May 26, 2015

(54) RECOMBINANT BACTERIUM CAPABLE OF ELICITING A PROTECTIVE IMMUNE RESPONSE AGAINST C. PERFRINGENS

(75) Inventors: Roy Curtiss, III, Paradise Valley, AZ (US); Bereket Zekarias, Mesa, AZ (US); Kenneth Roland, Mesa, AZ (US)

(73) Assignee: The Arizona Board of Regents for and on Behalf of Arizona State University, Tempe, AZ (US)

( * ) Notice: Subject to any disclaimer, the term of this patent is extended or adjusted under 35 U.S.C. 154(b) by 183 days.

(21) Appl. No.: 12/681,711

(22) PCT Filed: Oct. 6, 2008

(86) PCT No.: PCT/US2008/078993
§ 371 (c)(1),
(2), (4) Date: Apr. 1, 2011

(87) PCT Pub. No.: WO2009/046451
PCT Pub. Date: Apr. 9, 2009

(65) Prior Publication Data
US 2011/0256181 A1 Oct. 20, 2011

Related U.S. Application Data

(60) Provisional application No. 60/978,084, filed on Oct. 5, 2007.

(51) Int. Cl.
*A61K 39/112* (2006.01)
*A61K 39/02* (2006.01)
*A01N 63/00* (2006.01)
*A61K 39/00* (2006.01)
*C12N 15/74* (2006.01)

(52) U.S. Cl.
CPC ........... *A61K 39/0275* (2013.01); *A61K 39/025* (2013.01); *C12N 15/74* (2013.01); *A61K 2039/522* (2013.01); *A61K 2039/523* (2013.01)

(58) Field of Classification Search
None
See application file for complete search history.

(56) References Cited

U.S. PATENT DOCUMENTS

| | | |
|---|---|---|
| 4,190,495 A | 2/1980 | Curtiss, III |
| 4,888,170 A | 12/1989 | Curtiss, III |
| 4,968,619 A | 11/1990 | Curtiss, III |
| 5,210,035 A | 5/1993 | Stocker |
| 5,294,441 A | 3/1994 | Curtiss, III |
| 5,387,744 A | 2/1995 | Curtiss |
| 5,389,368 A | 2/1995 | Gurtiss, III |
| 5,424,065 A | 6/1995 | Curtiss, III |
| 5,468,485 A | 11/1995 | Curtiss, III |
| 5,536,658 A | 7/1996 | Shotts, Jr. et al. |
| 5,654,184 A | 8/1997 | Curtiss, III |
| 5,656,488 A | 8/1997 | Curtiss, III |
| 5,672,345 A | 9/1997 | Curtiss, III |
| 5,679,880 A | 10/1997 | Curtiss, III |
| 5,686,079 A | 11/1997 | Curtiss, III |
| 5,817,317 A | 10/1998 | Titball |
| 5,827,705 A | 10/1998 | Dean |
| 5,840,483 A | 11/1998 | Curtiss, III |
| 5,855,879 A | 1/1999 | Curtiss, III |
| 5,855,880 A | 1/1999 | Curtiss, III |
| 5,961,983 A | 10/1999 | Brey et al. |
| 6,024,961 A | 2/2000 | Curtiss, III |
| 6,180,614 B1 | 1/2001 | Davis |
| 6,248,329 B1 | 6/2001 | Chandrashekar et al. |
| 6,350,454 B1 | 2/2002 | Thune |
| 6,383,496 B1 | 5/2002 | Curtiss, III |
| 6,399,074 B1 | 6/2002 | Roland |
| 6,403,094 B1 | 6/2002 | Titball |
| 6,610,529 B1 | 8/2003 | Curtiss, III |
| 6,780,405 B1 | 8/2004 | Curtiss, III |
| 6,872,547 B1 | 3/2005 | Curtiss, III |
| 6,969,513 B2 | 11/2005 | Galen |
| 7,083,794 B2 | 8/2006 | Curtiss, III |
| 7,195,757 B2 | 3/2007 | Curtiss, III |
| 7,205,125 B2 | 4/2007 | Castillo |
| 7,341,860 B2 | 3/2008 | Curtiss, III |
| 7,871,604 B1 | 1/2011 | Curtiss, III |
| 7,968,101 B2 | 6/2011 | Kawaoka |
| 8,133,493 B2 | 3/2012 | Curtiss, III |
| 8,445,254 B2 | 5/2013 | Curtiss, III et al. |
| 8,465,755 B2 | 6/2013 | Curtiss, III et al. |
| 2003/0031683 A1 | 2/2003 | Curtiss, III |
| 2003/0175772 A1 | 9/2003 | Wang |
| 2004/0077556 A1 | 4/2004 | Chinery |
| 2004/0101531 A1 | 5/2004 | Curtiss |
| 2004/0120962 A1 | 6/2004 | Curtiss, III |
| 2004/0137003 A1 | 7/2004 | Curtiss, III |
| 2004/0203039 A1 | 10/2004 | Hensel |
| 2005/0036987 A1 | 2/2005 | Pawelek |

(Continued)

FOREIGN PATENT DOCUMENTS

| | | |
|---|---|---|
| EP | 0315682 B1 | 12/1993 |
| EP | 0381706 B1 | 4/1995 |

(Continued)

OTHER PUBLICATIONS

Stevens et al. J. Infect. Dis. 190:767-773, 2004.*
WO 2009/046451 International Search Report mailed Dec. 15, 2008. 1 page.
Hess et al., Secretion of different listeriolysin cognates by recombinant attenuated *Salmonella typhimurium*: superior efficacy of haemolytic over non-haemolytic constructs after oral vaccination. Microbes Infect, 2000, pp. 1799-1806, vol. 2.
Hohmann et al., Evaluation of a phoP/phoQ-deleted, aroA-deleted live oral *Salmonella typhi* vaccine strain in human volunteers. Vaccine, 1996, pp. 19-24, vol. 14.

(Continued)

Primary Examiner — S. Devi
(74) Attorney, Agent, or Firm — Polsinelli PC

(57) ABSTRACT

The present invention encompasses recombinant bacteria and immunogenic compositions comprising the bacteria. The immunogenic composition may be used to induce an immune response against *C. perfringens*.

9 Claims, 29 Drawing Sheets

(56) References Cited

U.S. PATENT DOCUMENTS

| | | | |
|---|---|---|---|
| 2005/0106175 | A1 | 5/2005 | Montanes |
| 2005/0106176 | A1 | 5/2005 | Curtiss, III |
| 2005/0118193 | A1 | 6/2005 | Andino-Pavlovsky et al. |
| 2006/0140975 | A1 | 6/2006 | Curtiss, III |
| 2006/0171917 | A1 | 8/2006 | Campbell |
| 2006/0206961 | A1 | 9/2006 | Cirpus |
| 2006/0233829 | A1 | 10/2006 | Curtiss, II |
| 2006/0234346 | A1 | 10/2006 | Retallack |
| 2006/0275255 | A1 | 12/2006 | Gudkov |
| 2007/0025981 | A1 | 2/2007 | Szalay |
| 2008/0096809 | A1 | 4/2008 | Shai |
| 2008/0248066 | A1 | 10/2008 | Dubensky, Jr. |
| 2009/0175829 | A1 | 7/2009 | Forbes |
| 2010/0124558 | A1 | 5/2010 | Curtiss, III |
| 2010/0154293 | A1 | 6/2010 | Hom et al. |
| 2010/0255022 | A1* | 10/2010 | Prescott et al. ........... 424/190.1 |
| 2010/0285592 | A1 | 11/2010 | Curtiss, III |
| 2010/0317084 | A1 | 12/2010 | Curtiss, III |
| 2011/0033501 | A1 | 2/2011 | Curtiss, III et al. |
| 2011/0256181 | A1 | 10/2011 | Curtiss, III |
| 2011/0287052 | A1 | 11/2011 | Curtiss, III et al. |
| 2012/0087946 | A1 | 4/2012 | Curtiss, III |
| 2013/0004537 | A1 | 1/2013 | Curtiss, III et al. |
| 2013/0171190 | A1 | 7/2013 | Curtiss, III et al. |

FOREIGN PATENT DOCUMENTS

| | | | |
|---|---|---|---|
| EP | 0465560 | B1 | 6/1996 |
| EP | 0500699 | B1 | 6/1998 |
| EP | 0558631 | B1 | 3/1999 |
| EP | 0433372 | B1 | 6/2002 |
| EP | 1030690 | B1 | 7/2002 |
| EP | 0556333 | B1 | 3/2003 |
| EP | 1326960 | B1 | 12/2004 |
| EP | 0832255 | B1 | 12/2005 |
| EP | 1537214 | B1 | 3/2006 |
| EP | 1292687 | B1 | 8/2006 |
| WO | 88/09669 | A1 | 12/1988 |
| WO | 89/03427 | A1 | 4/1989 |
| WO | 90/02484 | A1 | 3/1990 |
| WO | 90/11687 | A1 | 10/1990 |
| WO | 90/11688 | A1 | 10/1990 |
| WO | 90/12086 | A1 | 10/1990 |
| WO | 91/06317 | A1 | 5/1991 |
| WO | 92/08486 | A1 | 5/1992 |
| WO | 92/09684 | A1 | 6/1992 |
| WO | 93/04202 | A1 | 3/1993 |
| WO | 94/24291 | A2 | 10/1994 |
| WO | 94/24291 | A3 | 12/1994 |
| WO | 96/40947 | A1 | 12/1996 |
| WO | 99/25387 | A1 | 5/1999 |
| WO | 01/83785 | A2 | 11/2001 |
| WO | 02/30457 | A2 | 4/2002 |
| WO | 01/83785 | A3 | 6/2002 |
| WO | 02/059292 | A2 | 8/2002 |
| WO | 02/30457 | A3 | 1/2003 |
| WO | 02/30457 | A3 | 7/2003 |
| WO | 02/059292 | A3 | 7/2003 |
| WO | 03/079792 | A1 | 10/2003 |
| WO | 03/096812 | A1 | 11/2003 |
| WO | 2004/020643 | A2 | 3/2004 |
| WO | 2004/020643 | A3 | 4/2004 |
| WO | 2005/001069 | A1 | 1/2005 |
| WO | 2008/141226 | A2 | 11/2008 |
| WO | 2009/025888 | A2 | 2/2009 |
| WO | 2009/046449 | A1 | 4/2009 |
| WO | 2009/046451 | A1 | 4/2009 |
| WO | WO 2009/046451 | | 4/2009 |
| WO | 2010/045620 | A1 | 4/2010 |
| WO | 2010/078584 | A1 | 8/2010 |
| WO | 2010/135563 | A1 | 11/2010 |
| WO | 2011/091291 | A1 | 7/2011 |
| WO | 2011/150421 | A2 | 12/2011 |
| WO | 2012087483 | A1 | 6/2012 |

OTHER PUBLICATIONS

Hu et al., The inducible lac operator-repressor system is functional in mammalian cells. Cell, 1987, pp. 555-566, vol. 48, No. 4.
Hu et al., The inducible lac operator-repressor system is functional for control of expression of injected DNA in *Xenopus* oocytes. Gene, 1988, pp. 301-313, vol. 62, No. 2.
Huang et al., Genome-wide screen of *Salmonella* nucleic acid sequences expressed during infection in pigs, using in vivo expression technology. Appl Environ Microbiol, 2007, pp. 7522-7530, vol. 73, No. 23.
Iannelli et al., Allelic variation in the highly polymorphic locus pspC of *Streptococcus pneumoniae*. Gene, 2002, pp. 63-71, vol. 284.
In Soo Lee et al., The stationary-phase sigma factor sS (RpoS) is required for a sustained acid tolerance response in virulent *Salmonella typhimurium*. Molecular Microbiology, 1995, pp. 155-167, vol. 17.
Isoda et al., Expression of a *Porphyromonas gingivalis* hemagglutinin on the surface of a *Salmonella* vaccine vector. Vaccine, 2007, pp. 117-126, vol. 25, No. 1.
Ivancic-Bace et al, Effects of recJ, recQ, and recFOR mutations on recombination in nuclease-deficient recB recD double mutants of *Escherichia coli*. J. Bacteriol., 2005, pp. 1350-1356, vol. 187.
Kaufmann et al., Impact of intracellular location of and antigen display by intracellular bacteria: implications for vaccine development. Immunol. Lett., 1999, pp. 81-84, vol. 65.
Khan et al., Immunogenicity and protective efficacy of DnaJ (hsp40) of *Streptococcus pneumoniae* against lethal infection in mice. Vaccine, 2006, pp. 6225-6231, vol. 24.
Kim et al., Direct transcriptional control of the plasminogen activator gene of *Yersinia pestis* by the cyclic AMP receptor protein. J Bacteriol, 2007, pp. 8890-8900, vol. 189.
Kolodrubetz et al., Regulation of the L-arabinose transport operons in *Escherichia coli*. J Mol Biol, 1981, pp. 215-227, vol. 151, No. 2.
Kwon et al., *Salmonella*-based vaccines for infectious diseases. Expert Review of Vaccines, 2007, pp. 147-152, vol. 6.
Lange et al., Identification of a central regulator of stationary-phase gene expression in *Escherichia coli*. Mol Microbiol, 1991, pp. 49-59, vol. 5.
Lee et al., Regulation of L-arabinose transport in *Salmonella typhimurium* LT2. Mol Gen Genet, 1982, pp. 136-141, vol. 185, No. 1.
Lee et al., Surface-displayed viral antigens on *Salmonella* carrier vaccine. Nat Biotechnol, 2000, pp. 645-648, vol. 18, No. 6.
Lewis, The lac repressor. C R Biol, 2005, pp. 521-548, vol. 328, No. 6.
Lobell et al., AraC-DNA looping: orientation and distance-dependent loop breaking by the cyclic AMP receptor protein. J Mol Biol, 1991, pp. 45-54, vol. 218.
Lobocka et al., Organization and expression of the *Escherichia coli* K-12 dad operon encoding the smaller subunit of D-amino acid dehydrogenase and the catabolic alanine racemase. J. Bacteriol., 1994, pp. 1500-1510, vol. 176.
Loessner et al., Bacteria-mediated DNA transfer in gene therapy and vaccination. Expert. Opin. Biol. Ther., 2004, pp. 157-168, vol. 4.
Loessner et al., Remote control of tumour-targeted *Salmonella enterica* serovar *typhimurium* by the use of L-arabinose as inducer of bacterial gene expression in vivo. Cell Microbiol, 2007, pp. 1529-1537, vol. 9.
Marshall et al., Use of the stationary phase inducible promoters, spy and dps, to drive heterologous antigen expression in *Salmonella* vaccine strains. Vaccine, 2000, pp. 1298-1306, vol. 18, No. 14.
Medina et al., Use of live bacterial vaccine vectors for antigen delivery: potential and limitations. Vaccine, 2001, pp. 1573-1580, vol. 19.
Mehigh et al., Expression of the low calcium response in *Yersinia pestis*. Microb Pathog, 1989, pp. 203-217, vol. 6.
Moore et al., Enhanced protective immunity against pneumococcal infection with PspA DNA and protein. Vaccine, 2006, p. 5755, vol. 24.
Mossing et al., Upstream operators enhance repression of the lac promoter. Science, 1986, pp. 889-892, vol. 233, No. 4766.
Motin et al., Passive immunity to Yersiniae mediated by anti-recombinant V antigen and protein A-V antigen fusion peptide. Infect Immun, 1994, pp. 4192-4201, vol. 62.

(56) References Cited

OTHER PUBLICATIONS

Muller et al., Repression of lac promoter as a function of distance, phase and quality of an auxiliary lac operator. J Mol Biol, 1996, pp. 21-29, vol. 257, No. 1.
Muller-Hill et al., Mutants that mke more lac repressor. Proc Natl Acad Sci U S A, 1968, pp. 1259-1264, vol. 59, No. 4.
Muller-Hill, Lac repressor and lac operator. Prog Biophys Mol Biol, 1975, pp. 227-252, vol. 30, No. 2-3.
Nabors et al., Immunization of healthy adults with a single recombinant pneumococcal surface protein a (PspA) variant stimulates broadly cross-reactive antibodies to heterologous PspA molecules. Vaccine, 2000, p. 1743, vol. 18.
Nakayama et al., Construction of an Asd+ expression-cloning vector: stable maintenance and high level expression of cloned nucleic acid sequences in a *Salmonella* vaccine strain. BioTechnology, 1988, pp. 693-697, vol. 6.
Nedialkov et al., Resistance to lipopolysaccharide mediated by the *Yersinia pestis* V antigen-polyhistidine fusion peptide: amplification of interleukin-10. Infect Immun, 1997, pp. 1196-1203, vol. 65.
Neutra et al., Antigen sampling across epithelial barriers and induction of mucosal immune responses. Annu Rev Immunol, 1996, pp. 275-300, vol. 14.
O'Callaghan et al., High efficiency transformation of *Salmonella typhimurium* and *Salmonella typhi* by electroporation. Mol Gen Genet, 1990, pp. 156-158, vol. 223, No. 1.
Ortqvist et al., Randomised trial of 23-valent pneumococcal capsular polysaccharide vaccine in prevention of pneumonia in middle-aged and elderly people. Swedish Pneumococcal Vaccination Study Group. Lancet, 1998, pp. 399-403, vol. 351.
Perry et al., Temperature regulation of the hemin storage (Hms+) phenotype of *Yersinia pestis* is posttranscriptional. J Bacteriol, 2004, pp. 1638-1647, vol. 186.
Petersen et al., Essential role for cyclic AMP and its receptor protein in *Yersinia enterocolitica* virulence. Infect Immun, 2004, pp. 3665-3672, vol. 70.
Ramarathinam et al., *Salmonella typhimurium* induces IFN-gamma production in murine splenocytes. Role of natural killer cells and macrophages. J Immunol, 1993, pp. 3973-3981, vol. 150.
Raupach et al., Bacterial virulence, proinflammatory cytokines and host immunity: how to choose the appropriate *Salmonella* vaccine strain? Microbes and Infection, 2001, p. 1261, vol. 3.
Roland et al., Construction and evaluation of a delta cya delta crp *Salmonella typhimurium* strain expressing avian pathogenic *Escherichia coli* O78 LPS as a vaccine to prevent airsacculitis in chickens. Avian Dis, 1999, pp. 429-441, vol. 43, No. 3.
Sarubbi et al., (1989) Characterization of the spoT gene of *Escherichia coli*. J Biol Chem, 1989, pp. 15074-15082, vol. 264.
Schmieger et al., Altered cotransduction frequencies exhibited by HT-mutants of *Salmonella*-phage P22. Mol Gen Genet, 1976, pp. 307-309, vol. 143.
Schmieger, Phage P22-mutants with increased or decreased transduction abilities. Mol Gen Genet, 1972, pp. 75-88, vol. 119.
Schödel et al., Hybrid hepatitis B virus core antigen as a vaccine carrier moiety. II. Expression in avirulent *Salmonella* spp. for mucosal immunization. Adv Exp Med Biol., 1996, pp. 15-21, vol. 397.
Schodel, Prospects for oral vaccination using recombinant bacteria expressing viral epitopes. Adv. Virus Res., 1992, pp. 409-446, vol. 41.
Schwyn et al., Universal chemical assay for the detection and determination of siderophores. Analytical Biochemistry, 1987, p. 47, vol. 160.
Sedgwick et al., A solid-phase immunoenzymatic technique for the enumeration of specific antibody-secreting cells. Journal of Immunological Methods, 1983, p. 301, vol. 57.
Shalaby, Development of oral vaccines to stimulate mucosal and systemic immunity: barriers and novel strategies. Clin Immunol Immunopathol, 1995, pp. 127-134, vol. 74, No. 2.

Alonso et al, Anti-polysaccharide immunoglobulin isotype levels and opsonic activity of antisera: relationships with protection against *Streptococcus pneumoniae* infection in mice. J Infect Dis, 1995, pp. 562-565, vol. 172.
Amann et al., Tightly regulated tac promoter vectors useful for the expression of unfused and fused proteins in *Escherichia coli*. Nucleic acid sequence, 1988. pp. 301-315, vol. 69, No. 2.
Anderson et al., Delivery of the Pertactin/P.69 polypeptide of *Bordetella pertussis* using an attenuated *Salmonella typhimurium* vaccine strain: expression levels and immune response. Vaccine, 1996, pp. 1384-1390, vol. 14, No. 14.
Aravind et al., The HD domain defines a new superfamily of metal-dependent phosphohydrolases. Trends Biochem Sci, 1998, pp. 469-472, vol. 23.
Arricau et al., The RcsB-RcsC regulatory system of *Salmonella typhi* differentially modulates the expression of invasion proteins, flagellin and Vi antigen in response to osmolarity., Mol Microbiol, 1998, pp. 85-50, vol. 29, No. 3.
Arulanandam et al., Intranasal vaccination with pneumococcal surface protein A and interleukin-12 augments antibody-mediated opsonization and protective immunity against *Streptococcus pneumoniae* infection. Infect Immun, 2001, pp. 6718-6724, vol. 69.
Audia et al., Breaking through the acid barrier: an orchestrated response to proton stress by enteric bacteria. Int J Med Microbiol, 2001, pp. 97-106, vol. 291.
Battesti et al., Acyl carrier protein/SpoT interaction, the switch linking SpoT-dependent stress response to fatty acid metabolism. Mol Microbiol, 2006, pp. 1048-1063, vol. 62.
Blattner et al., The complete genome sequence of *Escherichia coli* K-12. Science, 1997, pp. 1453-1474, vol. 277.
Branger et al., Oral vaccination with different antigens from *Yersinia pestis* KIM delivered by live attenuated *Salmonella typhimurium* elicits a protective immune response against plague. Adv Exp Med Biol, 2007, pp. 387-399, vol. 603.
Briles et al. The potential for using protein vaccines to protect against otitis media caused by *Streptococcus pneumoniae*. Vaccine, 2001, pp. S87-S95, vol. 19, Suppl 1.
Brubaker, Interleukin-10 and inhibition of innate immunity to Yersiniae: roles of Yops and LcrV (V antigen). Infect Immun, 2003, pp. 3673-3681, vol. 71.
Brubaker, The Vwa+ virulence factor of Yersiniae: the molecular basis of the attendant nutritional requirement for Ca2+. Rev Infect Dis, 1983,pp. S748-S758, vol. 5, Suppl 4.
Brumell et al., (2004) *Salmonella* redirects phagosomal maturation. Curr Opin Microbiol, 2004, pp. 78-84, vol. 7.
Cárdenas et al., Oral immunization using live attenuated *Salmonella* spp. as carriers of foreign antigens. Clin. Microbiol. Rev., 1992, pp. 328-342, vol. 5, No. 3.
Charnetzky et al., RNA synthesis in *Yersinia pestis* during growth restriction in calcium-deficient medium. J Bacteriol, 1982, pp. 108-195, vol. 149.
Chatfield et al., Use of the nirB promoter to direct the stable expression of heterologous antigens in *Salmonella* oral vaccine strains: development of a single-dose oral tetanus vaccine. Biotechnology (N Y), 1992, pp. 888-892, vol. 10, No. 8.
Cheng et al., Simultaneous analyses of neutral carbohydrates and amino sugars in freshwaters with HPLC-PAD. J. Chromatogr. Sci., 2003, pp. 434-438, vol. 41.
Chipman et al., The ACT domain family. Curr Opin Struct Biol, 2001, pp. 694-700, vol. 11.
Chromy et al., Proteomic characterization of *Yersinia pestis* virulence. J Bacteriol, 2005, pp. 8172-8180, vol. 187.
Coombes et al., SseL is a *Salmonella*-Specific Translocated Effector Integrated into the SsrB-Controlled *Salmonella* Pathogenicity Island 2 Type III Secretion System. Infection and Immunity, 2007, pp. 574-580, vol. 75, No. 2.
Cornelis et al., The virulence plasmid of *Yersinia*, an antihost genome. Microbiol Mol Biol Rev, 1998, pp. 1315-1352, vol. 62.
Curtiss et al. Nonrecombinant and recombinant avirulent *Salmonella* vaccines for poultry. Vet Immunol Immunopathol, 1996, pp. 365-372, vol. 54.
Curtiss et al., Live oral avirulent *Salmonella* vaccines. Vet. Microbiol., 1993, pp. 397-405, vol. 37.

(56) References Cited

OTHER PUBLICATIONS

Curtiss et al., Recombinant *Salmonella* vectors in vaccine development. Dev Biol Stand., 1994, pp. 23-33, vol. 82.
Datsenko et al., One-step inactivation of chromosomal genes in *Escherichia coli* K-12 using PCR products. Proc Natl Acad Sci USA, 2000, pp. 6640-6645, vol. 97.
Davison, Towards safer vectors for the field release of recombinant bacteria. Environ. Biosafety Res., 2002, pp. 9-18, vol. 1.
De Groote et al., Homocysteine antagonism of nitric oxide-related cytostasis in *Salmonella typhimurium*. Science, 1996, pp. 414-417, vol. 272.
Dekruyff et al., Induction of immunoglobulin synthesis by CD4+ T cell clones. Seminars in Immunology, 1993, pp. 421-430, vol. 5.
Del Beccaro et al., Bacteriology of acute otitis media: a new perspective. J Pediatr, 1992, pp. 81-84, vol. 120.
Deng et al., Genome sequence of *Yersinia pestis* KIM. J Bacteriol, 2002, pp. 4601-4611, vol. 184.
Doggett et al., Delivery of antigens by recombinant avirulent *Salmonella* strains. Adv. Exp. Med. Biol., 1992, pp. 165-173, vol. 327.
Doublet et al., the murI gene of *Escherichia coli* is an essential gene that encodes a glutamate racemase activity. J. Bacteriol., 1993, pp. 2970-2979, vol. 175.
Dubnau, DNA uptake in bacteria. Annu. Rev. Microbiol., 1999, pp. 217-244, vol. 53.
Edwards et al., Improved allelic exchange vectors and their use to analyze 987P fimbria nucleic acid sequence expression. Gene, 1998, pp. 149-157, vol. 207, No. 2.
Fooks, Development of oral vaccines for human use. Curr Opin Mol Ther, 2000, pp. 80-86, vol. 2, No. 1.
Foster et al., How *Salmonella* survive against the odds. Annu Rev Microbiol, 1995, pp. 145-174, vol. 49.
Galen et al., Can a 'flawless' live vector vaccine strain be engineered? Trends Microbiol, 2001, pp. 372-376, vol. 9, No. 8.
Garmory et al., The Use of Live Attenuated Bacteria as a Delivery System for Heterologous Antigens. Journal of Drug Targeting, 2003, pp. 471, vol. 11.
Garzon et al., recB recJ mutants of *Salmonella typhimurium* are deficient in transductional recombination, DNA repair and plasmid maintenance. Mol. Gen. Genet., 1996, pp. 570-580, vol. 250.
Gentry et al., Mutational analysis of the *Escherichia coli* spoT gene identifies distinct but overlapping regions involved in ppGpp synthesis and degradation. Mol Microbiol, 1996, pp. 1373-1384, vol. 19.
Gentschev et al., The *E. coli* alpha-hemolysin secretion system and its use in vaccine development. Trends Microbiol, 2002, pp. 39-45, vol. 10, No. 1.
Giannella et al., Gastric acidity and cholera. Ann Intern Med, 1973, p. 780, vol. 78.
Gilbert, The lac repressor and the lac operator. Ciba Found Symp, 1972, pp. 24-59, vol. 7.
Gong et al., Characterization of the *Yersinia pestis* Yfu ABC inorganic iron transport system. Infect Immun, 2001, pp. 2829-2837, vol. 69.
Gor et al., TH1-TH2: a Procrustean paradigm. Nat Immunol, 2003, p. 503-505, vol. 4.
Grillot-Courvalin et al., Functional gene transfer from intracellular bacteria to mammalian cells. Nat. Biotechnol., 1998, pp. 862-866, vol. 16.
Guerrant et al., Magnitude and Impact of Diarrheal Diseases. Arch. Med. Res., 2002, pp. 351-355, vol. 33.
Gunn, Mechanisms of bacterial resistance and response to bile. Microbes Infect, 2000, pp. 907-913, vol. 2.
Hengge-Aronis et al., Identification and molecular analysis of glgS, a novel growth-phase-regulated and rpoS-dependent gene involved in glycogen synthesis in *Escherichia coli*. Mol Microbiol, 1992, pp. 1877-1886, vol. 6.
PCT/US2008/063303 (WO 2008/141226)—International Search Report and Written Opinion of the International Searching Authority, Nov. 26, 2008.
PCT/US2008/063293 (WO 2009/025888)—International Search Report and Written Opinion of the International Searching Authority, Feb. 12, 2009.
PCT/US2008/078991 (WO 2009/046449)—International Search Report and Written Opinion of the International Searching Authority, Dec. 15, 2008.
PCT/US2008/078993 (WO 2009/046451)—International Search Report and Written Opinion of the International Searching Authority, Dec. 15, 2008.
PCT/US2010/035630 (WO 2010/135563)—International Search Report and Written Opinion of the International Searching Authority, Sep. 29, 2010.
PCT/US2009/061100 (WO 2010/045620)—International Search Report and Written Opinion of the International Searching Authority, Dec. 4, 2009.
PCT/US2010/020137 (WO 2010/078584)—International Search Report and Written Opinion of the International Searching Authority, Mar. 9, 2010.
PCT/US2011/022110 (WO 2011/091291)—International Search Report and Written Opinion of the International Searching Authority, Apr. 11, 2011.
PCT/US2011/038588 (WO 2011/150421)—International Search Report and Written Opinion of the International Searching Authority, Nov. 22, 2011.
PCT/US98/24295—International Preliminary Examination Report, Dec. 26, 2000.
PCT/US2001/013915—International Preliminary Examination Report, Aug. 16, 2002.
European Patent Application No. 89910552.2 (EP0433372), Intention to Grant dated Jun. 19, 2001.
European Patent Application No. 89910552.2 (EP0433372), Office Action dated Oct. 10, 1994.
European Patent Application No. 89910552.2 (EP0433372), Office Action dated Sep. 12, 1995.
European Patent Application No. 89910552.2 (EP0433372), Office Action dated Jun. 20, 2000.
European Patent Application No. 89910552.2 (EP0433372), Decision to Grant dated May 6, 2002.
European Patent Application No. 90905859.6 (EP0465560), Office Action dated Feb. 19, 1992.
European Patent Application No. 90905859.6 (EP0465560), Office Action dated Feb. 9, 1994.
European Patent Application No. 90905859.6 (EP0465560), Intention to Grant dated Jan. 4, 1995.
European Patent Application No. 90905859.6 (EP0465560), Decision to Grant dated Apr. 25, 1996.
European Patent Application No. 96919292.1 (EP0832255), Office Action dated Sep. 30, 2003.
European Patent Application No. 96919292.1 (EP0832255), Office Action dated Jul. 13, 2004.
European Patent Application No. 96919292.1 (EP0832255), Intention to Grant dated May 25, 2005.
European Patent Application No. 96919292.1 (EP0832255), Decision to Grant dated Nov. 4, 2005.
European Patent Application No. 98958581.5 (EP1030690), Office Action dated Jan. 31, 2001.
European Patent Application No. 98958581.5 (EP1030690), Intention to Grant dated Sep. 7, 2001.
European Patent Application No. 98958581.5 (EP1030690), Decision to Grant dated May 24, 2002.
European Patent Application No. 01944119.5 (EP1292687), Office Action dated Oct. 18, 2004.
European Patent Application No. 01944119.5 (EP1292687), Office Action dated Aug. 4, 2005.
European Patent Application No. 01944119.5 (EP1292687), Intention to Grant dated Jan. 26, 2006.
European Patent Application No. 01944119.5 (EP1292687), Decision to Grant dated Jul. 20, 2006.
European Patent Application No. 01979646.5 (EP1326960), Intention to Grant dated Apr. 8, 2004.
European Patent Application No. 01979646.5 (EP1326960), Decision to Grant dated Oct. 28, 2004.

(56) References Cited

OTHER PUBLICATIONS

European Patent Application No. 03721711.4 (EP1499191), Search Report dated May 23, 2006.
European Patent Application No. 03721711.4 (EP1499191), Office Action dated Aug. 24, 2006.
European Patent Application No. 03721711.4 (EP1499191), Office action dated Jan. 17, 2007.
European Patent Application No. 03721711.4 (EP1499191), Office action dated Mar. 23, 2009.
European Patent Application No. 03721711.4 (EP1499191), Office action dated Jun. 15, 2010.
European Patent Application No. 03721711.4 (EP1499191), Intention to Grant dated Oct. 21, 2011.
European Patent Application No. 03770256.0 (EP1537214), Intention to Grant dated Aug. 12, 2005.
U.S. Appl. No. 08/473,789, Office Action dated Apr. 15, 1997.
U.S. Appl. No. 08/473,789, Office Action dated Dec. 23, 1997.
U.S. Appl. No. 08/473,789, Office Action dated Nov. 13, 1998.
U.S. Appl. No. 08/473,789, Office Action dated Jun. 14, 1999.
U.S. Appl. No. 08/473,789, Office Action dated Jan. 21, 2000.
U.S. Appl. No. 08/473,789, Office Action dated Jul. 25, 2000.
U.S. Appl. No. 08/473,789, Office Action dated Sep. 27, 2001.
U.S. Appl. No. 08/761,769, Office Action dated Jul. 20, 1998.
U.S. Appl. No. 08/761,769, Office Action dated Mar. 3, 1999.
U.S. Appl. No. 08/761,769, Office Action dated Aug. 9, 2000.
U.S. Appl. No. 08/761,769, Office Action dated Sep. 25, 2001.
U.S. Appl. No. 08/761,769, Office Action dated Aug. 8, 2002.
U.S. Appl. No. 08/761,769, Notice of Allowance and Fees Due dated Jan. 22, 2003.
U.S. Appl. No. 09/120,970, Office Action dated Sep. 6, 2000.
U.S. Appl. No. 09/120,970, Office Action dated Jun. 5, 2001.
U.S. Appl. No. 09/120,970, Office Action dated Jan. 12, 2005.
U.S. Appl. No. 09/120,970, Office Action dated Nov. 8, 2005.
U.S. Appl. No. 09/120,970, Notice of Allowance and Fees Due dated Aug. 6, 2010.
U.S. Appl. No. 09/560,539, Office Action dated Feb. 12, 2002.
U.S. Appl. No. 09/560,539, Office Action dated Mar. 25, 2003.
U.S. Appl. No. 09/560,539, Office Action dated Aug. 29, 2003.
U.S. Appl. No. 09/560,539, Notice of Allowance and Fees Due dated Mar. 30, 2004.
U.S. Appl. No. 09/686,499, Office Action dated Jun. 20, 2001.
U.S. Appl. No. 09/686,499, Office Action dated Jan. 29, 2002.
U.S. Appl. No. 09/686,499, Office Action dated Dec. 16, 2002.
U.S. Appl. No. 09/686,499, Office Action dated Aug. 27, 2003.
U.S. Appl. No. 09/686,499, Notice of Allowance and Fees Due dated Nov. 2, 2004.
U.S. Appl. No. 10/138,239, Office Action dated Mar. 15, 2005.
U.S. Appl. No. 10/138,239, Office Action dated Sep. 21, 2005.
U.S. Appl. No. 10/138,239, Notice of Allowance and Fees Due dated Mar. 16, 2006.
U.S. Appl. No. 10/414,533, Office Action dated Apr. 12, 2006.
U.S. Appl. No. 10/414,533, Notice of Allowance and Fees Due dated Dec. 8, 2006.
U.S. Appl. No. 10/511,616, Office Action dated Nov. 27, 2009.
U.S. Appl. No. 10/511,616, Office Action dated Jun. 23, 2010.
U.S. Appl. No. 10/511,616, Office Action dated Dec. 27, 2010.
U.S. Appl. No. 10/511,616, Notice of Allowance and Fees Due dated Oct. 26, 2011.
U.S. Appl. No. 10/620,777, Office Action dated Nov. 14, 2006.
U.S. Appl. No. 10/620,777, Office Action dated Oct. 31, 2007.
U.S. Appl. No. 10/924,574, Office Action dated Feb. 28, 2007.
U.S. Appl. No. 10/924,574, Notice of Allowance and Fees Due dated Oct. 1, 2007.
European Patent Application No. 08827622.5, Search Report dated Jun. 27, 2011.
European Patent Application No. 08827622.5, Office action dated Feb. 22, 2012.
U.S. Appl. No. 12/615,872, Office Action dated Mar. 14, 2012.
U.S. Appl. No. 12/759,842, Office Action dated Oct. 4, 2011.
U.S. Appl. No. 12/789,869, Office Action dated Mar. 22, 2011.

U.S. Appl. No. 12/789,869, Office Action dated Dec. 7, 2011
Bang et al, OmpR regulates the stationary-phase acid tolerance response of *Salmonella enterica* serovar *typhimurium*. J Bacteriol, 2000, pp. 2245-2252, vol. 182.
Bang et al., Autoinduction of the ompR response regulator by acid shock and control of the *Salmonella enterica* acid tolerance response. Mol Microbiol, 2002, pp. 1235-1250, vol. 44.
Bartlett et al., Influenza A (H5N1): will it be the next pandemic influenza? Are we ready? Ann. Intern. Med., 2005, pp. 460-462, vol. 143.
Bartlett, Planning for avian influenza. Ann. Intern. Med., 2006, pp. 141-144, vol. 145.
Bearson et al., A low pH-inducible, PhoPQ-dependent acid tolerance response protects *Salmonella typhimurium* against inorganic acid stress. J Bacteriol, 1998, pp. 2409-2417, vol. 180.
Bertani, Studies on lysonucleic acid sequencesis. I. The mode of phage liberation by lysogenic *Escherichia coli*. J Bacteriol, 1951, pp. 293-300, vol. 62, No. 3.
Black et al., Aspartic •-semialdehydedehydrogenase and aspartic •-semialdehyde J. Biol. Chem., 1955, pp. 39-50, vol. 213.
Briles et al., Immunization of humans with recombinant pneumococcal surface protein A (rPspA) elicits antibodies that passively protect mice from fatal infection with *Streptococcus pneumoniae* bearing heterologous PspA. J. Infect. Dis., 2000, pp. 1694-1701, vol. 182.
Brooks-Walter et al., The pspC gene of *Streptococcus pneumoniae* encodes a polymorphic protein, PspC, which elicits cross-reactive antibodies to PspA and provides immunity to pneumococcal bacteremia. Infect. Immun., 1999, pp. 6533-6542, vol. 67.
Brosius et al., Spacing of the -10 and -35 regions in the tac promoter. Effect on its in vivo activity. J Biol Chem, 1985, pp. 3539-3540, vol. 260, No. 6.
Brown et al., MurA (MurZ), the enzyme that catalyzes the first committed step in peptidoglycan biosynthesis, is essential in *Escherichia coli*. J. Bacteriol., 1995, pp. 4194-4197, vol. 177.
Buchanan et al., IL-12 Enhances Antibody Responses to T-Independent Polysaccharide Vaccines in the Absence of T and NK Cells. J Immunol, 1998, pp. 5525-5533, vol. 161.
Buchmeier, et al., DNA repair is more important than catalase for *Salmonella* virulence in mice. J. Clin. Invest., 1995, pp. 1047-1053, vol. 95.
Bumann, Regulated antigen expression in live recombinant *Salmonella enterica* serovar *typhimurium* strongly affects colonization capabilities and specific CD4(+)-T-cell responses. Infect Immun, 2001. pp. 7493-7500, vol. 69, No. 12.
CDC, Update: influenza activity—United States, Sep. 30, 2007—Apr. 5, 2008, and composition of the 2008-09 influenza vaccine. MMWR Morb. Mortal. Wkly Rep., 2008, pp. 404-409, vol. 57.
Chen et al., Genetic mapping of the cold-adapted phenotype of B/Ann Arbor/1/66, the master donor virus for live attenuated influenza vaccines (FluMist). Virology, 2006, pp. 416-423, vol. 345.
Collins et al., Mutations at rfc or pmi attenuate *Salmonella typhimurium* virulence for mice. Infect. Immun., 1991, pp. 1079-1085, vol. 59.
Curtiss et al., Avirulent *Salmonella typhimurium* delta cya delta crp oral vaccine strains expressing a streptococcal colonization and virulence antigen. Vaccine, 1988, pp. 155-160, vol. 6.
Curtiss et al., New technologies in using recombinant attenuated *Salmonella* vaccine vectors. Crit. Rev. Immunol., 2010, pp. 255-270, vol. 30.
Curtiss et al., *Salmonella* strains with regulated delayed attenuation in vivo. Infect. Immun., 2009, pp. 1071-1082, vol. 77.
Curtiss et al., *Salmonella typhimurium* deletion mutants lacking adenylate cyclase and cyclic AMP receptor protein are avirulent and immunogenic. Infect Immun, 1987, pp. 3035-3043, vol. 55.
Curtiss et al., Stabilization of recombinant avirulent vaccine strains in vivo. Res Microbiol, 1990, pp. 797-805, vol. 141.
Curtiss, Bacterial infectious disease control by vaccine development. J. Clin. Investig., 2002, pp. 1061-1066, vol. 110.
Curtiss, Chromosomal aberrations associated with mutations to bacteriophage resistance in *Escherichia coli*. J. Bacteriol., 1965, pp. 28-40, vol. 89.

(56) References Cited

OTHER PUBLICATIONS

Daigle et al., Identification of *Salmonella typhi* genes expressed within macrophages by selective capture of transcribed sequences (SCOTS). Mol Microbiol, 2001, pp. 1211-1222, vol. 41.

Darzins. Nucleotide-sequence analysis of the phosphomannose isomerase gene (PMI) of *Pseudomonas aeruginosa* and comparison with the corresponding *Escherichia coli* gene mana. Gene, 1986, pp. 293-302, vol. 42, No. 3.

Dean, 1997. Import of plasmid DNA into the nucleus is sequence specific. Exp. Cell Res., 1997, pp. 293-302, vol. 230.

Doggett et al., Immune responses to *Streptococcus sobrinus* surface protein antigen A expressed by recombinant *Salmonella typhimurium*. Infect Immun, 1993, pp. 1859-1866, vol. 61.

Dunstan et al., Comparison of the Abilities of Different Attenuated *Salmonella typhimurium* Strains to Elicit Humoral Immune Responses against a Heterologous Antigen. Infect. Immun., 1998, pp. 732-740, vol. 66.

Dusek et al., Brown, Systemic and mucosal immune responses in mice orally immunized with avirulent *Salmonella typhimurium* expressing a cloned *Porphyromonas gingivalis* hemagglutinin. Infect Immun, 1994, pp. 1652-1657, vol. 62, No. 5.

Egan et al., A regulatory cascade in the induction of rhaBAD. J Mol Biol, 1993, pp. 97-98, vol. 234.

Egorov et al., Transfectant influenza A viruses with long deletions in the NS1 protein grow efficiently in Vero cells. J. Virol., 1998, pp. 6437-6441, vol. 72.

Enami et al., Introduction of site-specific mutations into the genome of influenza virus. Proc. Natl. Acad. Sci. USA, 1990, pp. 3802-3805, vol. 87.

Fodor et al., Rescue of influenza A virus from recombinant DNA. J. Virol., 1999, pp. 9679-9682, vol. 73.

Formal et al., Construction of a potential bivalent vaccine strain: introduction of *Shigella sonnei* form I antigen genes into the galE *Salmonella typhi* Ty21a typhoid vaccine strain. Infect. Immun., 1981, pp. 746-750, vol. 34.

Fraser et al., The amino acid composition of T3 bacteriophage. J Biol Chem, 1953, pp. 291-295, vol. 205, No. 1.

Galan et al., Cloning and molecular characterization of genes whose products allow *Salmonella typhimurium* to penetrate tissue culture cells. Proc Natl Acad Sci U S A, 1989, pp. 6383-6387, vol. 86.

Galen et al., Optimization of Plasmid Maintenance in the Attenuated Live Vector Vaccine Strain *Salmonella typhi* CVD 908-htrA. Infect. Immun., 1999, pp. 6424-6433, vol. 67.

Garmory et al., Antibiotic-free plasmid stabilization by operator-repressor titration for vaccine delivery by using live *Salmonella enterica* serovar *typhimurium*. Infect. Immun., 2005, pp. 2005-2011, vol. 73.

Gay et al., Positive selection procedure for entrapment of insertion sequence elements in gram-negative bacteria. J Bacteriol, 1985, pp. 918-921, vol. 164, No. 2.

Gentschev et al., Delivery of the p67 sporozoite antigen of *Theileria parva* by using recombinant *Salmonella dublin*: secretion of the product enhances specific antibody responses in cattle. Infect. Immun., 1998, pp. 2060-2064, vol. 66.

Gerdil, The annual production cycle for influenza vaccine. Vaccine, 2003, pp. 1776-1779, vol. 21.

Ghany et al. Candidate live, attenuated *Salmonella enterica* serotype *typhimurium* vaccines with reduced fecal shedding are immunogenic and effective oral vaccines. Infect. Immun., 2007, pp. 1835-1842, vol. 75.

Greenwood, The epidemiology of pneumococcal infection in children in the developing world. Philos. Trans. R. Soc. Lond. B. Biol. Sci., 1999, pp. 777-785, vol. 354.

Gulig et al., Plasmid-associated virulence of *Salmonella typhimurium*. Infect Immun, 1987, pp. 2891-2901, vol. 55.

Guzman et al., Tight regulation, modulation, and high-level expression by vectors containing the arabinose PBAD promoter. J Bacteriol, 1995, pp. 4121-4130, vol. 177.

Hall et al., The role of fur in the acid tolerance response of *Salmonella typhimurium* is physiologically and genetically separable from its role in iron acquisition. J Bacteriol, 1996, pp. 5683-5691, vol. 178.

Hess et al., Superior efficacy of secreted over somatic antigen display in recombinant *Salmonella* vaccine induced protection against listeriosis. Proc. Natl. Acad. Sci. USA, 1996, pp. 1458-1463, vol. 93.

Hicks et al., Incidence of pneumococcal disease due to non-pneumococcal conjugate vaccine (PCV7) serotypes in the United States during the era of widespread PCV7 vaccination, 1998-2004. J Infect Dis, 2007, pp. 1346-1354, vol. 196.

Hitchcock et al., Morphological heteronucleic acid sequenceity among *Salmonella* lipopolysaccharide chemotypes in silver-stained polyacrylamide gels. J Bacteriol, 1983, pp. 269-277, vol. 154, No. 1.

Hoffmann et al., "Ambisense" approach for the generation of influenza A virus: vRNA and mRNA synthesis from one template. Virology, 2000, pp. 310-317, vol. 267.

Hohmann et al., Macrophage-inducible expression of a model antigen in *Salmonella typhimurium* enhances immunogenicity. Proc Natl Acad Sci U S A, 1995, pp. 2904-2908, vol. 92, No. 7.

Hollingshead et al., Diversity of PspA: mosaic genes and evidence for past recombination in *Streptococcus pneumoniae*. Infect Immun., 2000, pp. 5889-5900, vol. 68.

Hopkins et al., A recombinant *Salmonella typhimurium* vaccine induces local immunity by four different routes of immunization. Infect Immun, 1995, pp. 3279-3286, vol. 63.

Jin et al., Multiple amino acid residues confer temperature sensitivity to human influenza virus vaccine strains (FluMist) derived from cold-adapted A/Ann Arbor/6/60. Virology, 2003, pp. 18-24, vol. 306.

Kang et al., Immune responses dependent on antigen location in recombinant attenuated *Salmonella typhimurium* vaccines following oral immunization. FEMS Immunol. Med. Microbiol. Lett., 2003, pp. 99-104, vol. 37.

Kang et al., Immune responses to recombinant pneumococcal PspA antigen delivered by live attenuated *Salmonella enterica* serovar *typhimurium* vaccine. Infect. Immun., 2002, pp. 1739-1749, vol. 70.

Kang et al., Transduction-mediated transfer of unmarked deletion and point mutations through use of counterselectable suicide vectors. J Bacteriol, 2002, pp. 307-312, vol. 184.

Katzman et al., Invertebrate connective tissue. Isolation of D-arabinose from sponge acidic polysaccharide. Biochem J, 1970, pp. 17-19, vol. 119, No. 1.

Kennedy et al., Attenuation and immunogenicity of Delta cya Delta crp derivatives of *Salmonella choleraesuis* in pigs. Infection and Immunity, 1999, pp. 4628-4636, vol. 67, No. 9.

Kilbourne, Studies on influenza in the pandemic of 1957-1958. III. Isolation of influenza A (Asian strain) viruses from influenza patients with pulmonary complications; details of virus isolation and characterization of isolates, with quantitative comparison of isolation methods. J. Clin. Invest., 1959, pp. 266-274, vol. 38.

Klumpp et al., Roles of the influenza virus polymerase and nucleoprotein in forming a functional RNP structure. EMBO J., 1997, pp. 1248-1257, vol. 16.

Kong et al, Regulated programmed lysis of recombinant *Salmonella* in host tissues to release protective antigens and confer biological containment. PNAS, 2008, pp. 9361-9366, vol. 105, No. 27.

Konjufca et al., A Recombinant Attenuated *Salmonella enterica* Serovar *typhimurium* Vaccine Encoding *Eimeria acervulina* Antigen Offers Protection against *E. acervulina* Challenge. Infect. Immun., 2006, pp. 6785-6796, vol. 74.

Kotton et al., Enteric pathogens as vaccine vectors for foreign antigen delivery. Infect. Immun., 2004, pp. 5535-5547, vol. 72.

Lee et al., Characterization of recent H5 subtype avian influenza viruses from US poultry. Avian Pathol., 2004, pp. 288-297, vol. 33.

Lee et al., Mechanism of araC autoregulation and the domains of two overlapping promoters, PC and PBAD, in the L-arabinose regulatory region of *Escherichia coli*. Proc. Natl. Acad. Sci. U S A, 1981, pp. 752-756, vol. 78.

Li et al., A sopB Deletion Mutation Enhances the Immunogenicity and Protective Efficacy of a Heterologous Antigen Delivered by Live Attenuated *Salmonella enterica* Vaccines. Infection and Immunity, 2008, pp. 5238-5246, vol. 76, No. 11.

Lee et al., Trigger factor retards protein export in *Escherichia coli*. J Biol Chem, 2002, pp. 43527-43535, vol. 277.

(56) References Cited

OTHER PUBLICATIONS

Lefeber et al., Th1-directing adjuvants increase the immunogenicity of oligosaccharide-protein conjugate vaccines related to *Streptococcus pneumoniae* type 3. Infect Immun, 2003, pp. 6915-6920, vol. 71.

Loessner et al., Differential effect of auxotrophies on the release of macromolecules by *Salmonella enterica* vaccine strains. FEMS Microbiol. Lett., 2006, pp. 81-88, vol. 265.

Loewen et al., Genetic mapping of katF, a locus that with katE affects the synthesis of a second catalase species in *Escherichia coli*. J Bacteriol, 1984, pp. 668-675, vol. 160.

Luytjes et al., Amplification, expression, and packaging of foreign gene by influenza virus. Cell, 1989, pp. 1107-1113, vol. 59.

Malley et al., CD4+ T cells mediate antibody-independent acquired immunity to pneumococcal colonization. PNAS, 2005, pp. 4848-4853, vol. 102.

Massin et al., Cloning of the chicken RNA polymerase I promoter and use for reverse genetics of influenza A viruses in avian cells. J. Virol., 2005, pp. 13811-13816, vol. 79.

Matthay et al., Evaluation of the opsonic requirements for phagocytosis of *Streptococcus pneumoniae* serotypes VII, XIV, and XIX by chemiluminescence assay. Infect Immun, 1981, pp. 228-235, vol. 31.

McClelland et al., Complete genome sequence of *Salmonella enterica* serovar *typhimurium* LT2. Nature, 2001, pp. 852-856, vol. 413, No. 6858.

McDaniel et al., Monoclonal antibodies against protease sensitive pneumococcal antigens can protect mice from fatal infection with *Streptococcus pneumoniae*. J. Exp. Med., 1984, pp. 368-397, vol. 160.

McDaniel et al., Use of insertional inactivation to facilitate studies of biological properties of pneumococcal surface protein A (PspA). J. Exp. Med., 1987, pp. 381-394, vol. 165.

Mesika et al., A regulated, NF κB-assisted import of plasmid DNA into mammalian cell nuclei. Mol. Ther., 2001, pp. 653-657, vol. 3.

Miller et al., A novel suicide vector and its use in construction of insertion mutations: osmoregulation of outer membrane proteins and virulence determinants in *Vibrio cholerae* requires toxR. J Bacteriol, 1988, pp. 2575-2583, vol. 170.

Miller et al., Bacteriophage T4 genome. Microbiol Mol Biol Rev, 2003, pp. 86-156, vol. 67, No. 1.

Molinari et al., The annual impact of seasonal influenza in the US: measuring disease burden and costs. Vaccine, 2007, pp. 5086-5096, vol. 25.

Mulvey et al., Regulation of transcription of katE and katF in *Escherichia coli*. J Bacteriol, 1990, pp. 6713-6720, vol. 172.

Murti et al., Localization of RNA polymerases on influenza viral ribonucleoproteins by immunogold labeling. Virology, 1988, pp. 562-566, vol. 164.

Nardelli-Haefliger et al., Human papillomavirus type 16 virus-like particles expressed in attenuated *Salmonella typhimurium* elicit mucosal and systemic neutralizing antibodies in mice. Infect Immun, 1997, pp. 3328-3336, vol. 65.

Nayak et al., A live recombinant avirulent oral *Salmonella* vaccine expressing pneumococcal surface protein A induces protective responses against *Streptococcus pneumoniae*. Infect Immun., 1998, pp. 3744-3751, vol. 66.

Neumann et al., An improved reverse genetics system for influenza A virus generation and its implications for vaccine production. Proc. Natl. Acad. Sci. USA, 2005, pp. 16825-16829, vol. 102.

Neumann et al., Generation of influenza A viruses entirely from cloned cDNAs. Proc. Natl. Acad. Sci. USA, 1999, pp. 9345-9350, vol. 96.

Neumann et al., RNA polymerase I-mediated expression of influenza viral RNA molecules. Virology, 1994, pp. 477-479, vol. 202.

Nickerson et al., Role of sigma factor RpoS in initial stages of *Salmonella typhimurium* infection. Infect Immun, 1997, pp. 1814-1823, vol. 65.

Noda et al., Architecture of ribonucleoprotein complexes in influenza A virus particles. Nature, 2006, pp. 490-492, vol. 439.

Oehler et al., The three operators of the lac operon cooperate in repression. EMBO J, 1990, pp. 973-979, vol. 9, No. 4.

Ogunniyi et al., Contributions of Pneumolysin, Pneumococcal Surface Protein A (PspA), and PspC to Pathogenicity of *Streptococcus pneumoniae* D39 in a Mouse Model. Infect. Immun., 2007, pp. 1843-1851, vol. 75.

Osterholm, Preparing for the next pandemic. N. Engl. J. Med., 2005, pp. 1839-1842, vol. 352.

Ozaki et al., Generation of high-yielding influenza A viruses in African green monkey kidney (Vero) cells by reverse genetics. J. Virol., 2004, pp. 1851-1857, vol. 78.

Park et al., Engineered viral vaccine constructs with dual specificity: avian influenza and Newcastle disease. Proc. Natl. Acad. Sci. USA, 2006, pp. 8203-8208, vol. 103.
Pascual et al., Expression of Recombinant Enterotoxigenic *Escherichia coli* Colonization Factor Antigen I by *Salmonella typhimurium* Elicits a Biphasic T Helper Cell Response. Infect. Immun., 1999, pp. 6249-6256, vol. 67.
Pashine et al., Th1 dominance in the immune response to live *Salmonella typhimurium* requires bacterial invasiveness but not persistence. Int. Immunol., 1999, pp. 481-489, vol. 11.
Peterson et al., RpoS proteolysis is regulated by a mechanism that does not require the SprE (RssB) response regulator phosphorylation site. J Bacteriol, 2004, pp. 7403-7410, vol. 186.
Pizarro-Cerda et al., The bacterial signal molecule, ppGpp, regulates *Salmonella* virulence nucleic acid sequence expression. Mol Microbiol, 2004, pp. 1827-1844, vol. 52, No. 6.
Prouty et al., *Salmonella enterica* serovar *typhimurium* invasion is repressed in the presence of bile. Infect Immun, 2000, pp. 6763-6769, vol. 68.
Quinlivan et al., Attenuation of equine influenza viruses through truncations of the NS1 protein. J. Virol., 2005, pp. 8431-8439, vol. 79.
Rand, Crystal violet can be used to visualize DNA bands during gel electrophoresis and to improve cloning efficiency. Tech. Tips Online, 1996 http://www.science-direct.com/science/journal/13662120.
Roberts et al., Oral vaccination against tetanus: comparison of the immunogenicities of *Salmonella* strains expressing fragment C from the nirB and htrA promoters. Infect. Immun., 1998, pp. 3080-3087, vol. 66.
Romeo et al., Genetic regulation of glycogen biosynthesis in *Escherichia coli*: in vitro effects of cyclic AMP and guanosine 5'-diphosphate 3'-diphosphate and analysis of in vivo transcripts. J Bacteriol, 1989, pp. 2773-2782, vol. 171.
Sadler et al., A perfectly symmetric lac operator binds the lac repressor very tightly. Proc Natl Acad Sci U S A, 1983, pp. 6785-6789, vol. 80, No. 22.
Saeland et al., Serum samples from infants vaccinated with a pneumococcal conjugate vaccine, PncT, protect mice against invasive infection caused by *Streptococcus pneumoniae* serotypes 6A and 6B. J Infect Dis, 2001, pp. 253-260, vol. 183.
Schodel et al., Hybrid hepatitis B virus core-pre-S proteins synthesized in avirulent *Salmonella typhimurium* and *Salmonella typhi* for oral vaccination. Infect Immun, 1994, pp. 1669-1676, vol. 62, No. 5.
Schodel, Recombinant avirulent *Salmonellae* as oral vaccine carriers. Infection, 1992, pp. 1-8, vol. 20.
Schuchat et al., Bacterial meningitis in the United States in 1995. Active Surveillance Team. N Engl J Med, 1997, pp. 970-976, vol. 337.
Schulman et al., Independent variation in nature of hemagglutinin and neuraminidase antigens of influenza virus: distinctiveness of hemagglutinin antigen of Hong Kong-68 virus. Proc. Natl. Acad. Sci. USA, 1969, pp. 326-333, vol. 63.
Siegele et al., Gene Expression from plasmids containing the araBAD promoter at subsaturating inducer concentrations represents mixed populations. Proc Natl Acad Sci U S A, 1997, pp. 8168-8172, vol. 94, No. 15.
Simonsen et al., The impact of influenza epidemics on hospitalizations. J. Infect. Dis., 2000, pp. 831-837, vol. 181.
Song et al., Organization and regulation of the D-xylose operons in *Escherichia coli* K-12: XylR acts as a transcriptional activator. J Bacteriol, 1997, pp. 7025-7032, vol. 179.
Spellberg et al., Type 1/type 2 immunity in infectious diseases. Clin. Infect. Dis., 2001, pp. 76-102, vol. 32.

(56) References Cited

OTHER PUBLICATIONS

Schnaitman et al., Genetics of Lipopolysaccharide Biosynthesis in Enteric Bacteria. Microbiological Reviews, 1993, pp. 655-682, vol. 57, No. 3.
Srinivasan et al., Oral immunization with attenuated *Salmonella* expressing human sperm antigen induces antibodies in serum and the reproductive tract. Biol Reprod, 1995, pp. 462-471, vol. 53.
Steel et al., Live attenuated influenza viruses containing NS1 truncations as vaccine candidates against H5N1 highly pathogenic avian influenza. J. Virol., 2009, pp. 1742-1753, vol. 83.
Tacket et al., Safety and immunogenicity in humans of an attenuated *Salmonella typhi* vaccine vector strain expressing plasmid-encoded hepatitis B antigens stabilized by the asd-balanced lethal vector system. Infect Immun, 1997, pp. 3381-3385, vol. 65.
Taubenberger et al., 1918 Influenza: the mother of all pandemics. Emerg. Infect. Dis., 2006, pp. 15-22, vol. 12.
Török et al., Accumulation of ppGpp in a relA mutant of *Escherichia coli* during amino acid starvation. J. Biol. Chem., 1980, pp. 3838-3840, vol. 255.
Tu et al., The PhoP/PhoQ two-component system stabilizes the alternative sigma factor RpoS in *Salmonella enterica*. Proc Natl Acad Sci U S A., 2006, pp. 13503-13508, vol. 103.
Tumpey et al., Characterization of the reconstructed 1918 Spanish influenza pandemic virus. Science, 2005, pp. 77-80, vol. 310.
Van Rossum et al., Host and bacterial factors contributing to the clearance of colonization by *Streptococcus pneumoniae* in a murine model. Infect Immun, 2005, pp. 7718-7726, vol. 73.
Van Velkinburgh et al., PhoP-PhoQ-regulated loci are required for enhanced bile resistance in *Salmonella* spp. Infect Immun, 1999, pp. 1614-1622, vol. 67.
Webster et al., Evolution and ecology of influenza A viruses. Microbiol Rev, 1992, pp. 152-179, vol. 56.
Wilmes-Riesenberg et al., Role of acid tolerance response in virulence of *Salmonella typhimurium*. Infect.Immun, 1996, pp. 1085-1092, vol. 64.
Wu et al., The mechanism underlying T cell help for induction of an antigen-specific in vivo humoral immune response to intact *Streptococcus pneumoniae* is dependent on the type of antigen. J Immunol, 2002, pp. 5551-5557, vol. 168.
Zahn, Overexpression of an mRNA dependent on rare codons inhibits protein synthesis and cell growth. J Bacteriol, 1996, pp. 2926-2933, vol. 178, No. 10.
Zhang et al., Characterization and immunogenicity of *Salmonella typhimurium* SL1344 and UK-1 crp and cdt deletion mutants. Infect. Immun., 1997, pp. 5381-5387, vol. 65.
Zobel et al., RNA polymerase I catalysed transcription of insert viral cDNA. Nucleic. Acids. Res., 1993, pp. 3607-3614, vol. 21.
Baek et al., Leucine-Responsive Regulator Protein (Lrp) Acts as a Virulence Respressor in *Salmonella enterica* Servoar *typhimurium*. Journal of Bacteriology, 2009, pp. 1278-1292, vol. 191, No. 4.
PCT/US2011/061896—International Search Report and Written Opinion of the International Searching Authority, Apr. 5, 2012.
Byl et al, Sequence of the Genomore of *Salmonella* Bacteriophage P22. Journal of Bacteriology, 2000, pp. 6472-6484, vol. 182, 22.
Houng et al., Expression of Vi antigen in *Escherichia coli* K-12: characterization of ViaB from *Citrobacter freundii* and identity of ViaA with RcsB. J.Bacterio, 1992, pp. 5910-5915, vol. 174, No. 18.
Hori et al, Constructionof selt-disruptive *Bacillus megaterium* in response to substrate exhaustion for polyhydroxybutryrate production. Appl Microbiol Biotechnol, 2002, pp. 211-216, vol. 59.
Hurme et al, A Proteinaceous Gene Regulator Thermameter in *Salmonella*. Cell, 1997, pp. 55-64, vol. 90.
Kong et al., Salmonelle synthesizing 1-Monophosphorylated Lipopolysaccharide Exhibits Low Endotoxic while Retaining Its Immunogenicity. J Immunol, 2011, pp. 412-423, vol. 187.
Pickard et al., Characterization of defined ompR mutants of *Salmonella typhi*: ompR is involved in the regulation of Vi polysaccharide expression. Infect Immun, 1994, pp. 3984-3993, vol. 62, No. 9.

Reed et al., The W-Beijing Lineage of *Mycobacterium tuberculosis* Overproduces Triglycerides and Has the DosR Dormancy Regulon Constitutively Upregulated. Journal of Bacteriology, 2007, pp. 2583-2589, vol. 189, No. 7.
Takaya et al., The ATP-Dependent Lon Protease of *Salmonella enterica* Serovar *typhimurium* Regulates Invasion and Expression of Genes Carried on *Salmonella* Pathogenicity Island 1. Journal of Bacteriology, 2002, pp. 224-232, vol. 184, No. 1.
Waltman et al., Biochemical Characteristics of *Edwardsiella ictaluri*. Applied and Enviornmental Microbiology, 1986, pp. 101-104, vol. 51, No. 1.
Sun et al., Highly efficient method for introducing successive multiple scarless gene deletions and markerless gene insertions into the *Yersinia pestis* chromosome. Appl Environ Microbiol, 2008, pp. 4241-4245, vol. 74.
U.S. Appl. No. 13/006,072, Office Action dated Apr. 19, 2012.
Nieto et al., Complex Structure of the nuclear translocation signal of influenza virus polymerase PA subunit. Journal of General Nirology, 1994, pp. 29-36, vol. 75.
U.S. Appl. No. 12/681,721, Office Action dated May 24, 2012.
Ellis, New Technologies for Making Vaccines., in Vaccines, 1988, Chapter 29 pp. 568-575, W.B. Saunders Company, Philadelphia.
Houghten et al, Relative Importance of Position and Individual Amino Acid Residues in Peptide Antigen-Antibody Interactions: Implications in the Mechanism of Antigenic Drift and Antigenic Shift, in Vaccines, 1986, pp. 21-25, Cold Spring Harbor Laboratory.
Greenspan et al, Defining Epitopes: It's Not as Easy as it Seems. Nature Biotechnology, 1999, pp. 936-937, vol. 17.
Sheehan et al., Generation and characterization of hamster monoclonal antibodies that neutralize murine tumor necrosis factors. J Immunol, 1989, pp. 3884-3893, vol. 142.
Sizemore et al., Attenuated bacteria as a DNA delivery vehicle for DNA-mediated immunization. Vaccine, 1997, pp. 804-807, vol. 15.
Snapper et al., Distinct types of T-cell help for the induction of a humoral immune response to *Streptococcus pneumoniae*. Trends Immunol, 2001, pp. 308-311, vol. 22.
Sodeinde et al., Plasminogen activator/coagulase gene of *Yersinia pestis* is responsible for degradation of plasmid-encoded outer membrane proteins. Infect Immun, 1988, pp. 2749-2752, vol. 56.
Sternberg et al., Bacteriophage-mediated nucleic acid sequenceralized transduction in *Escherichia coli* and *Salmonella typhimurium*. Methods Enzymol, 1991, pp. 18-43, vol. 204.
Straley et al., Virulence genes regulated at the transcriptional level by Ca2+ in *Yersinia pestis* include structural genes for outer membrane proteins. Infect Immun, 1986, pp. 445-454, vol. 51.
Sun et al., The role of relA and spoT in *Yersinia pestis* KIM5+ pathogenicity. PLoS One, 2009, pp. E6720, vol. 4.
Thompson et al., The bacterial signal molecule, ppGpp, mediates the environmental regulation of both the invasion and intracellular virulence gene programs of *Salmonella*. J Biol Chem, 2006, pp. 30112-30121, vol. 281.
Une et al., In vivo comparison of avirulent Vwa- and Pgm- or Pstr phenotypes of Yersiniae. Infect Immun, 1984, pp. 895-900, vol. 43.
Uzzau et al., Epitope tagging of chromosomal genes in *Salmonella*. Proc Natl Acad Sci U S A, 2001, pp. 15264-15269, vol. 98.
Viboud et al., *Yersinia* outer proteins: role in modulation of host cell signaling responses and pathogenesis. Annu Rev Microbiol, 2005, pp. 69-89, vol. 59.
Wasserman et al., Two alanine racemase genes in *Salmonella typhimurium* that differ in structure and function. J. Bacteriol., 1983, pp. 1439-1450, vol. 153.
Whitfield, Biosynthesis and assembly of capsular polysaccharides in *Escherichia coli*. Annu Rev. Biochem., 2006, pp. 39-68, vol. 75.
Winter et al., The *Salmonella enterica* serotype Typhi regulator TviA reduces interleukin-8 production in intestinal epithelial cells by repressing flagellin secretion. Cell Microbiol, 2008, pp. 247-261, vol. 10, No. 1.
Wolf et al., Evolution of aminoacyl tRNA synthetases—analysis of unique domain architectures and phylogenetic trees reveals a complex history of horizontal gene transfer events. Genome Res, 1999, pp. 689-710, vol. 9.

(56) References Cited

OTHER PUBLICATIONS

Xiao et al., Residual guanosine 39,59-bispyrophosphate synthetic activity of relA null mutants can be eliminated by spoT null mutations. J Biol Chem, 1991, pp. 5980-5990, vol. 266.
Zahorchak et al., Effect of exogenous nucleotides on Ca2+ dependence and V antigen synthesis in *Yersinia pestis*. Infect Immun, 1982, pp. 953-959, vol. 38.
Zhang et al., A "one-plasmid" system to generate influenza virus in cultured chicken cells for potential use in influenza vaccine. J. Virol., 2009, pp. 9296-9303, vol. 83.
Zhang et al., Transcription activation parameters at ara pBAD. J Mol Biol, 1996, pp. 14-24, vol. 258, No. 1.
Zinkernagel et al., Antigen localisation regulates immune responses in a dose- and time-dependent fashion: a geographical view of immune reactivity. Immunol Rev, 1997, pp. 199-209, vol. 156.
Briles et al., PspA, a protection-eliciting pneumococcal protein: immunogenicity of isolated native PspA in mice. Vaccine, 1996, pp. 858-867, vol. 14.
Hanisch, et al, The *Ralstonia eutropha* H16 phasin PhaP1 is targeted to intracellular triacylglycerol inclusions in *Rhodococcus opacus* PD630 and *Mycobacterium smegmatis* mc2155, and provides an anchor to target other proteins.
Kong et al, Regulated Delayed Expression of rfaH in an Attenuated *Salmonella enterica* Serovar *typhimurium* Vaccine Enhances Immunogenicity of Outer Membrane Proteins and Heterologous Antigen. Infec Immun. 2009, pp. 5572-5582, vol. 77, No. 12.
Lefman et al, Three-Dimensional Electron Microscopic Imaging of Membrane Invaginations in *Escherichia coli* Overproducing the Chemotaxis Receptor Tsr. Journal of Bacteriology, 2004, pp. 5052-5061, vol. 186, No. 15.
Morita et al., Antibacterial Activity of *Bacillus amyloliquefaciencs* Phage Endolysin without Holin Conjugation. Journal of Biosciences and Bioengineering, 2001, pp. 469-473, vol. 91, No. 5.
Navasa et al, Temperature has reciprocal effects on colanic acid and polysialic acid biosynthesis in *E. coli* K92. Appl Microbiol Biotechnol, 2009, pp. 721-729, vol. 82.
Verjan et al, Genetic Loci of Major Antigenic Protein Genes of *Edwardsiella tarda*. Applied and Environmental Microbiology, 2005, pp. 5654-5658, vol. 71, No. 9.
U.S. Appl. No. 12/759,842, Office Action dated Jun. 7, 2012.
U.S. Appl. No. 12/599,655, Office Action dated Jul. 2, 2012.
U.S. Appl. No. 12/599,655, Office Action dated Mar. 12, 2013.
U.S. Appl. No. 12/789,869, Office Action dated Jun. 3, 2014.
U.S. Appl. No. 13/088,141, Office Action dated Apr. 24, 2014.
U.S. Appl. No. 13/574,718, Office Action dated Sep. 6, 2013.
U.S. Appl. No. 13/574,718, Office Action dated Apr. 28, 2014.
U.S. Appl. No. 13/700,591, Office Action dated Apr. 2, 2014.
U.S. Appl. No. 13/898,241, Office Action dated Apr. 17, 2014.
Bittner et al., RpoS and RpoN are involved in the growth-dependent regulation of rtaH transcription and O antigen expression in *Salmonella enterica* serovar Typhi, Microbial Pathogenisis. vol. 36, 2004 (p. 19).
Liu et al., Nickel-inducible lysis system in *Synechocystis* sp. PCC 6803. PNAS, vol. 106, 2009, pp. 21550-21554.
Liu et al., CO2—limitation-inducible Green Recovery of fatty acids from cyanobacterial biomass. PNAS, vol. 108, 2011 pp. 6905-6908.
Moreno et al., *Salmonella* as Live Trojan Horse for Vaccine Development and Cancer Gene Therapy. Current Gene Therapy, 2010, 10, pp. 56-76.
U.S. Appl. No. 13/302,575, Office Action dated Jun. 18, 2013.
Folkesson et al., Components of the peptidoglycan-recycling pathway modulate invasion and intracellular survival of *Salmonella enterica* serovar *typhimurium*. Cellular Microbiology, 2005, vol. 7(1) pp. 147-155.
Whitworth et al., Expression of the *Rickettsia prowazekii* pld or tlyC Gene in *Salmonella enterica* Serovar *typhimurium* Mediates Phagosomal Escape, Infection and Immunity, 2005, vol. 73(10), pp. 6668-6673.
Quenee, Lauriane E., et al., *Yersinia pestis* caf1 Variants and the Limits of Plague Vaccine Protection, Infection and Immunity, May 2008, vol. 76, No. 5, pp. 2025-2036.
U.S. Appl. No. 13/088,141, Office Action dated Dec. 6, 2012 (Ginny Portner).
U.S. Appl. No. 13/006,072, Office Action dated Dec. 11, 2012 (Ja'Na Hines).
Kong, W., T-10-, Improving DNA Vaccine Vector for Efficient Vaccine Delivery Using Live Attenuated Bacterial Carrier, The Society, vol. 2008, No. 108, pp. 668.
Mesika, Adi, et al., A Regulated, NF κB-Assisted Import of Plasmid DNA into Mammalian Cell Nuclei, Molecular Therapy, vol. 3, No. 5, May 2001, pp. 653-657.
Ribeiro, Sofia C., et al., The Role of Polyadenylation Signal Secondary Structures on the Resistance of Plasmid Vectors to Nucleases, The Journal of Gene Medicine, vol. 6, 2004, pp. 565-573.
Rytkonen, Anne, et al.,. SseL, a *Salmonella* Deubiquitinase Required for Macrophage Killing and Virulence, PNAS, vol. 104, No. 9, Feb. 27, 2007, pp. 3502-3507.
Wang, Shixia, et al., Hemagglutinin (HA) Proteins from H1 and H3 Serotypes of Influenza a Viruses Require Different Antigen Designs for the Induction of Optimal Protective Antibody Responses as Studied by Codon-Optimized HA DNA Vaccines, Journal of Virology, vol. 80, No. 23, Dec. 2006, pp. 11628-11637.
U.S. Appl. No. 13/302,575, Office Action dated Sep. 25, 2012 (Oluwatosin Ogunbiyi).
U.S. Appl. No. 12/615,872, Office Action dated Oct. 23, 2012 (Jennifer Graser).
American Society of Microbiology, vol. 108; 2008: (p. 668).
International Search Report and Written Opinion from related International application No. PCT/US2008/078993, 5 pgs.

\* cited by examiner

P_trc promoter
                    -35                                    -10
5' AAATGAGCTGTTGACAATTAATCATCCGGCTCGTATAATGTGTGGAATTGTGAGCGGATAACAATTTCACAC<u>AGGA</u>AACAGACC
                                                                                    RBS Bla signal peptide sequence
ATG AGT ATT CAA CAT TTC CGT GTC GCC CTT ATT CCC TTT TTT GCG GCA TTT TGC CTT CCT GTT TTT GCT CAC CCA GAA
 M   S   I   Q   H   F   R   V   A   L   I   P   F   F   A   A   F   C   L   P   V   F   A   H   P   E
ACG CTG GTG AAA GTA AAA GAT GCT GAA GAT CAG TTG GGT GCA CGA GTG GGT TAC ATC GAA CTG GAT CTC AAC AGC GGT AAG ATC CTT GAC CTG AAT CCC GGA ATC GCA GAC CAA GCT 3'
 T   L   V   K   V   K   D   A   E Bla C-terminal end sequence
5' GCA ACT ATG GAT GAA CGA AAT AGA CAG ATC GCT GAG ATA GGT GCC TCA CTG ATT AAG CAT TGG TAA 3'
   A   T   M   D   E   R   N   R   Q   I   A   E   I   G   A   S   L   I   K   H   W   *

P_lpp promoter
                    -35                                      -10
5' AAAAATATTCTCAACATAAAAAACTTTGTGTAATACTTGTAACGCTACATGGAGATTAACTCAATCTAGCTAGAGGCTTTAC
ACTTTATGCTTCCGGCTCGTATAATGTGTGGAATTGTGAGCGGATAACAATTTCACACAGGAAACAGCTATGACCATGATTACGGA
                                    (LacI binding site)
TTCACTGGAACTCTAGATAACG<u>AGGC</u>AAAA
                         RBS OmpA signal peptide sequence
ATG AAA AAG ACA GCT ATC GCG ATT GCA GTG GCA CTG GCT GGT TTC GCT ACC GTA GCG CAG GCC GCG AAT TC 3'
 M   K   K   T   A   I   A   I   A   V   A   L   A   G   F   A   T   V   A   Q   A   N

FIG. 2B

```
         1
CP995-    WDGKIDGTGT HAMIVLKGVS -LENDLSKNE PESVRKNLEI LKENMHELQL GSTYPDYDKN AYDLYQDHFW
ATCC13124- ::::::::::::::::::::TQ:::::I:::::::::::::::::::::::::::::::::::::::::::::

CP995-    DPDTDNNFSK DNSWYLAYSI PDTGESQIRK FSALARYEWQ RGNYKQATFY LGEAMHYFGD IDTPYHPANV
ATCC13124- ::::::::::::::::::::::::::::::::::::::::::::::::::::::::::::::::::::::::::::

CP995-    TAVDSAGIIVK FETFAEERKE QYKINTAGCK TNEDFYADIL KNKDFNAWSK EYARGFAKTG KSIYYSHASM
ATCC13124- :::::::::::::::::::::::::::::::::::A::T:::::::::::::::::::::::::::::::::::::
                                               248

CP995-    SHSWDDWDYA AKVTLANSQK GTAGYIYRFL HDVSEGNDPS VGKNVKELVA YISTSGEKDA GTDDYMYFGI
ATCC13124- ::::::::::::::::::::::::::::::::::::::::::::::::::::::::::::::::::::::::::::

CP995-    KTKDGKTQEW EMDNPGNDFM TGSKDTYTFK LKDENLKIDD IQNMWIRKRK YTAFPDAYKP ENIKIIANGK
ATCC13124- ::::::::::::::::::::::::::::::::::::::::::::::::::::::::::::::::::::::S:::::
                     370
CP995-    VVVDKDINEW ISRKSTYNIK * *
ATCC13124- ::GN:::::::::::::::::
```

FIG. 3

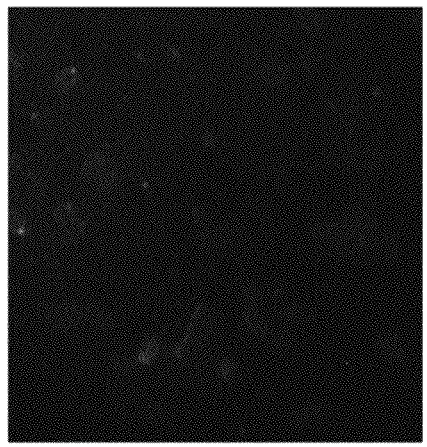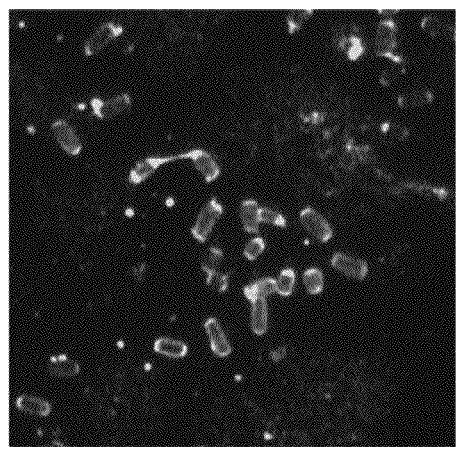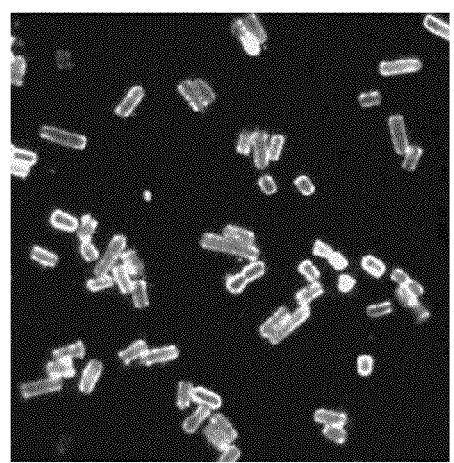
FIG. 8

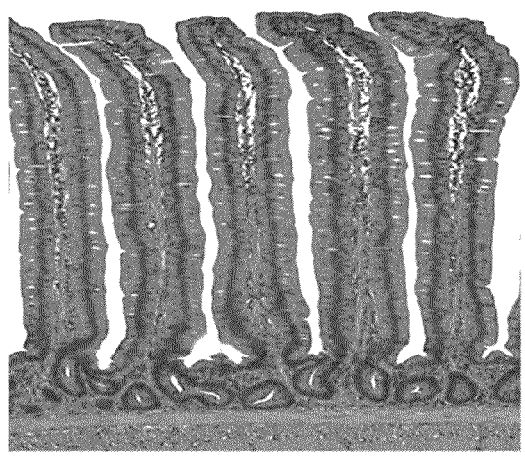
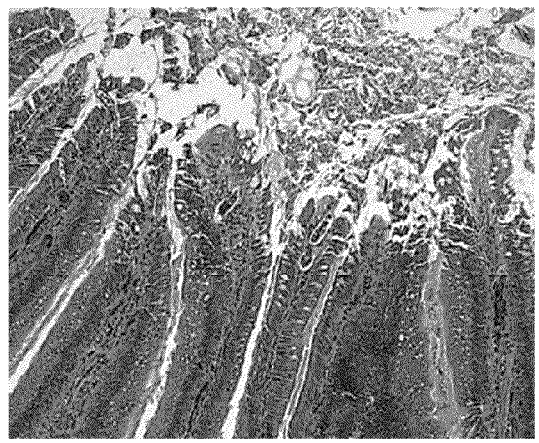
FIG. 9

D
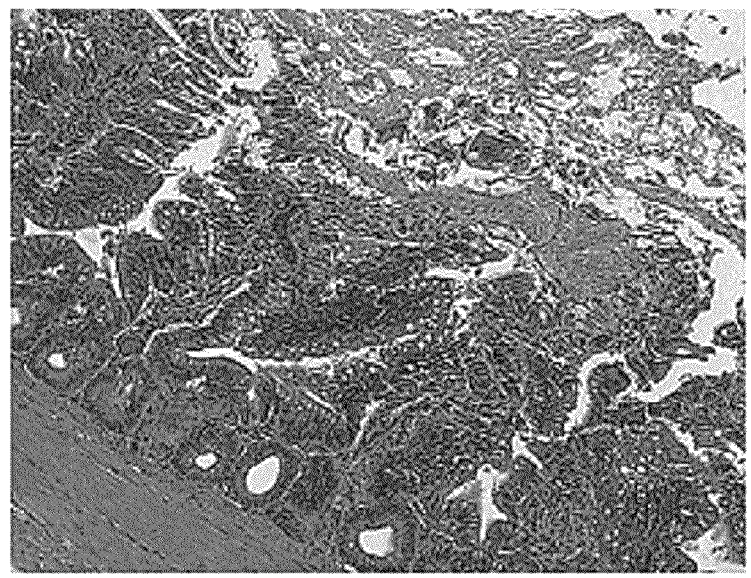
E
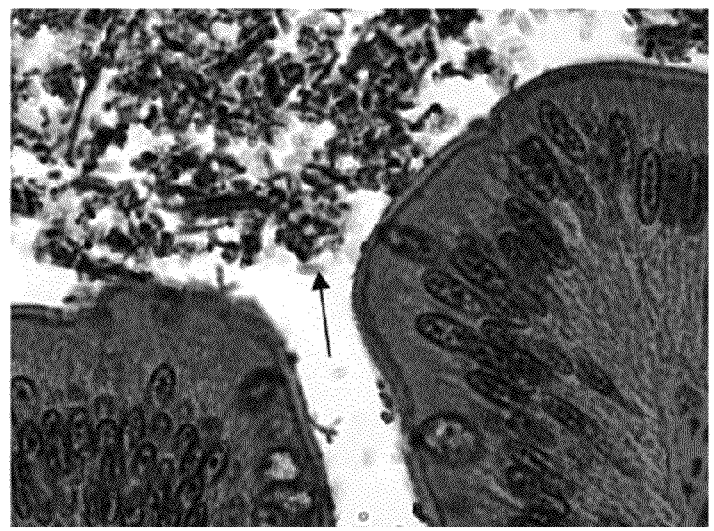
FIG. 9

```
              10           20           30           40           50
    GAATTC GAC CCG TCC GTG GGC AAC AAC GTG AAA GAA CTG GTG GCT TAC ATC TCC
    CTTAAG CTG GGC AGG CAC CCG TTG TTG CAC TTT CTT GAC CAC CGA ATG TAG AGG
            D   P   S   V   G   N   N   V   K   E   L   V   A   Y   I   S>

60           70           80           90          100
    ACT AGC GGC GAA AAA GAC GCT GGC ACC GAC GAC TAC ATG TAT TTC GGC ATC AAA
    TGA TCG CCG CTT TTT CTG CGA CCG TGG CTG CTG ATG TAC ATA AAG CCG TAG TTT
     T   S   G   E   K   D   A   G   T   D   D   Y   M   Y   F   G   I   K>

110          120          130          140          150          160
    ACC AAG GAC GGC AAA ACT CAA GAA TGG GAA ATG GAC AAC CCG GGC AAC GAC TTC
    TGG TTC CTG CCG TTT TGA GTT CTT ACC CTT TAC CTG TTG GGC CCG TTG CTG AAG
     T   K   D   G   K   T   Q   E   W   E   M   D   N   P   G   N   D   F>

170          180          190          200          210
    ATG GCT GGC AGC AAA GAC ACT TAT ACT TTC AAA TTA AAA GAC GAA AAC CTG AAA
    TAC CGA CCG TCG TTT CTG TGA ATA TGA AAG TTT AAT TTT CTG CTT TTG GAC TTT
     M   A   G   S   K   D   T   Y   T   F   K   L   K   D   E   N   L   K>

220          230          240          250          260          270
    ATT GAC GAC ATC CAA AAC ATG TGG ATT CGC AAA CGT AAA TAT ACC GCA TTC CCG
    TAA CTG CTG TAG GTT TTG TAC ACC TAA GCG TTT GCA TTT ATA TGG CGT AAG GGC
     I   D   D   I   Q   N   M   W   I   R   K   R   K   Y   T   A   F   P>

280          290          300          310          320
    GAC GCT TAT AAG CCG GAA AAC ATC AAG GTG ATC GCA AAC GGC AAA GTG GTA GTG
    CTG CGA ATA TTC GGC CTT TTG TAG TTC CAC TAG CGT TTG CCG TTT CAC CAT CAC
     D   A   Y   K   P   E   N   I   K   V   I   A   N   G   K   V   V   V>

330          340          350          360          370
    GAC AAG GAC ATC AAC GAG TGG ATT TCC GGC AAC TCC ACT TAT AAC ATC AAA TAA
    CTG TTC CTG TAG TTG CTC ACC TAA AGG CCG TTG AGG TGA ATA TTG TAG TTT ATT
     D   K   D   I   N   E   W   I   S   G   N   S   T   Y   N   I   K   *>

380
    TAAAAGCTT
    ATTTTCGAA
```

FIG. 10

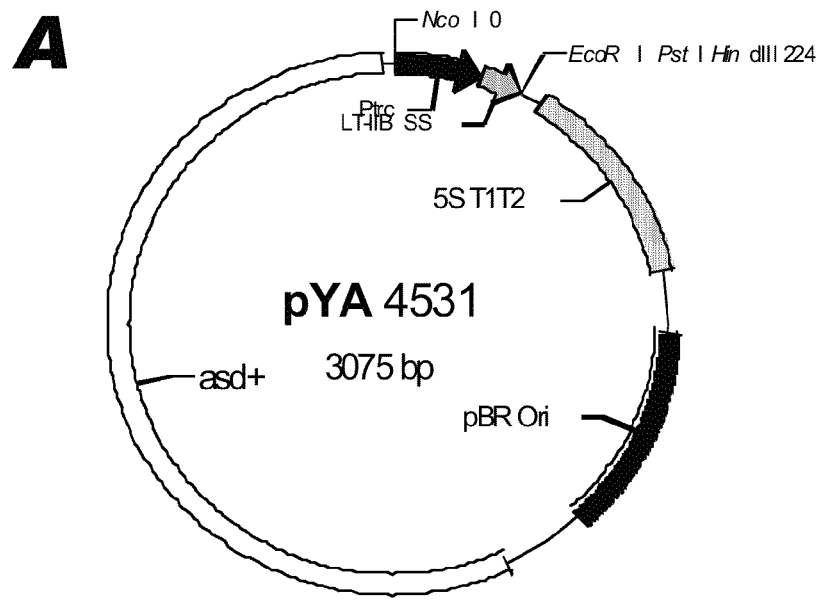
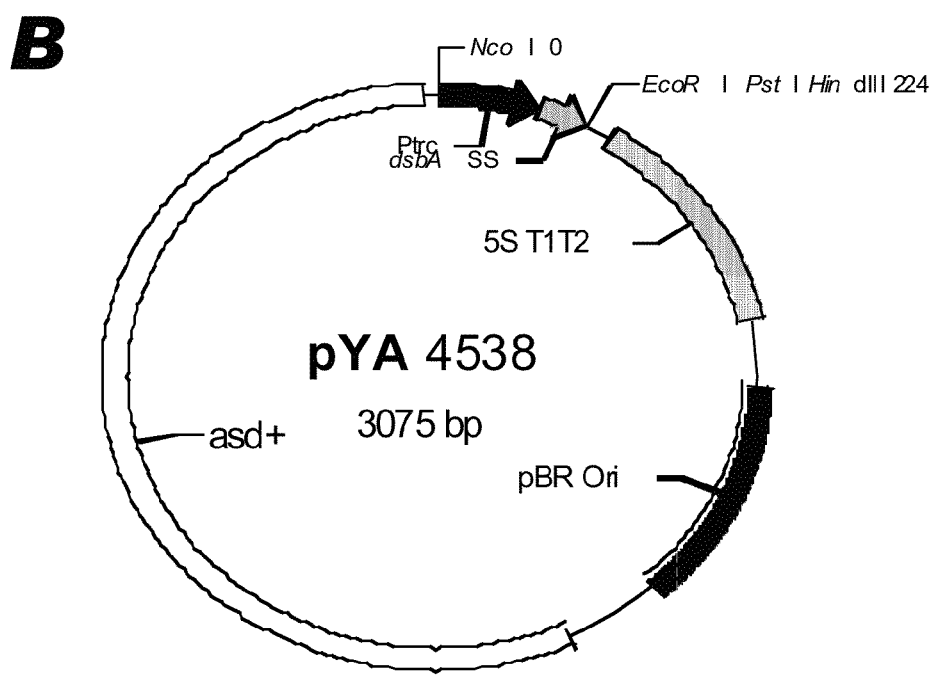
FIG. 11

```
          10              20              30              40              50
GAATTC AGC GAA CTG AAC GAC ATC AAC AAA ATT GAG CTG AAA AAC CTG AGC GGC
CTTAAG TCG CTT GAC TTG CTG TAG TTG TTT TAA CTC GAC TTT TTG GAC TCG CCG
        S   E   L   N   D   I   N   K   I   E   L   K   N   L   S   G>

60              70              80              90             100
GAA ATC ATC AAA GAA AAC GGC AAG GAA GCT ATT AAA TAT ACT TCC AGC GAC ACC
CTT TAG TAG TTT CTT TTG CCG TTC CTT CGA TAA TTT ATA TGA AGG TCG CTG TGG
 E   I   I   K   E   N   G   K   E   A   I   K   Y   T   S   S   D   T>

110             120             130             140             150             160
GCT TCC CAT AAA GGC TGG AAG GCA ACT CTG AGC GGC ACC TTC ATT GAA GAC CCG
CGA AGG GTA TTT CCG ACC TTC CGT TGA GAC TCG CCG TGG AAG TAA CTT CTG GGC
 A   S   H   K   G   W   K   A   T   L   S   G   T   F   I   E   D   P>

170             180             190             200             210
CAT TCC GAC AAG AAA ACT GCT CTG CTG AAC CTG GAA GGC TTT ATC CCG TCC GAC
GTA AGG CTG TTC TTT TGA CGA GAC GAC TTG GAC CTT CCG AAA TAG GGC AGG CTG
 H   S   D   K   K   T   A   L   L   N   L   E   G   F   I   P   S   D>

220             230             240             250             260             270
AAA CAG ATT TTC GGC TCT AAA TAT TAC GGC AAA ATG AAA TGG CCG GAA ACT TAT
TTT GTC TAA AAG CCG AGA TTT ATA ATG CCG TTT TAC TTT ACC GGC CTT TGA ATA
 K   Q   I   F   G   S   K   Y   Y   G   K   M   K   W   P   E   T   Y>

280             290             300             310             320
CGC ATT AAT GTG AAA AGC GCT GAC GTG AAC AAT AAC ATC AAA ATC GCA AAC TCC
GCG TAA TTA CAC TTT TCG CGA CTG CAC TTG TTA TTG TAG TTT TAG CGT TTG AGG
 R   I   N   V   K   S   A   D   V   N   N   N   I   K   I   A   N   S>

330             340             350             360             370
ATT CCG AAA AAT ACT ATC GAC AAA AAA GAC GTG TCC AAT TCC ATT GGC TAT TCC
TAA GGC TTT TTA TGA TAG CTG TTT TTT CTG CAC AGG TTA AGG TAA CCG ATA AGG
 I   P   K   N   T   I   D   K   K   D   V   S   N   S   I   G   Y   S>

380             390             400             410             420             430
ATC GGC GGT AAC ATC TCC GTG GAA GGC AAA ACT GCT GGC GCT GGC ATC AAC GCT
TAG CCG CCA TTG TAG AGG CAC CTT CCG TTT TGA CGA CCG CGA CCG TAG TTG CGA
 I   G   G   N   I   S   V   E   G   K   T   A   G   A   G   I   N   A>

440             450             460             470             480
TCC TAT AAC GTC CAA AAC ACT ATC AGC TAT GAA CAA CCG GAC TTC CGC ACC ATT
AGG ATA TTG CAG GTT TTG TGA TAG TCG ATA CTT GTT GGC CTG AAG GCG TGG TAA
 S   Y   N   V   Q   N   T   I   S   Y   E   Q   P   D   F   R   T   I>

490             500             510             520             530             540
CAA CGC AAA GAC GAT GCA AAC CTG GCA TCC TGG GAC ATC AAA TTC GTT GAG ACT
GTT GCG TTT CTG CTA CGT TTG GAC CGT AGG ACC CTG TAG TTT AAG CAA CTC TGA
 Q   R   K   D   D   A   N   L   A   S   W   D   I   K   F   V   E   T>
```

FIG. 13A

```
         550           560           570           580           590
AAG GAC GGC TAT AAC ATC GAC TCC TAT CAT GCT ATT TAT GGC AAC CAA CTG TTC
TTC CTG CCG ATA TTG TAG CTG AGG ATA GTA CGA TAA ATA CCG TTG GTT GAC AAG
 K   D   G   Y   N   I   D   S   Y   H   A   I   Y   G   N   Q   L   F>

600           610           620           630           640
ATG AAA TCC CGC CTG TAT AAC AAT GGC GAC AAA AAC TTC ACC GAC GAT CGC GAC
TAC TTT AGG GCG GAC ATA TTG TTA CCG CTG TTT TTG AAG TGG CTG CTA GCG CTG
 M   K   S   R   L   Y   N   N   G   D   K   N   F   T   D   D   R   D>

650           660           670           680           690           700
CTG TCC ACC CTG ATT TCC GGC GGC TTC TCC CCG AAC ATG GCT CTG GCA CTG ACC
GAC AGG TGG GAC TAA AGG CCG CCG AAG AGG GGC TTG TAC CGA GAC CGT GAC TGG
 L   S   T   L   I   S   G   G   F   S   P   N   M   A   L   A   L   T>

710           720           730           740           750
GCA CCT AAA AAT GCT AAA GAA TCC GTG ATC ATC GTG GAA TAT CAA CGC TTC GAC
CGT GGA TTT TTA CGA TTT CTT AGG CAC TAG TAG CAC CTT ATA GTT GCG AAG CTG
 A   P   K   N   A   K   E   S   V   I   I   V   E   Y   Q   R   F   D>

760           770           780           790           800           810
AAC GAC TAT ATT CTG AAT TGG GAA ACT ACT CAA TGG CGC GGC ACC AAC AAA CTT
TTG CTG ATA TAA GAC TTA ACC CTT TGA TGA GTT ACC GCG CCG TGG TTG TTT GAA
 N   D   Y   I   L   N   W   E   T   T   Q   W   R   G   T   N   K   L>

820           830           840           850           860
TCC TCA ACC AGC GAA TAT AAC GAA TTT ATG TTC AAA ATC AAC TGG CAA GAC CAT
AGG AGT TGG TCG CTT ATA TTG CTT AAA TAC AAG TTT TAG TTG ACC GTT CTG GTA
 S   S   T   S   E   Y   N   E   F   M   F   K   I   N   W   Q   D   H>

870           880           890
AAA ATC GAA TAT TAT CTG TAA AAGCTT
TTT TAG CTT ATA ATA GAC ATT TTCGAA
 K   I   E   Y   Y   L   *
```

FIG. 13B

```
              1                             30                            60
original:    ACA TTA GAA CCA GTT GGA GAT ATA GAT ACT ACT CCA GAA GGA ACT AAA GCT TGT AAG TTC
Amino Acid:   T   L   E   P   V   G   D   I   D   T   T   P   E   G   T   K   A   C   K   F
Replace:         CTG             GGC     ATC                     GGC 61                            90                           120
original:    TGG GGA TTA GGA TCA GAC GGA ACA GTT GGA GCT AAC AAG AGT GCT ATC AAA ATC ATC GGA
Amino Acid:   W   G   L   G   S   D   G   T   V   G   A   N   K   S   A   I   K   I   I   G
Replace:         GGC CTG GGC             GGC             GGC                             GGC 121                           150                           180
original:    GAC CAT ACT GAC ATG TAT GCT CAA GGA TAC TTT GCA TAT GAC TCT AAA AAA TCA GGT GGG
Amino Acid:   D   H   T   D   M   Y   A   Q   G   Y   F   A   Y   D   S   K   K   S   G   G
Replace:                                         GGC 181                           210                           240
original:    GTT ACA ATT TCT CAC TTA AGA TTC GGT AAA CAA CCA ATA AAA TCA CCT TAC TTA ATA AAC
Amino Acid:   V   T   I   S   H   L   R   F   G   K   Q   P   I   K   S   P   Y   L   I   N
Replace:                         CTG CGC                     ATC                 CTG ATC 241                           270                           300
original:    AAA GCT GAT TTC GTT GCT TGT CAT AAC CAA TCA TAT GTT AAC AAA TAC TTC GTT TTA GAT
Amino Acid:   K   A   D   F   V   A   C   H   N   Q   S   Y   V   N   K   Y   F   V   L   D
Replace:                                                                                 CTG 301                           330                           360
original:    GGA TTA AAG AAA AAC GGA ACA TTC TTA TTA AAC ACT ATC TGG ACT CCA GAA GAA GTT GCT
Amino Acid:   G   L   K   K   N   G   T   F   L   L   N   T   I   W   T   P   E   E   V   A
Replace:     GGC CTG                     GGC         CTG CTG 361                           390                           420
original:    GAA CAT TTA CCA GCA AGC TAT AAG AGA TTC TTA GCT GAA AAC AAC ATT AAG TTC TAC ACT
Amino Acid:   E   H   L   P   A   S   Y   K   R   F   L   A   E   N   N   I   K   F   Y   T
Replace:             CTG                             CGC     CTG 421                           450                           480
original:    TTA AAT GCT GTT AAG ATA GCT CAA GAA GTT GGT TTA GGT GGA AGA ATC AAC ATG ATC ATG
Amino Acid:   L   N   A   V   K   I   A   Q   E   V   G   L   G   G   R   I   N   M   I   M
Replace:     CTG                     ATC                         CTG     GGC CGC 481                           510                           540
original:    CAA TCA GCA TTC TTC AAA CTA GCT AAC ATA ATA CCA GTA GAA GAC GCA GTT AAA TAC TTA
Amino Acid:   Q   S   A   F   F   K   L   A   N   I   I   P   V   E   D   A   V   K   Y   L
Replace:                                     CTG         ATC ATC                             CTG 541                           570                           600
original:    AAA GAC GCT GTT GTA ACT TCA TAC GGT AAA AAA GGT GAA AAA GTT GTT AAC ATG AAC CAC
Amino Acid:   K   D   A   V   V   T   S   Y   G   K   K   G   E   K   V   V   N   M   N   H
Replace:

601                           630                           660
original:    GCT GCT ATA GAC AAA GGA ATC GAC GCT ATC GTT GAA ATC ACT GTT CCA GCT GAG TGG GCT
Amino Acid:   A   A   I   D   K   G   I   D   A   I   V   E   I   T   V   P   A   E   W   A
Replace:             ATC         GGC 661                           690                           720
original:    AAC GCT AAA GAT GAA GTT GTT GAA GCT AAA GAA GTT CCA GCA TTC ATC AAA AAC ATT GTT
Amino Acid:   N   A   K   D   E   V   V   E   A   K   E   V   P   A   F   I   K   N   I   V
Replace:
```

FIG. 16A

```
            721                                    750                                    780
original:   GAA CCA ATG AAC AGA TTA GAA GGA GAT AAA CTT CCT GTA TCA GCA TTC AAC GGA ATG GAA
Amino Acid:  E   P   M   N   R   L   E   G   D   K   L   P   V   S   A   F   N   G   M   E
Replace:                         CGC CTG         GGC                                 GGC 781                                    810                                    840
original:   GAT GGT ACT TTC GAA CCA GGT ACT GCT GCA TAC GAA AAG AGA GGA ATC GGT ATA AAC ATA
Amino Acid:  D   G   T   F   E   P   G   T   A   A   Y   E   K   R   G   I   G   I   N   I
Replace:                                                         CGC GGC         ATC     ATC 841                                    870                                    900
original:   CCA GAA TGG ATA GCA GAC AAC TGT ATC CAA TGT AAC CAA TGT GCT TAC GTT TGT CCT CAT
Amino Acid:  P   E   W   I   A   D   N   C   I   Q   C   N   Q   C   A   Y   V   C   P   H
Replace:                     ATC 901                                    930                                    960
original:   GCT ACA ATA AGA CCA TTC TTA TTA ACT GAG GAA GAA GCT AAA AAT GCT CCT GCT TCA ACT
Amino Acid:  A   T   I   R   P   F   L   L   T   E   E   E   A   K   N   A   P   A   S   T
Replace:             ATC CGC         CTG CTG 961                                    990                                    1020
original:   AAG TTA GTT GCT GCT AAA GCA TTA AAA ACT GAA GAG CCA ATG CAA TTC ACT ATG GCT GTA
Amino Acid:  K   L   V   A   A   K   A   L   K   T   E   E   P   M   Q   F   T   M   A   V
Replace:         CTG                         CTG 1021                                   1050                                   1080
original:   AGT ACT TTA GAC TGT ACT GGA TGT GGA AAC TGT GCT CAA GTT TGT CCT GCT AAG GAA AAA
Amino Acid:  S   T   L   D   C   T   G   C   G   N   C   A   Q   V   C   P   A   K   E   K
Replace:             CTG                 GGC     GGC 1081                                   1110                                   1140
original:   GCT TTA GTT ATG AAA CCA CAA CAT ACT CAA GAA GAT CAA ATA GAA GCT TGG GAT TAC TGT
Amino Acid:  A   L   V   M   K   P   Q   H   T   Q   E   D   Q   I   E   A   W   D   Y   C
Replace:         CTG                                                 ATC 1141                                   1170                                   1200
original:   GTA AAT GAT GTT GTA CCT AAG AAA AAC CCA ATG AAC AAA AAC ACA GTT AAA GGT AGC CAA
Amino Acid:  V   N   D   V   V   P   K   K   N   P   M   N   K   N   T   V   K   G   S   Q
Replace:

1201                                   1230                                   1260
original:   TTC GAG CAA CCA TTA TTC GAG TTC TCA GGA GCT TGT GCT GGA TGT GGA GAA ACT CCA TAT
Amino Acid:  F   E   Q   P   L   F   E   F   S   G   A   C   A   G   C   G   E   T   P   Y
Replace:                     CTG                         GGC         GGC GGC 1261                                   1290                                   1320
original:   GCT AAA CTT ATA ACT CAA TTA TTC GGA GAT AGA ATG ATG ATA GCT AAC GCT ACT GGA TGT
Amino Acid:  A   K   L   I   T   Q   L   F   G   D   R   M   M   I   A   N   A   T   G   C
Replace:             ATC         CTG         GGC CGC         ATC                     GGC 1321                                   1350                                   1380
original:   TCA TCA ATC TGG GGT GGA TCA GCT CCT TCA ACT CCA TAC ACA ACT AAC CAC AAT GGT CAT
Amino Acid:  S   S   I   W   G   G   S   A   P   S   T   P   Y   T   T   N   H   N   G   H
Replace:                         GGC 1381                                   1410                                   1440
original:   GGA CCA GCT TGG GCT AAC TCA TTA TTC GAG GAC AAC GCT GAA TTC GGA TTA GGT ATG TTC
Amino Acid:  G   P   A   W   A   N   S   L   F   E   D   N   A   E   F   G   L   G   M   F
Replace:    GGC                         CTG                             GGC CTG
```

FIG. 16B

```
           1441                                         1470                                        1500
original:  TTA GGA GTT AAA GCT ATA AGA GAA AGA TTA GTT GAT CTT GCT GGA AAA GCA ATT GAA GCT
Amino Acid: L   G   V   K   A   I   R   E   R   L   V   D   L   A   G   K   A   I   E   A
Replace:   CTG GGC         ATC CGC         CGC CTG                 GGC 1501                                         1530                                        1560
original:  GGT GTT AAA CCA GAA GCT AAA GAA GCT TTA GAA GCT TGG ATA GCT GAA GTT GAC AAC GGA
Amino Acid: G   V   K   P   E   A   K   E   A   L   E   A   W   I   A   E   V   D   N   G
Replace:                                           CTG         ATC                         GGC 1561                                         1590                                        1620
original:  GAA GGA ACT AGA GAT AGA GCT GAC GCT GTT GTA GCT GCA TTA CAA GGT GAA ACT AAC GAG
Amino Acid: E   G   T   R   D   R   A   D   A   V   V   A   A   L   Q   G   E   T   N   E
Replace:       GGC     CGC     CGC                             CTG 1621                                         1650                                        1680
original:  TTC GCT AAA GAA ATA TTA AAA GAC CAA GAC TAC TTA GCT AAG AGA TCA CAA TGG ATC TTC
Amino Acid: F   A   K   E   I   L   K   D   Q   D   Y   L   A   K   R   S   Q   W   I   F
Replace:                       ATC CTG                         CTG         CGC
```

FIG. 16C

| | 1 | | | | | | | | | 30 | | | | | | | | | | 60 |
|---|---|---|---|---|---|---|---|---|---|---|---|---|---|---|---|---|---|---|---|---|
| original: | TTC | TGG | GGA | TTT | GAT | AAC | TCA | AAA | GAT | GTT | AAT | TCA | GAT | TTT | AAT | TTT | AGA | ATA | ATG | CCT |
| Amino Acid: | F | W | G | F | D | N | S | K | D | V | N | S | D | F | N | F | R | I | M | P |
| Replace: | | | GGC | | | | TCC | | | | AAC | TCC | | | AAC | | CGC | ATC | | CCG |

| | 61 | | | | | | | | | 90 | | | | | | | | | | 120 |
|---|---|---|---|---|---|---|---|---|---|---|---|---|---|---|---|---|---|---|---|---|
| original: | ATG | GTT | AAA | AAC | CTT | AGT | GGT | GGA | GCA | TTC | ATG | AAT | GCT | GGA | AAT | GGT | GTT | ATA | GGT | ATA |
| Amino Acid: | M | V | K | N | L | S | G | G | A | F | M | N | A | G | N | G | V | I | G | I |
| Replace: | | | | | CTG | TCC | | GGC | | | | AAC | | GGC | AAC | | | ATC | | ATC |

| | 121 | | | | | | | | | 150 | | | | | | | | | | 180 |
|---|---|---|---|---|---|---|---|---|---|---|---|---|---|---|---|---|---|---|---|---|
| original: | AGA | CCT | GGA | AAT | CAG | GAT | GCA | ATA | CTT | GCA | GCT | AAT | AAA | GGA | TGG | GGT | GTT | GCT | CAT | GAA |
| Amino Acid: | R | P | G | N | Q | D | A | I | L | A | A | N | K | G | W | G | V | A | H | E |
| Replace: | CGC | CCG | GGC | AAC | | | | ATC | CTG | | | AAC | | GGC | | | | | | |

| | 181 | | | | | | | | | 210 | | | | | | | | | | 240 |
|---|---|---|---|---|---|---|---|---|---|---|---|---|---|---|---|---|---|---|---|---|
| original: | CTT | GGA | CAT | AAC | TTT | GAT | ACA | GGC | GGA | AGA | ACC | ATA | GTA | GAA | GTA | ACA | AAT | AAT | ATG | ATG |
| Amino Acid: | L | G | H | N | F | D | T | G | G | R | T | I | V | E | V | T | N | N | M | M |
| Replace: | CTG | GGC | | | | | ACC | | GGC | CGC | | ATC | | | | ACC | AAC | AAC | | |

| | 241 | | | | | | | | | 270 | | | | | | | | | | 300 |
|---|---|---|---|---|---|---|---|---|---|---|---|---|---|---|---|---|---|---|---|---|
| original: | CCA | TTA | TTC | TTT | GAG | TCT | AAA | TAT | AAA | ACT | AAA | ACA | AGA | ATA | ACT | GAC | CAA | AAC | ATA | TGG |
| Amino Acid: | P | L | F | F | E | S | K | Y | K | T | K | T | R | I | T | D | Q | N | I | W |
| Replace: | CCG | CTG | | | | | | | | | | ACC | CGC | ATC | | | | | ATC | |

| | 301 | | | | | | | | | 330 | | | | | | | | | | 360 |
|---|---|---|---|---|---|---|---|---|---|---|---|---|---|---|---|---|---|---|---|---|
| original: | GAA | AAC | AAT | ACT | TAC | CCT | AAA | GTT | GGC | TTA | GAT | GAT | TAT | TCT | AAT | AAT | GAG | TTA | TAT | AAT |
| Amino Acid: | E | N | N | T | Y | P | K | V | G | L | D | D | Y | S | N | N | E | L | Y | N |
| Replace: | | | AAC | | | CCG | | | | CTG | | | | | AAC | AAC | | CTG | | AAC |

| | 361 | | | | | | | | | 390 | | | | | | | | | | 420 |
|---|---|---|---|---|---|---|---|---|---|---|---|---|---|---|---|---|---|---|---|---|
| original: | AAG | GCT | GAT | AGT | ACT | CAT | TTA | GCT | CAG | TTA | GCG | CCA | TTA | TGG | CAA | TTA | TAT | TTA | TAT | GAT |
| Amino Acid: | K | A | D | S | T | H | L | A | Q | L | A | P | L | W | Q | L | Y | L | Y | D |
| Replace: | | | | TCC | | | CTG | | | CTG | | CCG | CTG | | | CTG | | CTG | | |

| | 421 | | | | | | | | | 450 | | | | | | | | | | 480 |
|---|---|---|---|---|---|---|---|---|---|---|---|---|---|---|---|---|---|---|---|---|
| original: | AAT | ACT | TTC | TAT | GGA | AAG | TTT | GAA | AGA | CAG | TTT | AGA | GAA | AGA | GAT | TTT | GGA | AAT | AAA | AAT |
| Amino Acid: | N | T | F | Y | G | K | F | E | R | Q | F | R | E | R | D | F | G | N | K | N |
| Replace: | AAC | | | | GGC | | | | CGC | | | CGC | | CGC | | | GGC | AAC | | AAC |

| | 481 | | | | | | | | | 510 | | | | | | | | | | 540 |
|---|---|---|---|---|---|---|---|---|---|---|---|---|---|---|---|---|---|---|---|---|
| original: | AGA | GAA | GAT | ATA | TAT | AAA | TCT | TGG | GTT | GTG | GCA | GCG | TCA | GAT | GCT | ATG | GAG | TTA | GAT | TTA |
| Amino Acid: | R | E | D | I | Y | K | S | W | V | V | A | A | S | D | A | M | E | L | D | L |
| Replace: | CGC | | | ATC | | | | | | | | | TCC | | | | | CTG | | CTG |

| | 541 | | | | | | | | | 570 | | | | | | | | | | 600 |
|---|---|---|---|---|---|---|---|---|---|---|---|---|---|---|---|---|---|---|---|---|
| original: | ACT | GAG | TTC | TTT | GCA | AGA | CAT | GGT | ATT | CGT | GTT | GAT | GAT | AAG | GTT | AAG | GAG | GAT | TTA | GCT |
| Amino Acid: | T | E | F | F | A | R | H | G | I | R | V | D | D | K | V | K | E | D | L | A |
| Replace: | | | | | | CGC | | | | | | | | | | | | | CTG | |

| | 601 | | | | | | | | | 630 | | | | | | | | | | 660 |
|---|---|---|---|---|---|---|---|---|---|---|---|---|---|---|---|---|---|---|---|---|
| original: | AAG | TAT | CCA | AAG | CCT | GAT | AAA | AAG | ATC | TAT | TAC | TTA | AAT | GAT | TTA | GCA | ATG | AAT | TAT | AAA |
| Amino Acid: | K | Y | P | K | P | D | K | K | I | Y | Y | L | N | D | L | A | M | N | Y | K |
| Replace: | | | CCG | | CCG | | | | | | | CTG | AAC | | CTG | | | AAC | | |

| | 661 | | | | | | | | | 690 | | | | | | | | | | 720 |
|---|---|---|---|---|---|---|---|---|---|---|---|---|---|---|---|---|---|---|---|---|
| original: | GGT | GAT | GGA | TTT | ACG | GAT | AAT | GCA | AAG | GTA | TCT | GTA | AGT | ACA | AGT | GGT | TCA | AAT | GGT | AAT |
| Amino Acid: | G | D | G | F | T | D | N | A | K | V | S | V | S | T | S | G | S | N | G | N |
| Replace: | | | GGC | | ACC | | AAC | | | | | | TCC | ACC | TCC | | TCC | AAC | | AAC |

FIG. 17A

```
           721                                       750                                       780
original:  ATA AAA CTT TCA TTC TCA GTA GAT GAT GAA AAT AAA GAT AAT ATA CTT GGA TAT GAA ATA
Amino Acid: I   K   L   S   F   S   V   D   D   E   N   K   D   N   I   L   G   Y   E   I
Replace:   ATC     CTG TCC     TCC                         AAC         AAC ATC CTG GGC         ATC 781                                       810                                       840
original:  CGC AGA GAT GGA AAG TAT GTA GGA TTT ACT TCT AAT GAT AGC TTT GTT GAT ACT AAA TCT
Amino Acid: R   R   D   G   K   Y   V   G   F   T   S   N   D   S   F   V   D   T   K   S
Replace:       CGC     GGC             GGC                 AAC 841                                       870                                       900
original:  AAT TTA GAT GAG GAT GGT GTA TAT GTA GTA ACA CCA TAT GAT AGA AAG TTA AAT ACC TTA
Amino Acid: N   L   D   E   D   G   V   Y   V   V   T   P   Y   D   R   K   L   N   T   L
Replace:   AAC CTG                                 ACC CCG         CGC     CTG AAC     CTG 901                                       930                                       960
original:  AAT CCA ATA GAG GTA AAT GCA TTG CAA CCA ACT TTA TCT GTA AAC CCA GTG ATT ACA CTA
Amino Acid: N   P   I   E   V   N   A   L   Q   P   T   L   S   V   N   P   V   I   T   L
Replace:   AAC CCG ATC         AAC     CTG CCG     CTG                 CCG         ACC CTG 961
original:  GCT TTA GGT GAG GAG
Amino Acid: A   L   G   E   E
Replace:       CTG
```

FIG. 17B

```
           1                                                              30                                                             60
original:  ATG GTA AAA GTA GCT ATT AAC GGA TTT GGA AGA ATA GGA AGA TTA GCG TTA AGA TTA ATG
Amino Acid: M   V   K   V   A   I   N   G   F   G   R   I   G   R   L   A   L   R   L   M
Replace:                                            GGC     GGC CGC ATC GGC CGC CTG     CTG CGC CTG 61                                                             90                                                            120
original:  ATC GAC AAC CCT GAG TTT GAG GTT GTA GCA ATC AAC GAC TTA ACT GAT GCT AAG ACT TTA
Amino Acid: I   D   N   P   E   F   E   V   V   A   I   N   D   L   T   D   A   K   T   L
Replace:                                                                CTG                         CTG 121                                                            150                                                           180
original:  GCA CAC TTA TTC AAA TAC GAT TCA GCA CAA GGA AGA TTC AAT GGT GAA ATA GAA GTT AAA
Amino Acid: A   H   L   F   K   Y   D   S   A   Q   G   R   F   N   G   E   I   E   V   K
Replace:            CTG                                     GGC CGC                 ATC 181                                                            210                                                           240
original:  GAA GGA GCT TTC GTA GTT AAC GGA AAA GAA ATC AAA GTA ACT GCT AAA AGC AAC CCT GCT
Amino Acid: E   G   A   F   V   V   N   G   K   E   I   K   V   T   A   K   S   N   P   A
Replace:        GGC                         GGC 241                                                            270                                                           300
original:  GAA TTA CCA TGG GGA GAA TTA GGA GTA GAC GTA GTA TTA GAG TGT ACT GGA TTC TTC GCA
Amino Acid: E   L   P   W   G   E   L   G   V   D   V   V   L   E   C   T   G   F   F   A
Replace:        CTG             GGC         CTG GGC                 CTG                 GGC 301                                                            330                                                           360
original:  TCA AAA GAG AAA GCT TCA GCT CAC TTA ACT GCT GGT GCT AAA AAA GTT GTT ATC TCA GCT
Amino Acid: S   K   E   K   A   S   A   H   L   T   A   G   A   K   K   V   V   I   S   A
Replace:                                            CTG 361                                                            390                                                           420
original:  CCT GCT GGA AAC GAC CTA CCA ACA GTT GTT TAC AAC GTA AAC CAC GAT ATA TTA GAT GGA
Amino Acid: P   A   G   N   D   L   P   T   V   V   Y   N   V   N   H   D   I   L   D   G
Replace:            GGC         CTG                                                 ATC CTG     GGC 421                                                            450                                                           480
original:  AGC GAA GAT GTT ATC TCA GGT GCT TCA TGT ACT ACA AAC TGC TTA GCT CCA ATG GCT AAA
Amino Acid: S   E   D   V   I   S   G   A   S   C   T   T   N   C   L   A   P   M   A   K
Replace:                                                                    CTG 481                                                            510                                                           540
original:  GCT TTA AAT GAT AAC TTC GGA TTA AAC AAA GGT TTC ATG ACT ACA ATC CAT GCT TAC ACT
Amino Acid: A   L   N   D   N   F   G   L   N   K   G   F   M   T   T   I   H   A   Y   T
Replace:        CTG                         GGC CTG 541                                                            570                                                           600
original:  AAT GAC CAA AAC ACT TTA GAT GCT CCA CAC AAA AAA GGA GAC TTA AGA AGA GCT AGA GCT
Amino Acid: N   D   Q   N   T   L   D   A   P   H   K   K   G   D   L   R   R   A   R   A
Replace:                            CTG                             GGC     CTG CGC CGC     CGC 601                                                            630                                                           660
original:  GCT GCT GCT AAC ATA GTT CCA AAC TCA ACT GGA GCT GCT AAA GCT ATC GGT TTA GTT ATC
Amino Acid: A   A   A   N   I   V   P   N   S   T   G   A   A   K   A   I   G   L   V   I
Replace:                    ATC                         GGC             GGC                 CTG 661                                                            690                                                           720
original:  CCA GAA TTA GCT GGT AAA TTA GAC GGA AAC GCT CAA AGA GTA CCT GTA ATA ACT GGT TCA
Amino Acid: P   E   L   A   G   K   L   D   G   N   A   Q   R   V   P   V   I   T   G   S
Replace:            CTG                 CTG         GGC             CGC             ATC
```

FIG. 18A

```
           721                                     750                                     780
original:  TTA ACT GAG TTA GTT TGT ACT TTA GAT AAA AAA GTA ACA GTA GAA GAA GTA AAC GCT GCT
Amino Acid: L   T   E   L   V   C   T   L   D   K   K   V   T   V   E   E   V   N   A   A
Replace:   CTG         CTG             CTG 781                                     810                                     840
original:  ATG AAA GCT GCT TCA AAC GAA TCA TTC GGA TAC ACT GAA GAT CCA ATA GTA TCA TCA GAC
Amino Acid: M   K   A   A   S   N   E   S   F   G   Y   T   E   D   P   I   V   S   S   D
Replace:                                           GGC                     ATC 841                                     870                                     900
original:  GTT ATC GGA ATA AGC TTC GGA TCA TTA TTC GAT GCT ACT CAA ACA AAA ATA ATG GAA GTT
Amino Acid: V   I   G   I   S   F   G   S   L   F   D   A   T   Q   T   K   I   M   E   V
Replace:           GGC ATC             GGC     CTG                         ATC 901                                     930                                     960
original:  GAC GGA CAA CAA TTA GTT AAA GTT GCT TCA TGG TAT GAC AAC GAA GCT TCA TAC ACT AAC
Amino Acid: D   G   Q   Q   L   V   K   V   A   S   W   Y   D   N   E   A   S   Y   T   N
Replace:       GGC         CTG 961                                     990                                    1020
original:  CAA TTA ATC AGA ACT TTA AAA TGC TTA GTT TCT AAG TAA
Amino Acid: Q   L   I   R   T   L   K   C   L   V   S   K   -
Replace:       CTG     CGC     CTG             CTG
```

FIG. 18B

```
              1                                                   30                                                  60
original:     ATG GCA TTA GTT AAC GCA AAA GAA ATG TTA AAT AAA GCA AGA GAA GGA AAA TAC GCT GTT
Amino Acid:    M   A   L   V   N   A   K   E   M   L   N   K   A   R   E   G   K   Y   A   V
Replace:              CTG                         CTG                 CGC         GGC 61                                                  90                                                 120
original:     GGT CAA TTC AAC ATA AAC AAC TTA GAA TGG ACA AAA GCT ATA TTA TTA ACT GCT CAA GAA
Amino Acid:    G   Q   F   N   I   N   N   L   E   W   T   K   A   I   L   L   T   A   Q   E
Replace:                      ATC             CTG                     ATC CTG CTG 121                                                 150                                                180
original:     AAT AAC TCA CCA GTT ATA TTA GGA GTA TCA GAA GGT GCT GCT AAA TAC ATG TGT GGA TTC
Amino Acid:    N   N   S   P   V   I   L   G   V   S   E   G   A   A   K   Y   M   C   G   F
Replace:                          ATC CTG GGC                                             GGC 181                                                 210                                                240
original:     AAA ACA ATA GTT GGA ATG GTT AAC GGA ATG TTA GAA GAA TTA AAA ATA ACT GTT CCT GTA
Amino Acid:    K   T   I   V   G   M   V   N   G   M   L   E   E   L   K   I   T   V   P   V
Replace:               ATC         GGC                 GGC CTG             CTG     ATC 241                                                 270                                                300
original:     GCA TTA CAC TTA GAT CAC GGT AGC TAC CAA GGA GCT ATA GAT GCT ATG GAT GCT GGA TTC
Amino Acid:    A   L   H   L   D   H   G   S   Y   Q   G   A   I   D   A   M   D   A   G   F
Replace:          CTG     CTG                             GGC ATC                         GGC 301                                                 330                                                360
original:     TCA TCA GTA ATG TTC GAT GGA TCA CAC TAC TCA ATC GAA GAA AAC ATA GTT AAA ACT AAA
Amino Acid:    S   S   V   M   F   D   G   S   H   Y   S   I   E   E   N   I   V   K   T   K
Replace:                              GGC                                 ATC 361                                                 390                                                420
original:     GAA ATA ATC AAC TTA GCT GCT GCT AAA AAC GTA TCA GTT GAA GCT GAA GTT GGA TCA ATC
Amino Acid:    E   I   I   N   L   A   A   A   K   N   V   S   V   E   A   E   V   G   S   I
Replace:          ATC         CTG                                                     GGC 421                                                 450                                                480
original:     GGT GGA GAA GAA GAC GGT GTT GTT GGA GCT GGT GAA ATC GCT GAT CCT GCT GAA TGT AAA
Amino Acid:    G   G   E   E   D   G   V   V   G   A   G   E   I   A   D   P   A   E   C   K
Replace:          GGC                         GGC 481                                                 510                                                540
original:     CAA ATC GCT GAA TTA GGA GTT ACT ATG TTA GCT GCT GGT ATC GGA AAC ATT CAC GGA AAA
Amino Acid:    Q   I   A   E   L   G   V   T   M   L   A   A   G   I   G   N   I   H   G   K
Replace:                          CTG GGC         CTG             GGC             GGC 541                                                 570                                                600
original:     TAC CCT GCA AAC TGG GCT GGA TTA AAC TTC GAA GCT TTA GCT AAC ATT AAA GCT GCT ACT
Amino Acid:    Y   P   A   N   W   A   G   L   N   F   E   A   L   A   N   I   K   A   A   T
Replace:                              GGC CTG                 CTG 601                                                 630                                                660
original:     GGA GAT ATG CCT TTA GTA TTA CAC GGT GGT ACT GGA ATC CCT TCA GAT ATG ATC GCA GAA
Amino Acid:    G   D   M   P   L   V   L   H   G   G   T   G   I   P   S   D   M   I   A   E
Replace:       GGC             CTG     CTG                         GGC 661                                                 690                                                720
original:     GCT ATA TCA TTA GGA GTA TCA AAA ATA AAT GTT AAT ACT GAG TGT CAA TTA TCA TTT GCT
Amino Acid:    A   I   S   L   G   V   S   K   I   N   V   N   T   E   C   Q   L   S   F   A
Replace:              ATC CTG GGC                 ATC                             CTG
```

FIG. 19A

```
           721                                 750                                     780
original:  GAA GCT ACT CGT AAA TAT ATA GAA GCT GGA AAA GAC TTA GAA GGA AAA GGA TTT GAC CCA
Amino Acid: E   A   T   R   K   Y   I   E   A   G   K   D   L   E   G   K   G   F   D   P
Replace:                            ATC         GGC         CTG     GGC     GGC 781                                 810                                     840
original:  AGA AAA TTA TTA AAT CCT GGA TTC GAA GCT ATA AAA GCT ACA GTT AAA GAA AAA ATG GAA
Amino Acid: R   K   L   L   N   P   G   F   E   A   I   K   A   T   V   K   E   K   M   E
Replace:   CGC     CTG CTG             GGC         ATC 841                                 870                     900
original:  TTA TTC GGT TCA GTA AAC AGA GCT TAA
Amino Acid: L   F   G   S   V   N   R   A   -
Replace:   CTG                     CGC
```

FIG. 19B

SEQUENCE LISTING

```
<160> NUMBER OF SEQ ID NOS: 32

<210> SEQ ID NO 1
<211> LENGTH: 32
<212> TYPE: DNA
<213> ORGANISM: Clostridium perfringens

<400> SEQUENCE: 1
cggaattcga tccatcagtt ggaaagaatg ta                                     32

<210> SEQ ID NO 2
<211> LENGTH: 37
<212> TYPE: DNA
<213> ORGANISM: Clostridium perfringens

<400> SEQUENCE: 2
ccgaagctta ttattttata ttataagttg aatttcc                                37

<210> SEQ ID NO 3
<211> LENGTH: 35
<212> TYPE: DNA
<213> ORGANISM: Clostridium perfringens

<400> SEQUENCE: 3
agtttaacaa tttagagtgg gtaaggttag atgtg                                  35

<210> SEQ ID NO 4
<211> LENGTH: 33
<212> TYPE: DNA
<213> ORGANISM: Clostridium perfringens

<400> SEQUENCE: 4
```

```
gccagctcct aggaatcctg aaattatatc tac                                    33
```

<210> SEQ ID NO 5
<211> LENGTH: 84
<212> TYPE: DNA
<213> ORGANISM: Escherichia coli

<400> SEQUENCE: 5

```
aaatgagctg ttgacaatta atcatccggc tcgtataatg tgtggaattg tgagcggata      60
acaatttcac acaggaaaca gacc                                             84
```

<210> SEQ ID NO 6
<211> LENGTH: 147
<212> TYPE: DNA
<213> ORGANISM: Escherichia coli

<400> SEQUENCE: 6

```
atgagtattc aacatttccg tgtcgccctt attccctttt ttgcggcatt ttgccttcct      60 gttttgctc acccagaaac gctggtgaaa gtaaaagatg ctgaagaatt cgcaattccc     120
ggggatccgt cgacctgcag ccaagct                                         147
```

<210> SEQ ID NO 7
<211> LENGTH: 35
<212> TYPE: PRT
<213> ORGANISM: Escherichia coli

<400> SEQUENCE: 7

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu
        35

<210> SEQ ID NO 8
<211> LENGTH: 66
<212> TYPE: DNA
<213> ORGANISM: Escherichia coli

<400> SEQUENCE: 8

```
gcaactatgg atgaacgaaa tagacagatc gctgagatag gtgcctcact gattaagcat      60
tggtaa                                                                 66
```

<210> SEQ ID NO 9
<211> LENGTH: 21
<212> TYPE: PRT
<213> ORGANISM: Escherichia coli

<400> SEQUENCE: 9

Ala Thr Met Asp Glu Arg Asn Arg Gln Ile Ala Glu Ile Gly Ala Ser
1               5                   10                  15

Leu Ile Lys His Trp
            20

<210> SEQ ID NO 10
<211> LENGTH: 202
<212> TYPE: DNA
<213> ORGANISM: Escherichia coli

<400> SEQUENCE: 10

```
aaaaaatatt ctcaacataa aaaactttgt gtaatacttg taacgctaca tggagattaa      60
ctcaatctag ctagagaggc tttacacttt atgcttccgg ctcgtataat gtgtggaatt    120
gtgagcggat aacaatttca cacaggaaac agctatgacc atgattacgg attcactgga    180
actctagata acgagggcaa aa                                              202
```

```
<210> SEQ ID NO 11
<211> LENGTH: 71
<212> TYPE: DNA
<213> ORGANISM: Escherichia coli

<400> SEQUENCE: 11
atgaaaaaga cagctatcgc gattgcagtg gcactggctg gtttcgctac cgtagcgcag     60
gccgcgaatt c                                                         71
```

```
<210> SEQ ID NO 12
<211> LENGTH: 22
<212> TYPE: PRT
<213> ORGANISM: Escherichia coli

<400> SEQUENCE: 12
```

Met Lys Lys Thr Ala Ile Ala Ile Ala Val Ala Leu Ala Gly Phe Ala
1               5                   10                  15

Thr Val Ala Gln Ala Ile
            20

```
<210> SEQ ID NO 13
<211> LENGTH: 366
<212> TYPE: PRT
<213> ORGANISM: Clostridium perfringens

<400> SEQUENCE: 13
```

Trp Asp Gly Lys Ile Asp Gly Thr Gly Thr His Ala Met Ile Val Leu
1 5 10 15

Lys Gly Val Ser Leu Glu Asn Asp Leu Ser Lys Asn Glu Pro Glu Ser
20 25 30

Val Arg Lys Asn Leu Glu Ile Leu Lys Glu Asn Met His Glu Leu Gln
35 40 45

Leu Gly Ser Thr Tyr Pro Lys Tyr Lys Asp Asn Ala Tyr Asp Leu Tyr
50 55 60

Gln Asp His Phe Trp Asp Pro Asp Thr Asp Asn Asn Phe Ser Lys Asp
65 70 75 80

Asn Ser Trp Tyr Leu Ala Tyr Ser Ile Pro Asp Thr Gly Glu Ser Gln
85 90 95

Ile Arg Lys Phe Ser Ala Leu Ala Arg Tyr Glu Trp Gln Arg Gly Asn
100 105 110

Tyr Lys Gln Ala Thr Phe Leu Gly Glu Ala Met His Tyr Phe Gly Asp
115 120 125

Ile Asp Thr Pro Tyr His Pro Ala Asn Val Thr Ala Val Asp Ser Ala
130 135 140

Gly His Val Lys Phe Glu Thr Phe Ala Glu Glu Arg Lys Glu Gln Tyr
145 150 155 160

Lys Ile Asn Thr Ala Gly Cys Lys Thr Asn Glu Asp Phe Tyr Ala Asp
165 170 175

Ile Leu Lys Asn Lys Asp Phe Asn Ala Trp Ser Lys Glu Tyr Ala Arg
180 185 190

```
Gly Phe Ala Lys Thr Gly Lys Ser Ile Tyr Tyr Ser His Ala Ser Met
            195                 200                 205

Ser His Ser Trp Asp Asp Trp Asp Tyr Ala Ala Lys Val Thr Leu Ala
210                 215                 220

Asn Ser Gln Lys Gly Thr Ala Gly Tyr Ile Tyr Arg Phe Leu His Asp
225                 230                 235                 240

Val Ser Glu Gly Asn Asp Pro Ser Val Gly Lys Asn Val Lys Glu Leu
            245                 250                 255

Val Ala Tyr Ile Ser Thr Ser Gly Glu Lys Asp Ala Gly Thr Asp Asp
            260                 265                 270

Tyr Met Tyr Phe Gly Ile Lys Thr Lys Asp Gly Lys Thr Gln Glu Trp
        275                 280                 285

Glu Met Asp Asn Pro Gly Asn Asp Phe Met Thr Gly Ser Lys Asp Thr
290                 295                 300

Tyr Thr Phe Lys Leu Lys Asp Glu Asn Leu Lys Ile Asp Asp Ile Gln
305                 310                 315                 320

Asn Met Trp Ile Arg Lys Arg Lys Thr Ala Phe Pro Asp Ala Tyr Lys
                325                 330                 335

Pro Glu Asn Ile Lys Ile Ile Ala Asn Gly Lys Val Val Asp Lys Asp
            340                 345                 350

Ile Asn Glu Trp Ile Ser Arg Lys Ser Thr Tyr Asn Ile Lys
            355                 360                 365

<210> SEQ ID NO 14
<211> LENGTH: 367
<212> TYPE: PRT
<213> ORGANISM: Clostridium perfringens

<400> SEQUENCE: 14

Trp Asp Gly Lys Ile Asp Gly Thr Gly Thr His Ala Met Ile Val Thr
1               5                   10                  15

Gln Gly Val Ser Ile Leu Glu Asn Asp Leu Ser Lys Asn Glu Pro Glu
            20                  25                  30

Ser Val Arg Lys Asn Leu Glu Ile Leu Lys Glu Asn Met His Glu Leu
        35                  40                  45

Gln Leu Gly Ser Thr Tyr Pro Lys Tyr Lys Asp Asn Ala Tyr Asp Leu
    50                  55                  60

Tyr Gln Asp His Phe Trp Asp Pro Asp Thr Asp Asn Asn Phe Ser Lys
65                  70                  75                  80

Asp Asn Ser Trp Tyr Leu Ala Tyr Ser Ile Pro Asp Thr Gly Glu Ser
                85                  90                  95

Gln Ile Arg Lys Phe Ser Ala Leu Ala Arg Tyr Glu Trp Gln Arg Gly
            100                 105                 110

Asn Tyr Lys Gln Ala Thr Phe Leu Gly Glu Ala Met His Tyr Phe Gly
        115                 120                 125

Asp Ile Asp Thr Pro Tyr His Pro Ala Asn Val Thr Ala Val Asp Ser
    130                 135                 140

Ala Gly His Val Lys Phe Glu Thr Phe Ala Glu Glu Arg Lys Glu Gln
145                 150                 155                 160

Tyr Lys Ile Asn Thr Ala Gly Cys Lys Thr Asn Glu Ala Phe Tyr Thr
                165                 170                 175

Asp Ile Leu Lys Asn Lys Asp Phe Asn Ala Trp Ser Lys Glu Tyr Ala
            180                 185                 190

Arg Gly Phe Ala Lys Thr Gly Lys Ser Ile Tyr Tyr Ser His Ala Ser
        195                 200                 205
```

```
Met Ser His Ser Trp Asp Asp Trp Asp Tyr Ala Ala Lys Val Thr Leu
    210                 215                 220
Ala Asn Ser Gln Lys Gly Thr Ala Gly Tyr Ile Tyr Arg Phe Leu His
225                 230                 235                 240
Asp Val Ser Glu Gly Asn Asp Pro Ser Val Gly Lys Asn Val Lys Glu
                245                 250                 255
Leu Val Ala Tyr Ile Ser Thr Ser Gly Glu Lys Asp Ala Gly Thr Asp
                260                 265                 270
Asp Tyr Met Tyr Phe Gly Ile Lys Thr Lys Asp Gly Lys Thr Gln Glu
            275                 280                 285
Trp Glu Met Asp Asn Pro Gly Asn Asp Phe Met Thr Gly Ser Lys Asp
    290                 295                 300
Thr Tyr Thr Phe Lys Leu Lys Asp Glu Asn Leu Lys Ile Asp Asp Ile
305                 310                 315                 320
Gln Asn Met Trp Ile Arg Lys Arg Lys Thr Ala Phe Ser Asp Ala Tyr
                325                 330                 335
Lys Pro Glu Asn Ile Lys Ile Ile Ala Asn Gly Lys Val Val Asp Lys
                340                 345                 350
Asp Ile Asn Glu Trp Ile Ser Gly Asn Ser Thr Tyr Asn Ile Lys
            355                 360                 365

<210> SEQ ID NO 15
<211> LENGTH: 387
<212> TYPE: DNA
<213> ORGANISM: Clostridium perfringens

<400> SEQUENCE: 15
gaattcgacc cgtccgtggg caacaacgtg aaagaactgg tggcttacat ctccactagc      60
ggcgaaaaag acgctggcac cgacgactac atgtatttcg gcatcaaaac caaggacggc     120
aaaactcaag aatgggaaat ggacaacccg ggcaacgact tcatggctgg cagcaaagac     180
acttatactt tcaaattaaa agacgaaaac ctgaaaattg acgacatcca aaacatgtgg     240
attcgcaaac gtaaatatac cgcattcccg gacgcttata gccggaaaaa catcaaggtg     300
atcgcaaacg gcaaagtggt agtggacaag gacatcaacg agtggatttc cggcaactcc     360
acttataaca tcaaataata aaagctt                                         387

<210> SEQ ID NO 16
<211> LENGTH: 387
<212> TYPE: DNA
<213> ORGANISM: Clostridium perfringens

<400> SEQUENCE: 16
cttaagctgg gcaggcaccc gttgttgcac tttcttgacc accgaatgta gaggtgatcg      60 ccgcttttc tgcgaccgtg gctgctgatg tacataaagc cgtagttttg gttcctgccg      120
ttttgagttc ttacccttta cctgttgggc ccgttgctga agtaccgacc gtcgtttctg     180
tgaatatgaa agtttaattt tctgcttttg gacttttaac tgctgtaggt tttgtacacc     240
taagcgtttg catttatatg gcgtaagggc ctgcgaatat tcggccttt gtagttccac     300 tagcgtttgc cgtttcacca tcacctgttc ctgtagttgc tcacctaaag gccgttgagg     360
tgaatattgt agtttattat tttcgaa                                         387

<210> SEQ ID NO 17
<211> LENGTH: 123
<212> TYPE: PRT
```

<213> ORGANISM: Clostridium perfringens

<400> SEQUENCE: 17

Asp Pro Ser Val Gly Asn Asn Val Lys Glu Leu Val Ala Tyr Ile Ser
1               5                   10                  15
Thr Ser Gly Glu Lys Asp Ala Gly Thr Asp Asp Tyr Met Tyr Phe Gly
            20                  25                  30
Ile Lys Thr Lys Asp Gly Lys Thr Gln Glu Trp Glu Met Asp Asn Pro
        35                  40                  45
Gly Asn Asp Phe Met Ala Gly Ser Lys Asp Tyr Thr Phe Lys Leu
    50                  55                  60
Lys Asp Glu Asn Leu Lys Ile Asp Asp Ile Gln Asn Met Trp Ile Arg
65                  70                  75                  80
Lys Arg Lys Tyr Thr Ala Phe Pro Asp Ala Tyr Lys Pro Glu Asn Ile
                85                  90                  95
Lys Val Ile Ala Asn Gly Lys Val Val Val Asp Lys Asp Ile Asn Glu
            100                 105                 110
Trp Ile Ser Gly Asn Ser Thr Tyr Asn Ile Lys
        115                 120

<210> SEQ ID NO 18
<211> LENGTH: 891
<212> TYPE: DNA
<213> ORGANISM: Clostridium perfringens

<400> SEQUENCE: 18

```
gaattcagcg aactgaacga catcaacaaa attgagctga aaaacctgag cggcgaaatc    60
atcaaagaaa acggcaagga agctattaaa tatacttcca gcgacaccgc ttcccataaa   120
ggctggaagg caactctgag cggcaccttc attgagacc cgcattccga caagaaaact   180
gctctgctga acctggaagg ctttatcccg tccgacaaac agattttcgg ctctaaatat   240
tacggcaaaa tgaaatggcc ggaaacttat cgcattaatg tgaaaagcgc tgacgtgaac   300
aataacatca aatcgcaaa ctccattccg aaaaatacta tcgacaaaaa agacgtgtcc   360
aattccattg ctattccat cggcggtaac atctccgtgg aaggcaaaac tgctggcgct   420
ggcatcaacg cttcctataa cgtccaaaac actatcagct atgaacaacc ggacttccgc   480
accattcaac gcaaagacga tgcaaacctg gcatcctggg acatcaaatt cgttgagact   540
aaggacggct ataacatcga ctcctatcat gctatttatg caaccaact gttcatgaaa   600
tcccgcctgt ataacaatgg cgacaaaaac ttcaccgacg atcgcgacct gtccaccctg   660
atttccggcg gcttctcccc gaacatggct ctggcactga ccgcacctaa aaatgctaaa   720
gaatccgtga tcatcgtgga atatcaacgc ttcgacaacg actatattct gaattgggaa   780
actactcaat ggcgcggcac caacaaactt tcctcaacca gcgaatataa cgaatttatg   840
ttcaaaatca ctggcaagaa ccataaaatc gaatattatc tgtaaaagct t             891
```

<210> SEQ ID NO 19
<211> LENGTH: 891
<212> TYPE: DNA
<213> ORGANISM: Clostridium perfringens

<400> SEQUENCE: 19

```
cttaagtcgc ttgacttgct gtagttgttt taactcgact ttttggactc gccgctttag    60
tagtttcttt tgccgttcct tcgataattt atatgaaggt cgctgtggcg aagggtattt   120
ccgaccttcc gttgagactc gccgtggaag taacttctgg gcgtaaggct gttcttttga   180
```

```
cgagacgact tggaccttcc gaaatagggc aggctgtttg tctaaaagcc gagatttata    240
atgccgtttt actttaccgg cctttgaata gcgtaattac acttttcgcg actgcacttg    300
ttattgtagt tttagcgttt gaggtaaggc ttttatgat agctgttttt tctgcacagg     360
ttaaggtaac cgataaggta gccgccattg tagaggcacc ttccgttttg acgaccgcga    420
ccgtagttgc gaaggatatt gcaggttttg tgatagtcga tacttgttgg cctgaaggcg    480
tggtaagttg cgtttctgct acgtttggac cgtaggaccc tgtagtttaa gcaactctga    540
ttcctgccga tattgtagct gaggatagta cgataaatac cgttggttga caagtacttt    600
agggcggaca tattgttacc gctgtttttg aagtggctgc tagcgctgga caggtgggac    660
taaaggccgc cgaagagggg cttgtaccga gaccgtgact ggcgtggatt tttacgattt    720
cttaggcact agtagcacct tatagttgcg aagctgttgc tgatataaga cttaaccctt    780
tgatgagtta ccgcgccgtg gttgtttgaa aggagttggt cgcttatatt gcttaaatac    840 aagtttagt tgaccgttct ggtattttag cttataatag acattttcga a             891
```

<210> SEQ ID NO 20
<211> LENGTH: 292
<212> TYPE: PRT
<213> ORGANISM: Clostridium perfringens

<400> SEQUENCE: 20

```
Ser Glu Leu Asn Asp Ile Asn Lys Ile Glu Leu Lys Asn Leu Ser Gly
1               5                   10                  15

Glu Ile Ile Lys Glu Asn Gly Lys Glu Ala Ile Lys Tyr Thr Ser Ser
            20                  25                  30

Asp Thr Ala Ser His Lys Gly Trp Lys Ala Thr Leu Ser Gly Thr Phe
        35                  40                  45

Ile Glu Asp Pro His Ser Asp Lys Lys Thr Ala Leu Leu Asn Leu Glu
    50                  55                  60

Gly Phe Ile Pro Ser Asp Lys Gln Ile Phe Gly Ser Lys Tyr Tyr Gly
65                  70                  75                  80

Lys Met Lys Trp Pro Glu Thr Tyr Arg Ile Asn Val Lys Ser Ala Asp
                85                  90                  95

Val Asn Asn Asn Ile Lys Ile Ala Asn Ser Ile Pro Lys Asn Thr Ile
            100                 105                 110

Asp Lys Lys Asp Val Ser Asn Ser Ile Gly Tyr Ser Ile Gly Gly Asn
        115                 120                 125

Ile Ser Val Glu Gly Lys Thr Ala Gly Ala Gly Ile Asn Ala Ser Tyr
    130                 135                 140

Asn Val Gln Asn Thr Ile Ser Tyr Glu Gln Pro Asp Phe Arg Thr Ile
145                 150                 155                 160

Gln Arg Lys Asp Asp Ala Asn Leu Ala Ser Trp Asp Ile Lys Phe Val
                165                 170                 175

Glu Thr Lys Asp Gly Tyr Asn Ile Asp Ser Tyr His Ala Ile Tyr Gly
            180                 185                 190

Asn Gln Leu Phe Met Lys Ser Arg Leu Tyr Asn Asn Gly Asp Lys Asn
        195                 200                 205

Phe Thr Asp Asp Arg Asp Leu Ser Thr Leu Ile Ser Gly Gly Phe Ser
    210                 215                 220

Pro Asn Met Ala Leu Ala Leu Thr Ala Pro Lys Asn Ala Lys Glu Ser
225                 230                 235                 240

Val Ile Ile Val Glu Tyr Gln Arg Phe Asp Asn Asp Tyr Ile Leu Asn
```

```
                 245                 250                 255
Trp Glu Thr Thr Gln Trp Arg Gly Thr Asn Lys Leu Ser Ser Thr Ser
            260                 265                 270

Glu Tyr Asn Glu Phe Met Phe Lys Ile Asn Trp Gln Asp His Lys Ile
        275                 280                 285

Glu Tyr Tyr Leu
    290

<210> SEQ ID NO 21
<211> LENGTH: 1680
<212> TYPE: DNA
<213> ORGANISM: Clostridium perfringens

<400> SEQUENCE: 21
acattagaac cagttggaga tatagatact actccagaag gaactaaagc ttgtaagttc      60
tggggattag gatcagacgg aacagttgga gctaacaaga gtgctatcaa aatcatcgga    120
gaccatactg acatgtatgc tcaaggatac tttgcatatg actctaaaaa atcaggtggg    180
gttacaattt ctcacttaag attcggtaaa caaccaataa aatcacctta cttaataaac    240
aaagctgatt tcgttgcttg tcataaccaa tcatatgtta acaaatactt cgttttagat    300
ggattaaaga aaacggaac attcttatta aacactatct ggactccaga agaagttgct    360
gaacatttac cagcaagcta taagagattc ttagctgaaa acaacattaa gttctacact    420
ttaaatgctg ttaagatagc tcaagaagtt ggtttaggtg aagaatcaa catgatcatg    480
caatcagcat tcttcaaact agctaacata ataccagtag aagacgcagt taaatactta    540
aaagacgctg ttgtaacttc atacggtaaa aaaggtgaaa aagttgttaa catgaaccac    600
gctgctatag acaaaggaat cgacgctatc gttgaaatca ctgttccagc tgagtgggct    660
aacgctaaag atgaagttgt tgaagctaaa gaagttccag cattcatcaa aaacattgtt    720
gaaccaatga acagattaga aggagataaa cttcctgtat cagcattcaa cggaatggaa    780
gatggtactt tcgaaccagg tactgctgca tacgaaaaga gggaatcgg tataaacata    840
ccagaatgga tagcagacaa ctgtatccaa tgtaaccaat gtgcttacgt ttgtcctcat    900
gctacaataa gaccattctt attaactgag gaagaagcta aaaatgctcc tgcttcaact    960
aagttagttg ctgctaaagc attaaaaact gaagagccaa tgcaattcac tatggctgta   1020
agtactttag actgtactgg atgtggaaac tgtgctcaag tttgtcctgc taaggaaaaa   1080
gctttagtta tgaaaccaca acatactcaa gaagatcaaa tagaagcttg ggattactgt   1140
gtaaatgatg ttgtacctaa gaaaaaccca atgaacaaaa acacagttaa aggtagccaa   1200
ttcgagcaac cattattcga gttctcagga gcttgtgctg gatgtggaga aactccatat   1260
gctaaactta taactcaatt attcggagat agaatgatga tagctaacgc tactggatgt   1320
tcatcaatct ggggtggatc agctcccttca actccataca caactaaccaa caatggtcat   1380
ggaccagctt gggctaactc attattcgag gacaacgctg aattcggatt aggtatgttc   1440
ttaggagtta aagctataag agaaagatta gttgatcttg ctggaaaagc aattgaagct   1500
ggtgttaaac cagaagctaa agaagcttta gaagcttgga tagctgaagt tgacaacgga   1560
gaaggaacta gagatagagc tgacgctgtt gtagctgcat tacaaggtga aactaacgag   1620
ttcgctaaag aaatattaaa agaccaagac tacttagcta agagatcaca atggatcttc   1680

<210> SEQ ID NO 22
<211> LENGTH: 560
<212> TYPE: PRT
```

<213> ORGANISM: Clostridium perfringens

<400> SEQUENCE: 22

Thr Leu Glu Pro Val Gly Asp Ile Asp Thr Thr Pro Glu Gly Thr Lys
1               5                   10                  15

Ala Cys Lys Phe Trp Gly Leu Gly Ser Asp Gly Thr Val Gly Ala Asn
            20                  25                  30

Lys Ser Ala Ile Lys Ile Ile Gly Asp His Thr Asp Met Tyr Ala Gln
        35                  40                  45

Gly Tyr Phe Ala Tyr Asp Ser Lys Ser Gly Gly Val Thr Ile Ser
    50                  55                  60

His Leu Arg Phe Gly Lys Gln Pro Ile Lys Ser Pro Tyr Leu Ile Asn
65                  70                  75                  80

Lys Ala Asp Phe Val Ala Cys His Asn Gln Ser Tyr Val Asn Lys Tyr
                85                  90                  95

Phe Val Leu Asp Gly Leu Lys Lys Asn Gly Thr Phe Leu Leu Asn Thr
            100                 105                 110

Ile Trp Thr Pro Glu Glu Val Ala Glu His Leu Pro Ala Ser Tyr Lys
        115                 120                 125

Arg Phe Leu Ala Glu Asn Asn Ile Lys Phe Tyr Thr Leu Asn Ala Val
    130                 135                 140

Lys Ile Ala Gln Glu Val Gly Leu Gly Gly Arg Ile Asn Met Ile Met
145                 150                 155                 160

Gln Ser Ala Phe Phe Lys Leu Ala Asn Ile Ile Pro Val Glu Asp Ala
                165                 170                 175

Val Lys Tyr Leu Lys Asp Ala Val Val Thr Ser Tyr Gly Lys Lys Gly
            180                 185                 190

Glu Lys Val Val Asn Met Asn His Ala Ala Ile Asp Lys Gly Ile Asp
        195                 200                 205

Ala Ile Val Glu Ile Thr Val Pro Ala Glu Trp Ala Asn Ala Lys Asp
    210                 215                 220

Glu Val Val Glu Ala Lys Glu Val Pro Ala Phe Ile Lys Asn Ile Val
225                 230                 235                 240

Glu Pro Met Asn Arg Leu Glu Gly Asp Lys Leu Pro Val Ser Ala Phe
                245                 250                 255

Asn Gly Met Glu Asp Gly Thr Phe Glu Pro Gly Thr Ala Ala Tyr Glu
            260                 265                 270

Lys Arg Gly Ile Gly Ile Asn Ile Pro Glu Trp Ile Ala Asp Asn Cys
        275                 280                 285

Ile Gln Cys Asn Gln Cys Ala Tyr Val Cys Pro His Ala Thr Ile Arg
    290                 295                 300

Pro Phe Leu Leu Thr Glu Glu Ala Lys Asn Ala Pro Ala Ser Thr
305                 310                 315                 320

Lys Leu Val Ala Ala Lys Ala Leu Lys Thr Glu Glu Pro Met Gln Phe
                325                 330                 335

Thr Met Ala Val Ser Thr Leu Asp Cys Thr Gly Cys Gly Asn Cys Ala
            340                 345                 350

Gln Val Cys Pro Ala Lys Glu Lys Ala Leu Val Met Lys Pro Gln His
        355                 360                 365

Thr Gln Glu Asp Gln Ile Glu Ala Trp Asp Tyr Cys Val Asn Asp Val
    370                 375                 380

Val Pro Lys Lys Asn Pro Met Asn Lys Asn Thr Val Lys Gly Ser Gln
385                 390                 395                 400

```
Phe Glu Gln Pro Leu Phe Glu Phe Ser Gly Ala Cys Ala Gly Cys Gly
                405                 410                 415

Glu Thr Pro Tyr Ala Lys Leu Ile Thr Gln Leu Phe Gly Asp Arg Met
            420                 425                 430

Met Ile Ala Asn Ala Thr Gly Cys Ser Ser Ile Trp Gly Gly Ser Ala
        435                 440                 445

Pro Ser Thr Pro Tyr Thr Thr Asn His Asn Gly His Gly Pro Ala Trp
    450                 455                 460

Ala Asn Ser Leu Phe Glu Asp Asn Ala Glu Phe Gly Leu Gly Met Phe
465                 470                 475                 480

Leu Gly Val Lys Ala Ile Arg Glu Arg Leu Val Asp Leu Ala Gly Lys
                485                 490                 495

Ala Ile Glu Ala Gly Val Lys Pro Glu Ala Lys Glu Ala Leu Glu Ala
            500                 505                 510

Trp Ile Ala Glu Val Asp Asn Gly Glu Gly Thr Arg Asp Arg Ala Asp
        515                 520                 525

Ala Val Val Ala Ala Leu Gln Gly Glu Thr Asn Glu Phe Ala Lys Glu
    530                 535                 540

Ile Leu Lys Asp Gln Asp Tyr Leu Ala Lys Arg Ser Gln Trp Ile Phe
545                 550                 555                 560

<210> SEQ ID NO 23
<211> LENGTH: 1680
<212> TYPE: DNA
<213> ORGANISM: Clostridium perfringens

<400> SEQUENCE: 23
acactggaac cagttggcga tatcgatact actccagaag gcactaaagc ttgtaagttc      60
tggggcctgg gctcagacgg cacagttggc gctaacaaga gtgctatcaa atcatcggc     120
gaccatactg acatgtatgc tcaaggctac tttgcatatg actctaaaaa atcaggtggg     180
gttacaattt ctcacctgcg cttcggtaaa caaccaatca aatcacctta cctgatcaac     240
aaagctgatt tcgttgcttg tcataaccaa tcatatgtta caaatacttt cgttctggat     300
ggcctgaaga aaaacggcac attcctgctg aacactatct ggactccaga agaagttgct     360
gaacatctgc cagcaagcta taagcgcttc ctggctgaaa caacattaa gttctacact      420
ctgaatgctg ttaagatcgc tcaagaagtt ggtctgggtg ccgcatcaa catgatcatg      480
caatcagcat tcttcaaact ggctaacatc atcccagtag aagacgcagt taaatacctg     540
aaagacgctg ttgtaacttc atacggtaaa aaaggtgaaa agttgttaa catgaaccac      600
gctgctatcg acaaaggcat cgacgctatc gttgaaatca ctgttccagc tgagtgggct     660
aacgctaaag atgaagttgt tgaagctaaa gaagttccag cattcatcaa aaacattgtt     720
gaaccaatga accgcctgga aggcgataaa cttcctgtat cagcattcaa cggcatggaa     780
gatggtactt tcgaaccagg tactgctgca tacgaaaagc gcggcatcgg tatcaacatc     840
ccagaatgga tcgcagacaa ctgtatccaa tgtaaccaat gtgcttacgt tgtcctcat      900
gctacaatcc gcccattcct gctgactgag gagaagcta aaaatgctcc tgcttcaact      960
aagctggttg ctgctaaagc actgaaaact gaagagccaa tgcaattcac tatggctgta    1020
agtactctgg actgtactgg ctgtggcaac tgtgctcaag tttgtcctgc taaggaaaaa    1080
gctctggtta tgaaaccaca acatactcaa gaagatcaaa tcgaagcttg ggattactgt    1140
gtaaatgatg ttgtacctaa gaaaaaccca atgaacaaaa acacagttaa aggtagccaa    1200
ttcgagcaac cactgttcga gttctcaggc gcttgtgctg gctgtggcga aactccatat    1260
```

```
gctaaactta tcactcaact gttcggcgat cgcatgatga tcgctaacgc tactggctgt    1320
tcatcaatct ggggtggctc agctccttca actccataca caactaacca caatggtcat    1380
ggcccagctt gggctaactc actgttcgag acaacgctg aattcggcct gggtatgttc     1440
ctgggcgtta aagctatccg cgaacgcctg gttgatcttg ctggcaaagc aattgaagct    1500
ggtgttaaac cagaagctaa agaagctctg gaagcttgga tcgctgaagt tgacaacggc    1560
gaaggcactc gcgatcgcgc tgacgctgtt gtagctgcac tgcaaggtga actaacgag    1620 ttcgctaaag aaatcctgaa agaccaagac tacctggcta agcgctcaca atggatcttc   1680
```

<210> SEQ ID NO 24
<211> LENGTH: 975
<212> TYPE: DNA
<213> ORGANISM: Clostridium perfringens

<400> SEQUENCE: 24

```
ttctggggat tgataactc aaaagatgtt aattcagatt ttaattttag aataatgcct       60
atggttaaaa accttagtgg tggagcattc atgaatgctg gaaatggtgt tataggtata     120
agacctggaa atcaggatgc aatacttgca gctaataaag gatggggtgt tgctcatgaa     180
cttggacata actttgatac aggcggaaga accatagtag aagtaacaaa taatatgatg     240
ccattattct ttgagtctaa atataaaact aaaacaagaa taactgacca aaacatatgg     300
gaaaacaata cttaccctaa agttggctta gatgattatt ctaataatga gttatataat     360
aaggctgata gtactcattt agctcagtta gcgccattat ggcaattata tttatatgat     420
aatactttct atggaaagtt tgaaagacag tttagagaaa gagattttgg aaataaaaat     480
agagaagata tatataaatc ttgggttgtg gcagcgtcag atgctatgga gttagattta     540
actgagttct ttgcaagaca tggtattcgt gttgatgata aggttaagga ggatttagct     600
aagtatccaa agcctgataa aaagatctat tacttaaatg atttagcaat gaattataaa     660
ggtgatggat ttacggataa tgcaaaggta tctgtaagta caagtggttc aaatggtaat     720
ataaaacttt cattctcagt agatgatgaa aataaagata atatacttgg atatgaaata     780
cgcagagatg gaaagtatgt aggatttact tctaatgata gctttgttga tactaaatct     840
aatttagatg aggatggtgt atatgtagta acaccatatg atagaaagtt aaataccttc    900
aatccaatag aggtaaatgc attgcaacca actttatctg taaacccagt gattacacta    960
gctttaggtg aggag                                                       975
```

<210> SEQ ID NO 25
<211> LENGTH: 325
<212> TYPE: PRT
<213> ORGANISM: Clostridium perfringens

<400> SEQUENCE: 25

```
Phe Trp Gly Phe Asp Asn Ser Lys Asp Val Asn Ser Asp Phe Asn Phe
1               5                   10                  15

Arg Ile Met Pro Met Val Lys Asn Leu Ser Gly Gly Ala Phe Met Asn
            20                  25                  30

Ala Gly Asn Gly Val Ile Gly Ile Arg Pro Gly Asn Gln Asp Ala Ile
        35                  40                  45

Leu Ala Ala Asn Lys Gly Trp Gly Val Ala His Glu Leu Gly His Asn
    50                  55                  60

Phe Asp Thr Gly Gly Arg Thr Ile Val Glu Val Thr Asn Asn Met Met
65                  70                  75                  80
```

```
Pro Leu Phe Phe Glu Ser Lys Tyr Lys Thr Lys Thr Arg Ile Thr Asp
                 85                  90                  95

Gln Asn Ile Trp Glu Asn Asn Thr Tyr Pro Lys Val Gly Leu Asp Asp
            100                 105                 110

Tyr Ser Asn Asn Glu Leu Tyr Asn Lys Ala Asp Ser Thr His Leu Ala
        115                 120                 125

Gln Leu Ala Pro Leu Trp Gln Leu Tyr Leu Tyr Asp Asn Thr Phe Tyr
    130                 135                 140

Gly Lys Phe Glu Arg Gln Phe Arg Glu Arg Asp Phe Gly Asn Lys Asn
145                 150                 155                 160

Arg Glu Asp Ile Tyr Lys Ser Trp Val Val Ala Ser Asp Ala Met
                165                 170                 175

Glu Leu Asp Leu Thr Glu Phe Phe Ala Arg His Gly Ile Arg Val Asp
            180                 185                 190

Asp Lys Val Lys Glu Asp Leu Ala Lys Tyr Pro Lys Pro Asp Lys Lys
        195                 200                 205

Ile Tyr Tyr Leu Asn Asp Leu Ala Met Asn Tyr Lys Gly Asp Gly Phe
    210                 215                 220

Thr Asp Asn Ala Lys Val Ser Val Ser Thr Ser Gly Ser Asn Gly Asn
225                 230                 235                 240

Ile Lys Leu Ser Phe Ser Val Asp Asp Glu Asn Lys Asp Asn Ile Leu
                245                 250                 255

Gly Tyr Glu Ile Arg Arg Asp Gly Lys Tyr Val Gly Phe Thr Ser Asn
            260                 265                 270

Asp Ser Phe Val Asp Thr Lys Ser Asn Leu Asp Glu Asp Gly Val Tyr
        275                 280                 285

Val Val Thr Pro Tyr Asp Arg Lys Leu Asn Thr Leu Asn Pro Ile Glu
    290                 295                 300

Val Asn Ala Leu Gln Pro Thr Leu Ser Val Asn Pro Val Ile Thr Leu
305                 310                 315                 320

Ala Leu Gly Glu Glu
                325

<210> SEQ ID NO 26
<211> LENGTH: 975
<212> TYPE: DNA
<213> ORGANISM: Clostridium perfringens

<400> SEQUENCE: 26
ttctggggct tgataactc caaagatgtt aactccgatt ttaactttcg catcatgccg      60
atggttaaaa acctgtccgg tggcgcattc atgaacgctg caacggtgt tatcggtatc    120 cgcccgggca accaggatgc aatcctggca gctaacaaag ctggggtgt tgctcatgaa    180 ctgggccata actttgatac cggcggccgc accatcgtag aagtaaccaa caacatgatg    240
ccgctgttct tgagtctaa atataaaact aaacccgca tcactgacca aaacatctgg      300
gaaaacaaca cttacccgaa agttggcctg atgattatt ctaacaacga gctgtataac    360
aaggctgatt ccactcatct ggctcagctg gcgccgctgt ggcaactgta tctgtatgat    420
aacactttct atggcaagtt tgaacgccag tttcgcgaac gcgattttgg caacaaaaac    480
cgcgaagata tctataaatc ttgggttgtg gcagcgtccg atgctatgga gctggatctg    540
actgagttct tgcacgcca tggtattcgt gttgatgata aggttaagga ggatctggct    600
aagtatccga agccggataa aaagatctat tacctgaacg atctggcaat gaactataaa    660
```

```
ggtgatggct ttaccgataa cgcaaaggta tctgtatcca cctccggttc caacggtaac    720
atcaaactgt ccttctccgt agatgatgaa aacaaagata catcctgggg ctatgaaatc    780
cgccgcgatg gcaagtatgt aggctttact tctaacgata gctttgttga tactaaatct    840
aacctggatg aggatggtgt atatgtagta accccgtatg atcgcaagct gaacaccctg    900
aacccgatcg aggtaaacgc actgcaaccg actctgtctg taaacccggt gattaccctg    960
gctctgggtg aggag                                                    975
```

<210> SEQ ID NO 27
<211> LENGTH: 999
<212> TYPE: DNA
<213> ORGANISM: Clostridium perfringens
<400> SEQUENCE: 27

```
atggtaaaag tagctattaa cggatttgga agaataggaa gattagcgtt aagattaatg     60
atcgacaacc ctgagtttga ggttgtagca atcaacgact taactgatgc taagacttta    120
gcacacttat tcaaatacga ttcagcacaa ggaagattca atggtgaaat agaagttaaa    180
gaaggagctt tcgtagttaa cggaaaagaa atcaaagtaa ctgctaaaag caaccctgct    240
gaattaccat ggggagaatt aggagtagac gtagtattag agtgtactgg attcttcgca    300
tcaaaagaga aagcttcagc tcacttaact gctggtgcta aaaagttgt tatctcagct     360 cctgctggaa acgacctacc aacagttgtt tacaacgtaa accacgatat attagatgga    420
agcgaagatg ttatctcagg tgcttcatgt actacaaact gcttagctcc aatggctaaa    480 gcttttaaatg ataacttcgg attaaacaaa ggtttcatga ctacaatcca tgcttacact    540
aatgaccaaa acactttaga tgctccacac aaaaaaggag acttaagaag agctagagct    600
gctgctgcta acatagttcc aaactcaact ggagctgcta agctatcgg tttagttatc     660 ccagaattag ctggtaaaatt agacggaaac gctcaaagag tacctgtaat aactggttca    720
ttaactgagt tagtttgtac tttagataaa aaagtaacag tagaagaagt aaacgctgct    780
atgaaagctg cttcaaacga atcattcgga tacactgaag atccaatagt atcatcagac    840
gttatcggaa taagcttcgg atcattattc gatgctactc aaacaaaaat aatggaagtt    900
gacggacaac aattagttaa agttgcttca tggtatgaca cgaagcttc atacactaac     960 caattaatca gaactttaaa atgcttagtt tctaagtaa                          999
```

<210> SEQ ID NO 28
<211> LENGTH: 332
<212> TYPE: PRT
<213> ORGANISM: Clostridium perfringens
<400> SEQUENCE: 28

```
Met Val Lys Val Ala Ile Asn Gly Phe Gly Arg Ile Gly Arg Leu Ala
1               5                   10                  15

Leu Arg Leu Met Ile Asp Asn Pro Glu Phe Glu Val Val Ala Ile Asn
            20                  25                  30

Asp Leu Thr Asp Ala Lys Thr Leu Ala His Leu Phe Lys Tyr Asp Ser
        35                  40                  45

Ala Gln Gly Arg Phe Asn Gly Glu Ile Glu Val Lys Glu Gly Ala Phe
    50                  55                  60

Val Val Asn Gly Lys Glu Ile Lys Val Thr Ala Lys Ser Asn Pro Ala
65                  70                  75                  80

Glu Leu Pro Trp Gly Glu Leu Gly Val Asp Val Val Leu Glu Cys Thr
                85                  90                  95
```

```
Gly Phe Phe Ala Ser Lys Glu Lys Ala Ser His Leu Thr Ala Gly
                100                 105                 110

Ala Lys Lys Val Val Ile Ser Ala Pro Ala Gly Asn Asp Leu Pro Thr
        115                 120                 125

Val Val Tyr Asn Val Asn His Asp Ile Leu Asp Gly Ser Glu Asp Val
130                 135                 140

Ile Ser Gly Ala Ser Cys Thr Thr Asn Cys Leu Ala Pro Met Ala Lys
145                 150                 155                 160

Ala Leu Asn Asp Asn Phe Gly Leu Asn Lys Gly Phe Met Thr Thr Ile
                165                 170                 175

His Ala Tyr Thr Asn Asp Gln Asn Thr Leu Asp Ala Pro His Lys Lys
            180                 185                 190

Gly Asp Leu Arg Arg Ala Arg Ala Ala Ala Asn Ile Val Pro Asn
        195                 200                 205

Ser Thr Gly Ala Ala Lys Ala Ile Gly Leu Val Ile Pro Glu Leu Ala
    210                 215                 220

Gly Lys Leu Asp Gly Asn Ala Gln Arg Val Pro Val Ile Thr Gly Ser
225                 230                 235                 240

Leu Thr Glu Leu Val Cys Thr Leu Asp Lys Lys Val Thr Val Glu Glu
                245                 250                 255

Val Asn Ala Ala Met Lys Ala Ala Ser Asn Glu Ser Phe Gly Tyr Thr
            260                 265                 270

Glu Asp Pro Ile Val Ser Ser Asp Val Ile Gly Ile Ser Phe Gly Ser
        275                 280                 285

Leu Phe Asp Ala Thr Gln Thr Lys Ile Met Glu Val Asp Gly Gln Gln
    290                 295                 300

Leu Val Lys Val Ala Ser Trp Tyr Asp Asn Glu Ala Ser Tyr Thr Asn
305                 310                 315                 320

Gln Leu Ile Arg Thr Leu Lys Cys Leu Val Ser Lys
                325                 330

<210> SEQ ID NO 29
<211> LENGTH: 999
<212> TYPE: DNA
<213> ORGANISM: Clostridium perfringens

<400> SEQUENCE: 29
atggtaaaag tagctattaa cggctttggc cgcatcggcc gcctggcgct gcgcctgatg      60
atcgacaacc ctgagtttga ggttgtagca atcaacgacc tgactgatgc taagactctg     120
gcacacctgt tcaaatacga ttcagcacaa ggccgcttca atggtgaaat cgaagttaaa     180
gaaggcgctt tcgtagttaa cggcaaagaa atcaaagtaa ctgctaaaag caaccctgct     240
gaactgccat ggggcgaact gggcgtagac gtagtactgg agtgtactgg cttcttcgca     300
tcaaaagaga aagcttcagc tcacctgact gctggtgcta aaaaagttgt tatctcagct     360
cctgctggca acgacctgcc aacagttgtt tacaacgtaa accacgatat cctggatggc     420
agcgaagatg ttatctcagg tgcttcatgt actacaaact gcctggctcc aatggctaaa     480
gctctgaatg ataacttcgg cctgaacaaa ggtttcatga ctacaatcca tgcttacact     540
aatgaccaaa acactctgga tgctccacac aaaaaaggcg acctgcgccg cgctcgcgct     600
gctgctgcta acatcgttcc aaactcaact ggcgctgcta agctatcgg tctggttatc     660 ccagaactgg ctggtaaact ggacggcaac gctcaacgcg tacctgtaat cactggttca     720
ctgactgagc tggtttgtac tctggataaa aaagtaacag tagaagaagt aaacgctgct     780
```

-continued

```
atgaaagctg cttcaaacga atcattcggc tacactgaag atccaatcgt atcatcagac      840
gttatcggca tcagcttcgg ctcactgttc gatgctactc aaacaaaaat catggaagtt      900
gacggccaac aactggttaa agttgcttca tggtatgaca cgaagcttc  atacactaac      960 caactgatcc gcactctgaa atgcctggtt tctaagtaa                              999
```

<210> SEQ ID NO 30
<211> LENGTH: 867
<212> TYPE: DNA
<213> ORGANISM: Clostridium perfringens

<400> SEQUENCE: 30

```
atggcattag ttaacgcaaa agaaatgtta aataaagcaa gagaaggaaa atacgctgtt       60
ggtcaattca acataaacaa cttagaatgg acaaaagcta tattattaac tgctcaagaa      120
aataactcac cagttatatt aggagtatca gaaggtgctg ctaaatacat gtgtggattc      180
aaaacaatag ttggaatggt taacggaatg ttagaagaat taaaaataac tgttcctgta      240
gcattacact tagatcacgg tagctaccaa ggagctatag atgctatgga tgctggattc      300
tcatcagtaa tgttcgatgg atcacactac tcaatcgaag aaaacatagt taaaactaaa      360
gaaataatca acttagctgc tgctaaaaac gtatcagttg aagctgaagt tggatcaatc      420
ggtggagaag aagacggtgt tgttggagct ggtgaaatcg ctgatcctgc tgaatgtaaa      480
caaatcgctg aattaggagt tactatgtta gctgctggta tcggaaacat tcacggaaaa      540
taccctgcaa actgggctgg attaaacttc gaagctttag ctaacattaa agctgctact      600
ggagatatgc ctttagtatt acacggtggt actggaatcc cttcagatat gatcgcagaa      660
gctatatcat taggagtatc aaaaataaat gttaatactg agtgtcaatt atcatttgct      720
gaagctactc gtaaatatat agaagctgga aaagacttag aaggaaaagg atttgaccca      780
agaaaattat aaatcctgg  attcgaagct ataaaagcta cagttaaaga aaaaatggaa      840
ttattcggtt cagtaaacag agcttaa                                           867
```

<210> SEQ ID NO 31
<211> LENGTH: 288
<212> TYPE: PRT
<213> ORGANISM: Clostridium perfringens

<400> SEQUENCE: 31

```
Met Ala Leu Val Asn Ala Lys Glu Met Leu Asn Lys Ala Arg Glu Gly
1               5                   10                  15

Lys Tyr Ala Val Gly Gln Phe Asn Ile Asn Asn Leu Glu Trp Thr Lys
            20                  25                  30

Ala Ile Leu Leu Thr Ala Gln Glu Asn Asn Ser Pro Val Ile Leu Gly
        35                  40                  45

Val Ser Glu Gly Ala Ala Lys Tyr Met Cys Gly Phe Lys Thr Ile Val
    50                  55                  60

Gly Met Val Asn Gly Met Leu Glu Glu Leu Lys Ile Thr Val Pro Val
65                  70                  75                  80

Ala Leu His Leu Asp His Gly Ser Tyr Gln Gly Ala Ile Asp Ala Met
                85                  90                  95

Asp Ala Gly Phe Ser Ser Val Met Phe Asp Gly Ser His Tyr Ser Ile
            100                 105                 110

Glu Glu Asn Ile Val Lys Thr Lys Glu Ile Ile Asn Leu Ala Ala Ala
        115                 120                 125
```

| | | | | | | | | | | | |
|---|---|---|---|---|---|---|---|---|---|---|---|
| Lys | Asn | Val | Ser | Val | Glu | Ala | Glu | Val | Gly | Ser | Ile Gly Gly Glu |
| | 130 | | | | 135 | | | | 140 | | |
| Asp | Gly | Val | Val | Gly | Ala | Gly | Glu | Ile | Ala | Asp | Pro Ala Glu Cys Lys |
| 145 | | | | | 150 | | | | | 155 | 160 |
| Gln | Ile | Ala | Glu | Leu | Gly | Val | Thr | Met | Leu | Ala | Ala Gly Ile Gly Asn |
| | | | | 165 | | | | | 170 | | 175 |
| Ile | His | Gly | Lys | Tyr | Pro | Ala | Asn | Trp | Ala | Gly | Leu Asn Phe Glu Ala |
| | | | | 180 | | | | | 185 | | 190 |
| Leu | Ala | Asn | Ile | Lys | Ala | Ala | Thr | Gly | Asp | Met | Pro Leu Val Leu His |
| | | | 195 | | | | | 200 | | | 205 |
| Gly | Gly | Thr | Gly | Ile | Pro | Ser | Asp | Met | Ile | Ala | Glu Ala Ile Ser Leu |
| | 210 | | | | | 215 | | | | | 220 |
| Gly | Val | Ser | Lys | Ile | Asn | Val | Asn | Thr | Glu | Cys | Gln Leu Ser Phe Ala |
| 225 | | | | | 230 | | | | | 235 | 240 |
| Glu | Ala | Thr | Arg | Lys | Tyr | Ile | Glu | Ala | Gly | Lys | Asp Leu Glu Gly Lys |
| | | | | 245 | | | | | 250 | | 255 |
| Gly | Phe | Asp | Pro | Arg | Lys | Leu | Leu | Asn | Pro | Gly | Phe Glu Ala Ile Lys |
| | | | 260 | | | | | 265 | | | 270 |
| Ala | Thr | Val | Lys | Glu | Lys | Met | Glu | Leu | Phe | Gly | Ser Val Asn Arg Ala |
| | | | 275 | | | | | 280 | | | 285 |

<210> SEQ ID NO 32
<211> LENGTH: 867
<212> TYPE: DNA
<213> ORGANISM: Clostridium perfringens

<400> SEQUENCE: 32

```
atggcactgg ttaacgcaaa agaaatgctg aataaagcac gcgaaggcaa atacgctgtt      60
ggtcaattca acatcaacaa cctggaatgg acaaaagcta tcctgctgac tgctcaagaa     120
aataactcac cagttatcct gggcgtatca gaaggtgctg ctaaatacat gtgtggcttc     180
aaaacaatcg ttggcatggt taacggcatg ctggaagaac tgaaaatcac tgttcctgta     240
gcactgcacc tggatcacgg tagctaccaa ggcgctatcg atgctatgga tgctggcttc     300
tcatcagtaa tgttcgatgg ctcacactac tcaatcgaag aaaacatcgt taaaactaaa     360
gaaatcatca acctggctgc tgctaaaaac gtatcagttg aagctgaagt tggctcaatc     420
ggtggcgaag aagacggtgt tgttggcgct ggtgaaatcg ctgatcctgc tgaatgtaaa     480
caaatcgctg aactgggcgt tactatgctg gctgctggta tcggcaacat tcacggcaaa     540
taccctgcaa actgggctgg cctgaacttc gaagctctgg ctaacattaa agctgctact     600
ggcgatatgc ctctggtact gcacggtggt actggcatcc cttcagatat gatcgcagaa     660
gctatctcac tgggcgtatc aaaaatcaat gttaatactg agtgtcaact gtcatttgct     720
gaagctactc gtaaatatat cgaagctggc aaagacctgg aaggcaaagg ctttgaccca     780
cgcaaactgc tgaatcctgg cttcgaagct atcaaagcta cagttaaaga aaaatggaa     840
ctgttcggtt cagtaaaccg cgcttaa                                          867
```

RECOMBINANT BACTERIUM CAPABLE OF ELICITING A PROTECTIVE IMMUNE RESPONSE AGAINST *C. PERFRINGENS*

REFERENCE TO SEQUENCE LISTING

A paper copy of the sequence listing and a computer readable form of the same sequence listing are appended below and herein incorporated by reference. The information recorded in computer readable form is identical to the written sequence listing, according to 37 C.F.R. 1.821 (f).

FIELD OF THE INVENTION

The invention encompasses a recombinant bacterium capable of eliciting an immune response against *Clostridium perfringens* in a host.

BACKGROUND OF THE INVENTION

*C. perfringens* is a ubiquitous gram positive, spore-forming, anaerobic organism, found in many environments surrounding poultry production, or other agricultural activities associated with animal rearing, including soil, dust, feces, feed, litter, rodents, and the intestinal contents of asymptomatic animals. The toxins produced by *C. perfringens* strains cause necrotic enteritis (NE) in severe cases and have the ability, at lower doses, to cause a subclinical necrotic enteritis with thickening of the intestinal mucosa and decreased length of microvili in the ileum. The collective impact of *C. perfringens* colonization is to reduce the absorptive surface in the intestinal tract with a consequent reduction in the ability of birds, and most likely other animals including humans, to benefit from nutrients in food, resulting in a reduced rate of growth. *C. perfringens* induces cellulitis and gangrenous dermatitis and is becoming an increasing concern in turkeys as well. Additionally, it is a frequent cause of gas gangrene in humans.

It is interesting to note that the majority of antibiotics added to poultry feed that are most effective as growth promoters are active against gram-positive bacteria, such as *Clostridia*. In addition, the most prevalently used ionophore anti-coccidial drugs also exhibit anti-clostridial activities. Therefore, *C. perfringens* infections and NE have been traditionally controlled by addition of Antimicrobial Growth Promoters (AGP) and coccidiostats, to control *Eimeria* infections, in the animal feed. Large quantities of antimicrobials were used as AGP and as prophylaxis against enteric bacterial pathogens, including *C. perfringens*. The use of AGP has been condemned due to concerns about increased antibiotic resistance in human pathogens. Consequently, the recent increase in sporadic outbreaks and widespread sub-clinical NE is linked to the withdrawal of AGP. This had been observed initially in Scandinavian countries following the ban on AGP in the early nineties. Furthermore, the decline in use of ionophore coccidiostats, which can prevent *C. perfringens* lesions, due to the introduction of vaccines to prevent *Eimeria* infections, has exacerbated the resurgence of NE. Thus, NE is a re-emerging disease and a major threat to the current objective of 'antimicrobial-free' poultry farming.

*C. perfringens* can cause a range of health problems in infected birds, ranging from a subclinical infection which can result in poor feed conversion caused by decreased digestion and adsorption, to necrotic enteritis, resulting in a variety of symptoms including severe depression, decreased appetite, reluctance to move, diarrhea and ruffled feathers, often leading to death. Clinical illness is usually short, with birds often simply found dead. Onset of disease symptoms generally occurs in broilers from two to five weeks of age, coinciding with the disappearance of maternal antibodies. However, NE has also been reported in layers of various ages. Gross lesions typically involve the ileum and jejunum, although cecal lesions can occur. Intestines are friable and distended with gas and fluid and a diphtheritic membrane is often found in the mucosa. Subclinical infection with *C. perfringens* can lead to economic losses, due to reduced growth rates and poor feed conversion. It is likely that losses due to subclinical infections may constitute a larger problem overall than losses due to acute disease. Occasionally, cholagniohepatitis can result, leading to condemnation losses at slaughter.

In a recent study, the Food Safety and Inspection Service (FSIS) determined *Salmonella* serotypes isolated from swine, ground turkey, ground beef and broilers in processing plants participating in the Hazard Analysis and Critical Control Point (HACCP) systems for pathogen reduction and found that 87% of the *Salmonella* isolates were from poultry sources. Using data from the Centers for Disease Control and Prevention collected in 2005, it is evident that some *Salmonella* serotypes that are most frequently isolated from humans are also very prevalent in poultry, with 8 of the *Salmonella* serotypes predominantly isolated from poultry being represented in the top 20 serotypes isolated from humans Hence, there is a need in the art for an inexpensive, effective oral vaccine against *C. perfringens* for control of both subclinical infections and NE in poultry. However, vaccines that are effective in controlling such infections in poultry might have applications in control of *C. perfringens* infections in other animal species and even in humans. In addition, such vaccines if they reduced *Salmonella* infection and colonization in farm animals would benefit food safety by lessening the likelihood for transmission of *Salmonella* through the food chain to humans.

SUMMARY OF THE INVENTION

One aspect of the invention encompasses a recombinant *Salmonella* bacterium. The bacterium is capable of the expression of at least one nucleic acid encoding at least one *Clostridium perfringens* antigen. The bacterium, when administered to a host, typically elicits an immune response against *Clostridium perfringens*.

Another aspect of the invention encompasses a vaccine composition. The vaccine composition comprises a recombinant bacterium capable of the expression of at least one nucleic acid encoding at least one *Clostridium perfringens* antigen. The vaccine composition, when administered to a host, when administered to a host, typically elicits an immune response against *Clostridium perfringens*.

Yet another aspect of the invention is a method of inducing an immune response against *Clostridium perfringens*. The method comprises administering a composition comprising a recombinant bacterium capable of the expression of at least one nucleic acid encoding at least one *Clostridium perfringens* antigen to a host.

Other aspects and iterations of the invention are described more thoroughly below.

REFERENCE TO COLOR FIGURES

The application file contains at least one photograph executed in color. Copies of this patent application publication with color photographs will be provided by the Office upon request and payment of the necessary fee.

BRIEF DESCRIPTION OF THE FIGURES

FIG. 3 depicts the predicted amino acid sequence and alignment of alpha toxin (PLC) mature protein sequences of strain CP995, an NE isolate (SEQ ID NO:13), and ATCC 13124 (SEQ ID NO:14). Residues in CP995 that are different from those of ATCC 13124 are indicated. The underlined fragment, amino acids 248 to 370, represents the C-terminal domain (PlcC) of the recombinant vaccine antigen.

FIG. 19A,B depicts the optimized FBA sequence (SEQ ID NO:30 is the sense nucleic acid; SEQ ID NO:31 is the reverse complement; SEQ ID NO:32 is the amino acid sequence).

DETAILED DESCRIPTION OF THE INVENTION

Figure 1:
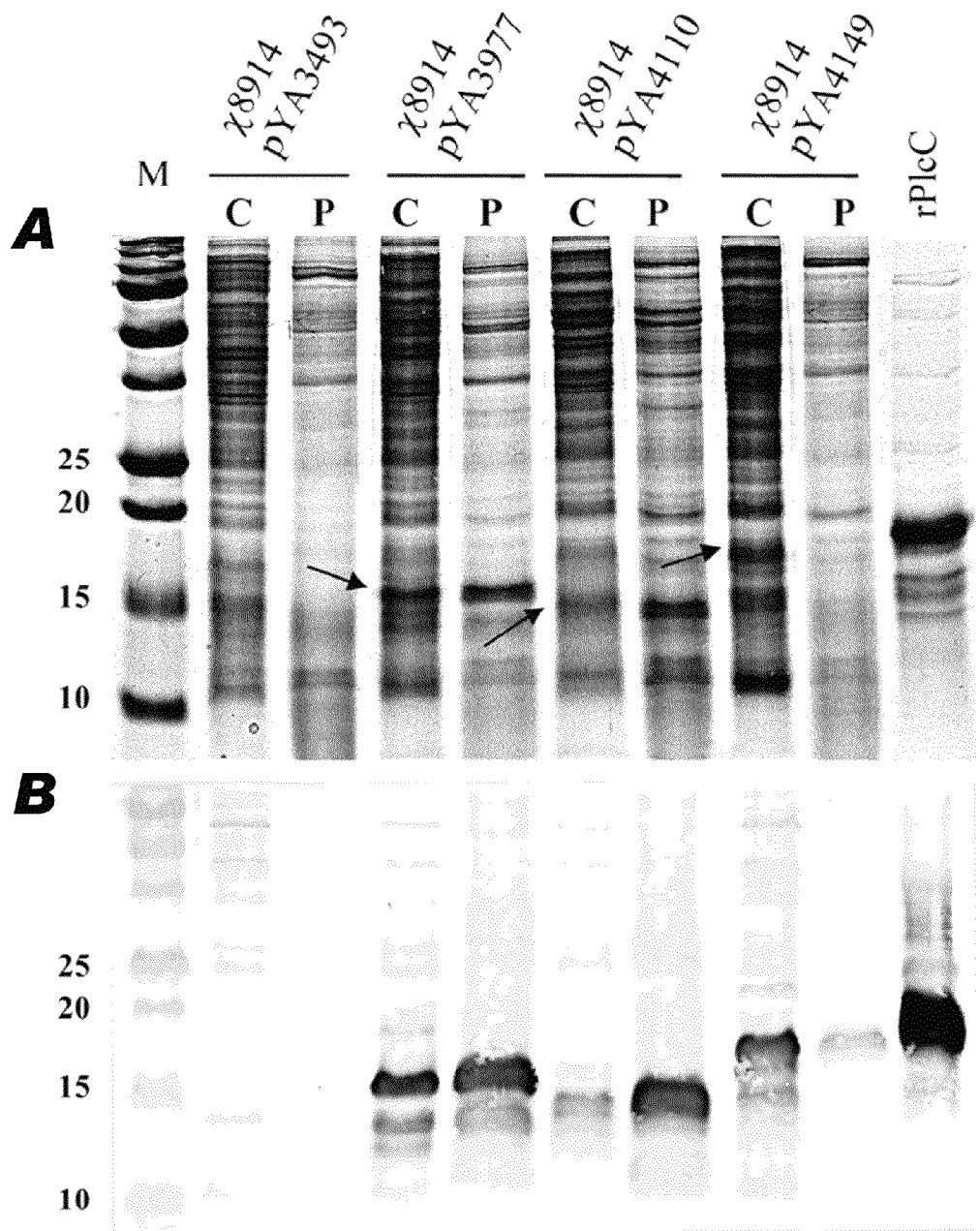
FIG. 1 depicts the expression of the PlcC antigen by the *S. enterica* serovar *Typhimurium* vaccine strain harboring different PlcC expression plasmids. (A) Coomassie blue-stained SDS-PAGE. Lanes: M, molecular mass marker (in kilodaltons) (Bio-Rad, Hercules, Calif.); C, cytoplasmic fraction; P, periplasmic fraction. (B) Western blot of an analogous gel with rabbit anti-PlcC hyperimmune serum. Arrows show PlcC protein bands that also correspond to bands detected by western blotting.

The present invention encompasses a recombinant bacterium capable of eliciting an immune response against *C. perfringens*. A vaccine composition comprising a recombinant bacterium of the invention may provide economic benefit to the poultry producer by inducing an immune response to *C. perfringens*. The immune response would result in enhanced feed conversion efficiency and more rapid growth, without the costs or potential human health hazards of using growth-promoting antibiotics. Additionally, the vaccine composition may substantially reduce *Salmonella* infection of poultry and thus contamination of carcasses and eggs. Therefore, use of the vaccine composition of the invention may contribute to reducing the likelihood of human infection due to *Salmonella* transmission through the food chain.

I. Recombinant Bacterium

One aspect of the present invention encompasses a recombinant *Salmonella* bacterium. The bacterium, when administered to a host, typically elicits an immune response against *C. perfringens*. Generally speaking, the bacterium is capable of the expression of at least one nucleic acid encoding at least one *C. perfringens* antigen. In some embodiments, the recombinant bacterium is also capable of the regulated expression of a nucleic acid encoding at least one serotype-specific antigen of the bacterium. In exemplary embodiments, the bacterium does not substantially induce an immune response specific to the serotype of the recombinant bacterium.

In exemplary embodiments, a recombinant *Salmonella* bacterium of the invention is capable of colonizing a host to substantially the same extent as a wild-type bacterium of the same serotype. A bacterium of the invention, however, will preferably be substantially avirulent after colonization.

In some embodiments, the recombinant bacterium may be a *Salmonella enterica* serovar. In an exemplary embodiment, a bacterium of the invention may be derived from *S. Typhimurium, S. Typhi, S. Paratyphi, S. Gallinarum, S. Enteritidis, S. Choleraesius, S. Arizonae*, or *S. Dublin*. In an exemplary embodiment, a bacterium of the invention may be derived from *S. Typhimurium, S. Enteriditis*, or *S. Gallinarum*. In all cases, a recombinant bacterium of the invention generally does not comprise any drug resistance nucleic acid sequences or other sequence scars in the chromosomes of the recombinant strain.

(a) Expression of at Least One Serotype-Specific Antigen

In certain embodiments, a recombinant bacterium of the invention may be capable of the regulated expression of a nucleic acid encoding at least one serotype-specific antigen. As used herein, the phrase "serotype-specific antigen" refers to an antigen that elicits an immune response specific for the bacterial vector serotype. In some embodiments, the immune response to a serotype-specific antigen may also recognize closely related strains in the same serogroup, but in a different, but related, serotype. Non-limiting examples of serotype-specific antigens may include LPS O-antigen, one or more components of a flagellum, and Vi capsular antigen. In some embodiments, the expression of at least one, at least two, at least three, or at least four nucleic acid sequences encoding a serotype-specific antigen may be regulated in a bacterium of the invention.

The phrase "regulated expression of a nucleic acid encoding at least one serotype-specific antigen" refers to expression of the nucleic acid encoding a serotype-antigen such that the bacterium does not substantially induce an immune response specific to the bacterial vector serotype. In one embodiment, the expression of the serotype-specific antigen is eliminated. In another embodiment, the expression is substantially reduced. In yet another embodiment, the expression of the serotype-specific antigen is reduced in a temporally controlled manner. For instance, the expression of the serotype-specific antigen may be reduced during growth of the bacterium in a host, but not during in vitro growth.

The expression of a nucleic acid encoding a *Salmonella* serotype-specific antigen may be measured using standard molecular biology and protein chemistry techniques known to one of skill in the art. As used herein, "substantial reduction" of the expression of a nucleic acid encoding a serotype-specific antigen refers to a reduction of at least about 1% to at least about 99.9% as compared to a *Salmonella* bacterium in which no attempts have been made to reduce serotype-specific antigen expression. In one embodiment, the expression of a nucleic acid encoding a serotype-specific antigen is reduced by 100% by using a deletion mutation. In other embodiments of the invention, the expression of a nucleic acid encoding a serotype-specific antigen is reduced by at least about 99.9%, 99.5%, 99%, 98%, 97%, 96%, 95%, 94%, 93%, 92%, 91% or 90%. In yet other embodiments of the invention, the expression of a nucleic acid encoding a serotype-specific antigen is reduced by at least about 89%, 88%, 87%, 86%, 85%, 84%, 83%, 82%, 81% or 80%. In still other embodiments of the invention, the expression of a nucleic acid encoding a serotype-specific antigen is reduced by at least about 75%, 70%, 65%, 60%, 55%, or 50%. In additional embodiments, the expression of a nucleic acid encoding a serotype-specific antigen is reduced by at least about 45%, 40%, 35%, 30%, 25%, or 20%. In yet additional embodiments, the expression of a nucleic acid encoding a serotype-specific antigen is reduced by at least about 15%, 10%, 5%, 4%, 3%, 2% or 1%.

Methods of regulating expression of a nucleic acid encoding at least one serotype-specific antigen are discussed in detail below, and in the examples.

i. LPS O-Antigen Expression

In one embodiment, the expression of a nucleic acid encoding the serotype-specific antigen LPS O-antigen is regulated by mutating the pmi nucleic acid sequence, which encodes a phosphomannose isomerase needed for the bacterium to interconvert fructose-6-P and mannose-6-P. In some instances, the bacterium comprises a Δpmi mutation, such as a Δpmi-2426 mutation. A bacterium comprising a Δpmi-2426 mutation, grown in the presence of mannose, is capable of synthesizing a complete LPS O-antigen. But non-phosphorylated mannose, which is the form required for bacterial uptake, is unavailable in vivo. Hence, a bacterium comprising a Δpmi-2426 mutation loses the ability to synthesize LPS O-antigen serotype specific side chains after a few generations of growth in vivo. The LPS that is synthesized comprises a core structure that is substantially similar across many diverse *Salmonella* serotypes. This results in a bacterium that is capable of eliciting an immune response against at least two *Salmonella* serotypes without substantially inducing an immune response specific to the serotype of the bacterial vector.

A bacterium of the invention that comprises a Δpmi mutation may also comprise other mutations that ensure that mannose available to the bacterium during in vitro growth is used for LPS O-antigen synthesis. For instance, a bacterium may comprise a Δ(gmd-fcl)-26 mutation. This mutation deletes two nucleic acid sequences that encode enzymes for conversion of GDP-mannose to GDP-fucose. This ensures that mannose available to the bacterium during in vitro growth is used for LPS O-antigen synthesis and not colanic acid production. Similarly, a bacterium may comprise the Δ(wza-wcaM)-8 mutation, which deletes all 19 nucleic acid sequences necessary for colanic acid production, and also precludes conversion of GDP-mannose to GDP-fucose.

In addition to regulating LPS O-antigen synthesis with mannose, the synthesis of LPS O-antigen may be regulated by arabinose, which is also absent in vivo. For instance, a bacterium may comprise the mutation $\Delta P_{rfc}$::TT araC $P_{BAD}$ rfc. (P stands for promoter and TT stands for transcription terminator.) The rfc (otherwise known as wzy) nucleic acid sequence is necessary for the addition of O-antigen subunits, which typically comprise three or four sugars, in a repeat fashion. When the rfc nucleic acid sequence is absent, only one O-antigen repeat subunit is added to the LPS core polysaccharide. Normally, the serotype-specific O-antigen contains some 50 or so repeats of the O-antigen subunit, catalyzed by the enzyme encoded by the rfc nucleic acid sequence. In the case of a bacterium comprising the $\Delta P_{rfc}$::TT araC $P_{BAD}$ rfc deletion-insertion mutation, expression of the rfc nucleic acid sequence is dependant on the presence of arabinose that can be supplied during in vitro growth of the strain, but that is absent in vivo. Consequently, rfc expression ceases in vivo, resulting in the cessation of assembly of the O-antigen repeat structure. This reduces the bacterium's ability to induce an immune response against the serotype-specific O-antigen.

Another means to regulate LPS O-antigen expression is to eliminate the function of galE in a recombinant bacterium of the invention. The galE nucleic acid sequence encodes an enzyme for the synthesis of UDP-Gal, which is a substrate for LPS O-antigen, the outer LPS core and colanic acid. Growth of a bacterium comprising a suitable galE mutation in the presence of galactose leads to the synthesis of O-antigen and the LPS core. Non-phosphorylated galactose is unavailable in vivo, however, and in vivo synthesis of UDP-Gal ceases, as does synthesis of the O-antigen and the LPS outer core. One example of a suitable galE mutation is the Δ(galE-ybhC)-851 mutation.

In certain embodiments, a bacterium of the invention may comprise one or more of the Δpmi, $\Delta P_{rfc}$::TT araC $P_{BAD}$ rfc, and ΔgalE mutations, with or without a Δ(gmd-fcl)-26 or Δ(wza-wcaM)-8 mutation. Such a combination may yield a recombinant bacterium that synthesizes all components of the LPS core and O-antigen side chains when grown in vitro (i.e. in the presence of suitable concentrations of mannose, arabinose and galactose), but that ceases to synthesize the LPS outer core and O-antigen in vivo due to the unavailability of free unphosphorylated mannose, arabinose or galactose. Also, a recombinant bacterium with the inability to synthesize the LPS outer core and/or O-antigen is attenuated, as the bacterium is more susceptible to macrophages and/or complement-mediated cytotoxicity. Additionally, a bacterium with the inability to synthesize the LPS outer core and O-antigen in vivo, induces only a minimal immune response to the serotype-specific LPS O-antigen.

ii. Expression of a Component of a Flagellum

In one embodiment, the expression of a serotype-specific component of a flagellum is regulated by mutating the nucleic acid that encodes FljB or FliC. For instance, a bacterium of the invention may comprise a ΔfljB217 mutation. Alternatively, a bacterium may comprise a ΔfliC180 mutation. The ΔfljB217 mutation deletes the structural nucleic acid sequence that encodes the Phase II flagellar antigen whereas the ΔfliC180 mutation deletes the 180 amino acids encoding the antigenically variable serotype-specific domain of the Phase I FliC flagellar antigen. The portion of the flagellar protein that interacts with TLR5 to recruit/stimulate innate immune responses represents the conserved N- and C-terminal regions of the flagellar proteins and this is retained and expressed by strains with the ΔfliC180 mutation. In addition, the ΔfliC180 mutation retains the CD4-dependent T-cell epitope. It should be noted, that expression of the Phase I flagellar antigen and not the Phase II flagellar antigen potentiates *S. Typhimurium* infection of mice. *S. Typhimurium* recombinant bacteria with the Δpmi-2426, ΔfljB217 and ΔfliC180 mutations, when grown in the absence of mannose, are not agglutinated with antisera specific for the B-group O-antigen or the *S. Typhimurium* specific anti-flagellar sera. These recombinant bacteria are also non-motile since the FliC180 protein that is synthesized at high levels is not efficiently incorporated into flagella. When these recombinant bacteria are evaluated using HEK293 cells specifically expressing TLR5, the level of NFKB production is about 50% higher than when using a ΔfliB217 F1iC+ strain that assembles flagellin into flagella and exhibits motility (there is no NFKB production by the control ΔfljB217 ΔfliC2426 strain with no flagella). Similarly, recombinant bacteria with the Δ(galE-ybhC)-851, ΔfljB217 and ΔfliC180 mutations, when grown in the absence of galactose, are not agglutinated with antisera specific for the B-group O-antigen or the *S. Typhimurium* specific anti-flagellar sera. These bacteria are also non-motile.

iii. Expression of a Nucleic Acid Encoding the Vi Capsular Antigen

Certain *Salmonella* strains, such as *S. Typhi* and *S. Dublin*, express the Vi capsular antigen. This antigen is serotype-specific, inhibits invasion, and acts to suppress induction of a protective immune response. Consequently, when a recombinant bacterium of the invention is derived from a strain comprising the Vi capsular antigen, one or more nucleic acids encoding the Vi capsular antigen will be deleted such that the Vi capsular antigen is not synthesized.

(b) Expression of at Least One *C. Perfringens* Antigen

Generally speaking, a recombinant bacterium of the invention is capable of the expression of at least one nucleic acid encoding at least one *C. perfringens* antigen. As used herein, the phrase "*C. perfringens* antigen" refers to an antigen that elicits an immune response against *C. perfringens*. In an exemplary embodiment, the *C. perfringens* antigen elicits a protective immune response against *C. perfringens*. Non-limiting examples of *C. perfringens* antigens may include PlcC, or NetB (otherwise referred to as CpbX), GDP, PFOR, FBA, HP, or a fragment thereof. In other embodiments, the antigen is NetB, tPFOR, or tHP.

It is not necessary that the nucleic acid encoding a *C. perfringens* antigen comprise the complete nucleic acid sequence of the antigen. It is only necessary that the *C. perfringens* antigen sequence used be capable of eliciting an immune response. The antigen may be one that was not found in that exact form in the parent organism. For example, a sequence coding for an antigen comprising 100 amino acid residues may be transferred in part into a recombinant bacterium so that a peptide comprising only 75, 65, 55, 45, 35, 25, 15, or even 10, amino acid residues is produced by the recombinant bacterium. Alternatively, if the amino acid sequence of a particular *C. perfringens* antigen or fragment thereof is known, it may be possible to chemically synthesize the nucleic acid fragment or analog thereof by means of automated nucleic acid sequence synthesizers, PCR, or the like and introduce said nucleic acid sequence into the appropriate copy number vector.

In certain embodiments, a *C. perfringens* antigen of the invention may comprise a B cell epitope or a T cell epitope. Alternatively, an antigen to which an immune response is desired may be expressed as a fusion to a carrier protein that contains a strong promiscuous T cell epitope and/or serves as an adjuvant and/or facilitates presentation of the antigen to enhance, in all cases, the immune response to the antigen or its component part. This can be accomplished by methods known in the art. Fusion to tetnus toxin fragment C, CT-B, LT-B and hepatitis virus B core are particularly useful for these purposes, although other epitope presentation systems are well known in the art.

In further embodiments, a nucleic acid sequence encoding an antigen of the invention may comprise a secretion signal. Non-limiting examples of suitable secretion signals may include the bla, dsbA, eltII-B, or ompA secretion signals. In other embodiments, an antigen of the invention may be toxic to the recombinant bacterium.

In another alternative, a recombinant bacterium may comprise a long sequence of nucleic acid encoding several nucleic acid sequence products, one or all of which may be *C. perfringens* antigens. In some embodiments, the expression of at least one, at least two, at least three, at least four, at least five, at least six, or more nucleic acids encoding *C. perfringens* antigens is regulated in a bacterium of the invention. These antigens may be encoded by two or more open reading frames operably linked to be expressed coordinately as an operon, wherein each antigen is synthesized independently. Alternatively, the two or more antigens may be encoded by a single open reading frame such that the antigens are synthesized as a fusion protein.

Methods of expressing an antigen in a recombinant bacterium are known in the art. In certain embodiments, vectors, as detailed below, may be used to express an antigen. For more details, see the examples.

In many cases, the high level expression of a nucleic acid sequence encoding an antigen in a bacterium reduces the bacterium's fitness, such that the bacterium grows slowly, is susceptible to stresses encountered in the host, and is generally less able to effectively colonize effector lymphoid tissues. High level expression of a nucleic acid sequence encoding an antigen, however, is highly desirable to maximize induction of an immune response against the antigen. Consequently, the phrase "regulated expression of a nucleic acid encoding at least one *C. perfringens* antigen" refers to expression of the nucleic acid encoding at least one *C. perfringens* antigen in a bacterium such that the bacterium is capable of colonizing a host at levels similar to a wild-type bacterium, and yet is still capable of eliciting an immune response against *C. perfringens* when administered to the host. Methods of regulating expression of at least one *C. perfringens* antigen are discussed in detail below.

i. Chromosomally Integrated Nucleic Acid Sequence Encoding a Repressor

In one embodiment, the expression of a nucleic acid sequence encoding a *C. perfringens* antigen is regulated by a chromosomally integrated nucleic acid sequence encoding a repressor and a vector. For instance, a recombinant bacterium of the invention that is capable of the regulated expression of a nucleic acid sequence encoding at least one *C. perfringens* antigen may comprise, in part, at least one chromosomally integrated nucleic acid sequence encoding a repressor. Typically, the nucleic acid sequence encoding a repressor is operably linked to a regulatable promoter. The nucleic acid sequence encoding a repressor and/or the promoter may be modified from the wild-type nucleic acid sequence so as to optimize the expression level of the nucleic acid sequence encoding the repressor.

Methods of chromosomally integrating a nucleic acid sequence encoding a repressor operably-linked to a regulatable promoter are known in the art and detailed in the examples. Generally speaking, the nucleic acid sequence encoding a repressor should not be integrated into a locus that disrupts colonization of the host by the recombinant bacterium, or attenuates the bacterium. In one embodiment, the nucleic acid sequence encoding a repressor may be integrated into the relA nucleic acid sequence. In another embodiment, the nucleic acid sequence encoding a repressor may be integrated into the endA nucleic acid sequence.

In some embodiments, at least one nucleic acid sequence encoding a repressor is chromosomally integrated. In other embodiments, at least two, or at least three nucleic acid sequences encoding repressors may be chromosomally integrated into the recombinant bacterium. If there is more than one nucleic acid sequence encoding a repressor, each nucleic acid sequence encoding a repressor may be operably linked to a regulatable promoter, such that each promoter is regulated by the same compound or condition. Alternatively, each nucleic acid sequence encoding a repressor may be operably linked to a regulatable promoter, each of which is regulated by a different compound or condition.

A. Repressor

As used herein, "repressor" refers to a biomolecule that represses transcription from one or more promoters. Generally speaking, a suitable repressor of the invention is synthesized in high enough quantities during the in vitro growth of the bacterial strain to repress the transcription of the nucleic acid encoding an antigen of interest on the vector, as detailed below, and not impede the in vitro growth of the strain. Additionally, a suitable repressor will generally be substantially stable, i.e. not subject to proteolytic breakdown. Furthermore, a suitable repressor will be diluted by about half at every cell division after expression of the repressor ceases, such as in a non-permissive environment (e.g. an animal or human host).

The choice of a repressor depends, in part, on the species of the recombinant bacterium used. For instance, the repressor is usually not derived from the same species of bacteria as the recombinant bacterium. For instance, the repressor may be derived from *E. coli* if the recombinant bacterium is from the genus *Salmonella*. Alternatively, the repressor may be from a bacteriophage.

Suitable repressors are known in the art, and may include, for instance, LacI of *E. coli*, C2 encoded by bacteriophage P22, or C1 encoded by bacteriophage λ. Other suitable repressors may be repressors known to regulate the expression of a regulatable nucleic acid sequence, such as nucleic acid sequences involved in the uptake and utilization of sugars. In one embodiment, the repressor is LacI. In another embodiment, the repressor is C2. In yet another embodiment, the repressor is C1.

B. Regulatable Promoter

The chromosomally integrated nucleic acid sequence encoding a repressor is operably linked to a regulatable promoter. The term "promoter", as used herein, may mean a synthetic or naturally-derived molecule that is capable of conferring, activating or enhancing expression of a nucleic acid. A promoter may comprise one or more specific transcriptional regulatory sequences to further enhance expression and/or to alter the spatial expression and/or temporal expression of a nucleic acid. The term "operably linked," as used herein, means that expression of a nucleic acid is under the control of a promoter with which it is spatially connected. A promoter may be positioned 5' (upstream) of the nucleic acid under its control. The distance between the promoter and a nucleic acid to be expressed may be approximately the same as the distance between that promoter and the native nucleic acid sequence it controls. As is known in the art, variation in this distance may be accommodated without loss of promoter function.

The regulated promoter used herein generally allows transcription of the nucleic acid sequence encoding a repressor while in a permissive environment (i.e. in vitro growth), but ceases transcription of the nucleic acid sequence encoding a repressor while in a non-permissive environment (i.e. during growth of the bacterium in an animal or human host). For instance, the promoter may be sensitive to a physical or chemical difference between the permissive and non-permissive environment. Suitable examples of such regulatable promoters are known in the art.

In some embodiments, the promoter may be responsive to the level of arabinose in the environment. Generally speaking, arabinose may be present during the in vitro growth of a bacterium, while typically absent from host tissue. In one embodiment, the promoter is derived from an araC-$P_{BAD}$ system. The araC-$P_{BAD}$ system is a tightly regulated expression system that has been shown to work as a strong promoter induced by the addition of low levels of arabinose. The araC-araBAD promoter is a bidirectional promoter controlling expression of the araBAD nucleic acid sequences in one direction, and the araC nucleic acid sequence in the other direction. For convenience, the portion of the araC-araBAD promoter that mediates expression of the araBAD nucleic acid sequences, and which is controlled by the araC nucleic acid sequence product, is referred to herein as $P_{BAD}$. For use as described herein, a cassette with the araC nucleic acid sequence and the araC-araBAD promoter may be used. This cassette is referred to herein as araC-$P_{BAD}$. The AraC protein is both a positive and negative regulator of $P_{BAD}$. In the presence of arabinose, the AraC protein is a positive regulatory element that allows expression from $P_{BAD}$. In the absence of arabinose, the AraC protein represses expression from $P_{BAD}$. This can lead to a 1,200-fold difference in the level of expression from $P_{BAD}$. Full induction of $P_{BAD}$ transcription also requires binding of the Crp-cAMP complex, which is a key regulator of catabolite repression.

Other enteric bacteria contain arabinose regulatory systems homologous to the araC araBAD system from *E. coli*. For example, there is homology at the amino acid sequence level between the *E. coli* and the *S. Typhimurium* AraC proteins, and less homology at the DNA level. However, there is high specificity in the activity of the AraC proteins. For example, the *E. coli* AraC protein activates only *E. coli* $P_{BAD}$ (in the presence of arabinose) and not *S. Typhimurium* $P_{BAD}$. Thus, an arabinose regulated promoter may be used in a recombinant bacterium that possesses a similar arabinose operon, without substantial interference between the two, if the promoter and the operon are derived from two different species of bacteria.

Generally speaking, the concentration of arabinose necessary to induce expression is typically less than about 2%. In some embodiments, the concentration is less than about 1.5%, 1%, 0.5%, 0.2%, 0.1%, or 0.05%. In other embodiments, the concentration is 0.05% or below, e.g. about 0.04%, 0.03%, 0.02%, or 0.01%. In an exemplary embodiment, the concentration is about 0.05%.

In other embodiments, the promoter may be responsive to the level of maltose in the environment. Generally speaking, maltose may be present during the in vitro growth of a bacterium, while typically absent from host tissue. The malT nucleic acid encodes MalT, a positive regulator of four maltose-responsive promoters ($P_{PQ}$, $P_{EFG}$, $P_{KBM}$, and $P_S$). The combination of malT and a mal promoter creates a tightly regulated expression system that has been shown to work as a strong promoter induced by the addition of maltose (6). Unlike the araC-$P_{BAD}$ system, malT is expressed from a promoter ($P_T$) functionally unconnected to the other mal promoters. $P_T$ is not regulated by MalT. The malEFG-malKBM promoter is a bidirectional promoter controlling expression of the malKBM nucleic acid sequences in one direction, and the malEFG nucleic acid sequences in the other direction. For convenience, the portion of the malEFG-malKBM promoter that mediates expression of the malKBM nucleic acid sequence, and which is controlled by the malT nucleic acid sequence product, is referred to herein as $P_{KBM}$, and the portion of the malEFG-malKBM promoter that mediates expression of the malEFG nucleic acid sequence, and that is controlled by the malT nucleic acid sequence product, is referred to herein as $P_{EFG}$. Full induction of $P_{KBM}$ requires the presence of the MalT binding sites of $P_{EFG}$. For use in the vectors and systems described herein, a cassette with the malT nucleic acid sequence and one of the mal promoters may be used. This cassette is referred to herein as malT-$P_{mal}$. In the presence of maltose, the MalT protein is a positive regulatory element that allows expression from $P_{mal}$.

In still other embodiments, the promoter may be sensitive to the level of rhamnose in the environment. Analogous to the araC-$P_{BAD}$ system described above, the rhaRS-$P_{rhaB}$ activator-promoter system is tightly regulated by rhamnose. Expression from the rhamnose promoter ($P_{rha}$) is induced to high levels by the addition of rhamnose, which is common in bacteria but rarely found in host tissues. The nucleic acid sequences rhaBAD are organized in one operon that is controlled by the $P_{rhaBAD}$ promoter. This promoter is regulated by two activators, RhaS and RhaR, and the corresponding nucleic acid sequences belong to one transcription unit that is located in the opposite direction of the rhaBAD nucleic acid sequences. If L-rhamnose is available, RhaR binds to the $P_{rhaRS}$ promoter and activates the production of RhaR and RhaS. RhaS together with L-rhamnose in turn binds to the $P_{rhaBAD}$ and the $P_{rhaT}$ promoter and activates the transcription of the structural nucleic acid sequences. Full induction of rhaBAD transcription also requires binding of the Crp-cAMP complex, which is a key regulator of catabolite repression.

Although both L-arabinose and L-rhamnose act directly as inducers for expression of regulons for their catabolism, important differences exist in regard to the regulatory mechanisms. L-Arabinose acts as an inducer with the activator AraC in the positive control of the arabinose regulon. However, the L-rhamnose regulon is subject to a regulatory cascade; it is therefore subject to even tighter control than the araC $P_{BAD}$ system. L-Rhamnose acts as an inducer with the activator RhaR for synthesis of RhaS, which in turn acts as an activator in the positive control of the rhamnose regulon. In the present invention, rhamnose may be used to interact with the RhaR protein and then the RhaS protein may activate transcription of a nucleic acid sequence operably-linked to the $P_{rhaBAD}$ promoter.

In still other embodiments, the promoter may be sensitive to the level of xylose in the environment. The xylR-$P_{xylA}$ system is another well-established inducible activator-promoter system. Xylose induces xylose-specific operons (xylE, xylFGHR, and xylAB) regulated by XylR and the cyclic AMP-Crp system. The XylR protein serves as a positive regulator by binding to two distinct regions of the xyl nucleic acid sequence promoters. As with the araC-$P_{BAD}$ system described above, the xylR-$P_{xylAB}$ and/or xylR-$P_{xylFGH}$ regulatory systems may be used in the present invention. In these embodiments, xylR $P_{xylAB}$ xylose interacting with the XylR protein activates transcription of nucleic acid sequences operably-linked to either of the two $P_{xyl}$ promoters.

The nucleic acid sequences of the promoters detailed herein are known in the art, and methods of operably-linking them to a chromosomally integrated nucleic acid sequence encoding a repressor are known in the art and detailed in the examples.

C. Modification to Optimize Expression

A nucleic acid sequence encoding a repressor and regulatable promoter detailed above, for use in the present invention, may be modified so as to optimize the expression level of the nucleic acid sequence encoding the repressor. The optimal level of expression of the nucleic acid sequence encoding the repressor may be estimated, or may be determined by experimentation. Such a determination should take into consideration whether the repressor acts as a monomer, dimer, trimer, tetramer, or higher multiple, and should also take into consideration the copy number of the vector encoding the antigen of interest, as detailed below. In an exemplary embodiment, the level of expression is optimized so that the repressor is synthesized while in the permissive environment (i.e. in vitro growth) at a level that substantially inhibits the expression of a nucleic acid sequence encoding a *C. perfringens* antigen, and is substantially not synthesized in a non-permissive environment, thereby allowing expression of the nucleic acid encoding a *C. perfringens* antigen.

As stated above, the level of expression may be optimized by modifying the nucleic acid sequence encoding the repressor and/or promoter. As used herein, "modify" refers to an alteration of the nucleic acid sequence of the repressor and/or promoter that results in a change in the level of transcription of the nucleic acid sequence encoding the repressor, or that results in a change in the level of synthesis of the repressor. For instance, in one embodiment, modify may refer to altering the start codon of the nucleic acid sequence encoding the repressor. Generally speaking, a GTG or TTG start codon, as opposed to an ATG start codon, may decrease translation efficiency ten-fold. In another embodiment, modify may refer to altering the Shine-Dalgarno (SD) sequence of the nucleic acid sequence encoding the repressor. The SD sequence is a ribosomal binding site generally located 6-7 nucleotides upstream of the start codon. The SD consensus sequence is AGGAGG, and variations of the consensus sequence may alter translation efficiency. In yet another embodiment, modify may refer to altering the distance between the SD sequence and the start codon. In still another embodiment, modify may refer to altering the −35 sequence for RNA polymerase recognition. In a similar embodiment, modify may refer to altering the −10 sequence for RNA polymerase binding. In an additional embodiment, modify may refer to altering the number of nucleotides between the −35 and −10 sequences. In an alternative embodiment, modify may refer to optimizing the codons of the nucleic acid sequence encoding the repressor to alter the level of translation of the mRNA encoding the repressor. For instance, non-A rich codons initially after the start codon of the nucleic acid sequence encoding the repressor may not maximize translation of the mRNA encoding the repressor. Similarly, the codons of the nucleic acid sequence encoding the repressor may be altered so as to mimic the codons from highly synthesized proteins of a particular organism. In a further embodiment, modify may refer to altering the GC content of the nucleic acid sequence encoding the repressor to enhance the stability of expression in *Salmonella*.

In some embodiments, more than one modification or type of modification may be performed to optimize the expression level of the nucleic acid sequence encoding the repressor. For instance, at least one, two, three, four, five, six, seven, eight, or nine modifications, or types of modifications, may be performed to optimize the expression level of the nucleic acid sequence encoding the repressor.

By way of non-limiting example, when the repressor is LacI, then the nucleic acid sequence of LacI and the promoter may be altered so as to increase the level of LacI synthesis. In one embodiment, the start codon of the LacI repressor may be altered from GTG to ATG. In another embodiment, the SD sequence may be altered from AGGG to AGGA. In yet another embodiment, the codons of lacI may be optimized according to the codon usage for highly synthesized proteins of *Salmonella*. In a further embodiment, the start codon of lacI may be altered, the SD sequence may be altered, and the codons of lacI may be optimized.

Methods of modifying the nucleic acid sequence encoding the repressor and/or the regulatable promoter are known in the art and detailed in the examples.

D. Transcription Termination Sequence

In some embodiments, the chromosomally integrated nucleic acid sequence encoding the repressor further comprises a transcription termination sequence. A transcription termination sequence may be included to prevent inappropriate expression of nucleic acid sequences adjacent to the chromosomally integrated nucleic acid sequence encoding the repressor and regulatable promoter.

E. Vector

A recombinant bacterium of the invention that is capable of the regulated expression of at least one nucleic acid sequence encoding a *C. perfringens* antigen may also comprise, in part, a vector. The vector comprises a nucleic acid sequence encoding at least one *C. perfringens* antigen operably linked to a promoter. The promoter is regulated by the chromosomally encoded repressor, such that the expression of the nucleic acid sequence encoding an antigen is repressed during in vitro growth of the bacterium, but the bacterium is capable of high level synthesis of the antigen in an animal or human host.

As used herein, "vector" refers to an autonomously replicating nucleic acid unit. The present invention can be practiced with any known type of vector, including viral, cosmid, phasmid, and plasmid vectors. The most preferred type of vector is a plasmid vector.

As is well known in the art, plasmids and other vectors may possess a wide array of promoters, multiple cloning sequences, transcription terminators, etc., and vectors may be selected so as to control the level of expression of the nucleic acid sequence encoding an antigen by controlling the relative copy number of the vector. In some instances in which the vector might encode a surface localized adhesin as the antigen, or an antigen capable of stimulating T-cell immunity, it may be preferable to use a vector with a low copy number such as at least two, three, four, five, six, seven, eight, nine, or ten copies per bacterial cell. A non-limiting example of a low copy number vector may be a vector comprising the pSC101 ori.

In other cases, an intermediate copy number vector might be optimal for inducing desired immune responses. For instance, an intermediate copy number vector may have at least 10, 11, 12, 13, 14, 15, 16, 17, 18, 19, 20, 21, 22, 23, 24, 25, 26, 27, 28, 29, or 30 copies per bacterial cell. A non-limiting example of an intermediate copy number vector may be a vector comprising the p15A ori.

In still other cases, a high copy number vector might be optimal for the induction of maximal antibody responses or mucosal immune responses. A high copy number vector may have at least 31, 35, 40, 45, 50, 55, 60, 65, 70, 75, 80, 85, 90, 95, or 100 copies per bacterial cell. In some embodiments, a high copy number vector may have at least 100, 125, 150, 175, 200, 225, 250, 275, 300, 325, 350, 375, or 400 copies per bacterial cell. Non-limiting examples of high copy number vectors may include a vector comprising the pBR on or the pUC ori.

Additionally, vector copy number may be increased by selecting for mutations that increase plasmid copy number. These mutations may occur in the bacterial chromosome but are more likely to occur in the plasmid vector.

Preferably, vectors used herein do not comprise antibiotic resistance markers to select for maintenance of the vector.

A vector may comprise one or more than one nucleic acid sequences encoding a C. perfringens antigen, whether regulated or not, as detailed above.

F. Promoter Regulated by Repressor

The vector comprises a nucleic acid sequence encoding at least one C. perfringens antigen operably-linked to a promoter regulated by the repressor, encoded by a chromosomally integrated nucleic acid sequence. One of skill in the art would recognize, therefore, that the selection of a repressor dictates, in part, the selection of the promoter operably-linked to a nucleic acid sequence encoding an antigen of interest. For instance, if the repressor is LacI, then the promoter may be selected from the group consisting of LacI responsive promoters, such as $P_{trc}$, $P_{lac}$, $P_{T7lac}$ and $P_{tac}$. If the repressor is C2, then the promoter may be selected from the group consisting of C2 responsive promoters, such as P22 promoters $P_L$ and $P_R$. If the repressor is C1, then the promoter may be selected from the group consisting of C1 responsive promoters, such as λ promoters $P_L$ and $P_R$.

In each embodiment herein, the promoter regulates expression of a nucleic acid sequence encoding the antigen, such that expression of the nucleic acid sequence encoding an antigen is repressed when the repressor is synthesized (i.e. during in vitro growth of the bacterium), but expression of the nucleic acid sequence encoding an antigen is high when the repressor is not synthesized (i.e. in an animal or human host). Generally speaking, the concentration of the repressor will decrease with every cell division after expression of the nucleic acid sequence encoding the repressor ceases. In some embodiments, the concentration of the repressor decreases enough to allow high level expression of the nucleic acid sequence encoding a C. perfringens antigen after about 2, 3, 4, 5, 6, 7, 8, 9, 10, 11, or 12 divisions of the bacterium. In an exemplary embodiment, the concentration of the repressor decreases enough to allow high level expression of the nucleic acid sequence encoding a C. perfringens antigen after about 5 divisions of the bacterium in an animal or human host.

In certain embodiments, the promoter may comprise other regulatory elements. For instance, the promoter may comprise lacO if the repressor is LacI. This is the case with the lipoprotein promoter $P_{lpp}$ that is regulated by LacI since it possesses the LacI binding domain lacO.

In one embodiment, the repressor is a LacI repressor and the promoter is $P_{trc}$.

G. Expression of the Nucleic Acid Sequence Encoding an Antigen

As detailed above, generally speaking the expression of the nucleic acid sequence encoding the C. perfringens antigen should be repressed when the repressor is synthesized. For instance, if the repressor is synthesized during in vitro growth of the bacterium, expression of the nucleic acid sequence encoding the C. perfringens antigen should be repressed. Expression may be "repressed" or "partially repressed" when it is about 50%, 45%, 40%, 35%, 30%, 25%, 20%, 15%, 10%, 5%, 1%, or even less than 1% of the expression under non-repressed conditions. Thus although the level of expression under conditions of "complete repression" might be exceedingly low, it is likely to be detectable using very sensitive methods since repression can never by absolute.

Conversely, the expression of the nucleic acid sequence encoding the antigen should be high when the expression of the nucleic acid sequence encoding the repressor is repressed. For instance, if the nucleic acid sequence encoding the repressor is not expressed during growth of the recombinant bacterium in the host, the expression of the nucleic acid sequence encoding the antigen should be high. As used herein, "high level" expression refers to expression that is strong enough to elicit an immune response to the antigen. Consequently, the copy number correlating with high level expression can and will vary depending on the antigen and the type of immune response desired. Methods of determining whether an antigen elicits an immune response such as by measuring antibody levels or antigen-dependant T cell populations or antigen-dependant cytokine levels are known in the art, and methods of measuring levels of expression of antigen encoding sequences by measuring levels of mRNA transcribed or by quantitating the level of antigen synthesis are also known in the art. For more details, see the examples.

ii. Other Ways of Regulating at Least One C. Perfringens Antigen

The invention also encompasses other means of regulating the expression of a nucleic acid sequence encoding at least one C. perfringens antigen in a recombinant bacterium. For instance, in one embodiment, the C. perfringens antigen of interest may be encoded on an extra-chromosomal vector. This can be used in the context of a balanced-lethal host-vector system. Alternatively, the nucleotide sequence encoding the antigen of interest may be inserted into the chromosome but have its expression controlled by a regulatable system, e.g., LacI or C2, as with the regulated gene encoding the antigen of interest on an extra-chromosomal vector (e.g., a plasmid).

(c) Attenuation of the Recombinant Bacterium

In each of the above embodiments, a recombinant bacterium of the invention capable of regulated expression may also be attenuated. "Attenuated" refers to the state of the bacterium wherein the bacterium has been weakened from its wild type fitness by some form of recombinant or physical manipulation. This includes altering the genotype of the bacterium to reduce its ability to cause disease. However, the bacterium's ability to colonize the gut (in the case of Salmonella) and induce immune responses is, preferably, not substantially compromised. For instance, in one embodiment, regulated attenuation allows the recombinant bacterium to express one or more nucleic acids encoding products important for the bacterium to withstand stresses encountered in the host after immunization. This allows efficient invasion and colonization of lymphoid tissues before the recombinant bacterium is regulated to display the attenuated phenotype.

In one embodiment, a recombinant bacterium may be attenuated as described in section I(a)i above, i.e. regulating LPS O-antigen. In another embodiment, a recombinant bacterium may be attenuated as described in section (c)i below. In which case, both regulated attenuation and regulated expression of an enteric antigen encoding sequence may be dependent upon an arabinose regulatable system. Consequently, the concentration of arabinose needed for optimal expression of the regulated enteric antigen encoding sequence may not be the same as the concentration for optimal expression of attenuation. In an exemplary embodiment, the concentration of arabinose for the optimization of both regulated attenuation and regulated expression of sequences encoding antigen will be substantially the same.

Accordingly, the promoter and/or the nucleic acid sequence encoding an attenuation protein may be modified to optimize the system. Methods of modification are detailed above. Briefly, for example, the SD ribosome binding sequence may be altered, and/or the start codon may be altered from ATG to GTG for the nucleic acid sequences fur and phoPQ, so that the production levels of Fur and PhoPQ are optimal for both the regulated attenuation phenotype and the regulated expression when growing strains with a given concentration of arabinose. One of skill in the art will appreciate that other nuceic acid sequences, in addition to fur and phoPQ, may also be altered as described herein in combination with other well-known protocols. In addition, these attenuating nucleic acid sequences may be regulated by other systems using well-established protocols known to one of skill in the art. For example, they may be regulated using with promoters dependent on addition of maltose, rhamnose, or xylose rather than arabinose.

Other methods of attenuation are known in the art. For instance, attenuation may be accomplished by altering (e.g., deleting) native nucleic acid sequences found in the wild type bacterium. For instance, if the bacterium is *Salmonella*, non-limiting examples of nucleic acid sequences which may be used for attenuation include: a pab nucleic acid sequence, a pur nucleic acid sequence, an aro nucleic acid sequence, asd, a dap nucleic acid sequence, nadA, pncB, galE, pmi, fur, rpsL, ompR, htrA, hemA, cdt, cya, crp, dam, phoP, phoQ, rfc, poxA, galU, mviA, sodC, recA, ssrA, sirA, inv, hilA, rpoE, flgM, tonB, slyA, and any combination thereof. Exemplary attenuating mutations may be aroA, aroC, aroD, cdt, cya, crp, phoP, phoQ, ompR, galE, and htrA.

In certain embodiments, the above nucleic acid sequences may be placed under the control of a sugar regulated promoter wherein the sugar is present during in vitro growth of the recombinant bacterium, but substantially absent within an animal or human host. The cessation in transcription of the nucleic acid sequences listed above would then result in attenuation and the inability of the recombinant bacterium to induce disease symptoms.

The bacterium may also be modified to create a balanced-lethal host-vector system, although other types of systems may also be used (e.g., creating complementation heterozygotes). For the balanced-lethal host-vector system, the bacterium may be modified by manipulating its ability to synthesize various essential constituents needed for synthesis of the rigid peptidoglycan layer of its cell wall. In one example, the constituent is diaminopimelic acid (DAP). Various enzymes are involved in the eventual synthesis of DAP. In one example, the bacterium is modified by using a ΔasdA mutation to eliminate the bacterium's ability to produce β-aspartate semi-aldehyde dehydrogenase, an enzyme essential for the synthesis of DAP. One of skill in the art can also use the teachings of U.S. Pat. No. 6,872,547 for other types of mutations of nucleic acid sequences that result in the abolition of the synthesis of DAP. These nucleic acid sequences may include, but are not limited to, dapA, dapB, dapC, dapD, dapE, dapF, and asd. Other modifications that may be employed include modifications to a bacterium's ability to synthesize D-alanine or to synthesize D-glutamic acid (e.g., Δmurl mutations), which are both unique constituents of the peptidoglycan layer of the bacterial cell wall.

Yet another balanced-lethal host-vector system comprises modifying the bacterium such that the synthesis of an essential constituent of the rigid layer of the bacterial cell wall is dependent on a nutrient (e.g., arabinose) that can be supplied during the growth of the microorganism. For example, a bacterium may—comprise the $\Delta P_{murA}$::TT araC $P_{BAD}$ murA deletion-insertion mutation. This type of mutation makes synthesis of muramic acid (another unique essential constituent of the peptidoglycan layer of the bacterial cell wall) dependent on the presence of arabinose that can be supplied during growth of the bacterium in vitro.

When arabinose is absent, however, as it is in an animal or human host, the essential constituent of the peptidoglycan layer of the cell wall is not synthesized. This mutation represents an arabinose dependant lethal mutation. In the absence of arabinose, synthesis of muramic acid ceases and lysis of the bacterium occurs because the peptidoglycan layer of the cell wall is not synthesized. It is not possible to generate ΔmurA mutations because they are lethal. The necessary nutrient, a phosphorylated muramic acid, cannot be exogenously supplied because enteric bacteria cannot take the nutrient up from the media. Recombinant bacteria with a $\Delta P_{murA}$::TT araC $P_{BAD}$ murA deletion-insertion mutation grown in the presence of arabinose exhibit effective colonization of effector lymphoid tissues after oral vaccination prior to undergoing lysis due to the inability to synthesize muramic acid.

Similarly, various embodiments may comprise the araC $P_{BAD}$ c2 cassette inserted into the asd nucleic acid sequence that encodes aspartate semialdehyde dehydrogenase. Since the araC nucleic acid sequence is transcribed in a direction that could lead to interference in the expression of adjacent nucleic acid sequences and adversely affect vaccine strain performance, a transcription termination (TT) sequence is generally inserted 3' to the araC nucleic acid sequence. The chromosomal asd nucleic acid sequence is typically inactivated to enable use of plasmid vectors encoding the wild-type asd nucleic acid sequence in the balanced lethal host-vector system. This allows stable maintenance of plasmids in vivo in the absence of any drug resistance attributes that are not permissible in live bacterial vaccines. In some of these embodiments, the wild-type asd nucleic acid sequence may be encoded by the vector described above.

In one embodiment, ΔasdA27::TT araC $P_{BAD}$ c2 has an improved SD sequence and a codon optimized c2 nucleic acid sequence. The C2 repressor synthesized in the presence of arabinose is used to repress nucleic acid sequence expression from P22 $P_R$ and $P_L$ promoters. In another embodiment, ΔasdA27::TT araC $P_{BAD}$ c2 has the 1104 base-pair asd nucleic acid sequence deleted (1 to 1104, but not including the TAG stop codon) and the 1989 base-pair fragment containing T4 ipIII TT araC $P_{BAD}$ c2 inserted. The c2 nucleic acid sequence in ΔasdA27::TT araC $P_{BAD}$ c2 has a SD sequence that was optimized to TAAGGAGGT. It also has an improved $P_{BAD}$ promoter such that the −10 sequence is improved from TACTGT to TATAAT. Furthermore, it has a codon optimized c2 nucleic acid sequence, in which the second codon was modified from AAT to AAA.

In further embodiments, the bacterium may be attenuated by regulating the murA nucleic acid sequence encoding the first enzyme in muramic acid synthesis and the asd nucleic acid sequence essential for DAP synthesis. These embodiments may comprise the chromosomal deletion-insertion mutations ΔasdA19::TT araC $P_{BAD}$ c2 or ΔasdA27::TT araC $P_{BAD}$ c2 and $\Delta P_{murA7}$::araC $P_{BAD}$ murA or $\Box P_{murA12}$::TT araC $P_{BAD}$ murA or $\Delta P_{murA25}$::TT araC $P_{BAD}$ murA. This host-vector grows in LB broth with 0.1% L-arabinose, but is unable to grow in or on media devoid of arabinose since it undergoes cell wall-less death by lysis. In some embodiments of the invention, the recombinant bacterium may comprise araBAD and araE mutations to preclude breakdown and leakage of internalized arabinose such that asd and murA nucleic acid sequence expression continues for a cell division or two after oral immunization into an environment that is devoid of external arabinose. (For example a strain with the $\Delta P_{murA7}$::TT araC $P_{BAD}$ murA deletion-insertion mutation undergoes about two cell divisions and then commences to lyse in media made of mouse or chicken feed or chicken breast meat, unless they are supplemented with arabinose). Either GTG or TTG start codons for the murA and asd nucleic acid sequences are important to decrease translation efficiency on multi-copy plasmids. For instance plasmid vector pYA3681 contains the murA nucleic acid sequence (with altered start codon sequences to decrease translation efficiency) under the control of an araC $P_{BAD}$ promoter. Also the second nucleic acid sequence under the direction of this promoter is the asd nucleic acid sequence (with altered start codon sequences to decrease translation efficiency). The P22 $P_R$ promoter is in the anti-sense direction of both the asd nucleic acid sequence and the murA nucleic acid sequence. The P22 $P_R$ is repressed by the C2 repressor made during growth of the strain in media with arabinose (due to the $\Delta$asdA19::TT araC $P_{BAD}$ c2 deletion-insertion). However C2 concentration decreases due to cell division in vivo to cause $P_R$ directed synthesis of anti-sense mRNA to further block translation of asd and murA mRNA. The araC $P_{BAD}$ sequence is also not from *E. coli* B/r as originally described but represents a sequence derived from *E. coli* K-12 strain χ289 with tighter control and less leakiness in the absence of arabinose. In the preferred embodiment, transcription terminators (TT) flank all of the domains for controlled lysis, replication, and expression so that expression in one domain does not affect the activities of another domain. As a safety feature, the plasmid asd nucleic acid sequence does not replace the chromosomal asd mutation since they have a deleted sequence in common, consequently, the *E. coli* murA nucleic acid sequence was used in the plasmid instead of using the *Salmonella* murA nucleic acid sequence. The recombinant bacterium of this embodiment is avirulent at oral doses in excess of $10^9$ CFU to BALB/c mice. In addition to being fully attenuated, this construction exhibits complete biological containment with no in vivo recombinant bacteria survivors detectable after 21 days and no recombinant bacteria survivors during or after excretion. This property enhances vaccine safety and minimizes the potential for vaccination of individuals not intended for vaccination.

i. Regulated Attenuation

The present invention also encompasses a recombinant bacterium capable of regulated attenuation. Generally speaking, the bacterium comprises a chromosomally integrated regulatable promoter. The promoter replaces the native promoter of, and is operably linked to, at least one nucleic acid sequence encoding an attenuation protein, such that the absence of the function of the protein renders the bacterium attenuated. In some embodiments, the promoter is modified to optimize the regulated attenuation.

In each of the above embodiments described herein, more than one method of attenuation may be used. For instance, a recombinant bacterium of the invention may comprise a regulatable promoter chromosomally integrated so as to replace the native promoter of, and be operably linked to, at least one nucleic acid sequence encoding an attenuation protein, such that the absence of the function of the protein renders the bacterium attenuated, and the bacterium may comprise another method of attenuation detailed in section I above.

A. Attenuation Protein

Herein, "attenuation protein" is meant to be used in its broadest sense to encompass any protein the absence of which attenuates a bacterium. For instance, in some embodiments, an attenuation protein may be a protein that helps protect a bacterium from stresses encountered in the gastrointestinal tract or respiratory tract. Non-limiting examples may be the RpoS, PhoPQ, OmpR, Fur, and Crp proteins. In other embodiments, the protein may be a necessary component of the cell wall of the bacterium, such as the protein encoded by murA. In still other embodiments, the protein may be listed in Section i above.

The native promoter of at least one, two, three, four, five, or more than five attenuation proteins may be replaced by a regulatable promoter as described herein. In one embodiment, the promoter of one of the proteins selected from the group comprising RpoS, PhoPQ, OmpR, Fur, and Crp may be replaced. In another embodiment, the promoter of two, three, four or five of the proteins selected from the group comprising RpoS, PhoPQ, OmpR, Fur, and Crp may be replaced.

If the promoter of more than one attenuation protein is replaced, each promoter may be replaced with a regulatable promoter, such that the expression of each attenuation protein encoding sequence is regulated by the same compound or condition. Alternatively, each promoter may be replaced with a different regulatable promoter, such that the expression of each attenuation protein encoding sequence is regulated by a different compound or condition such as by the sugars arabinose, maltose, rhamnose or xylose.

B. Regulatable Promoter

The native promoter of a nucleic acid encoding an attenuation protein is replaced with a regulatable promoter operably linked to the nucleic acid sequence encoding an attenuation protein. The term "operably linked," is defined above.

The regulatable promoter used herein generally allows transcription of the nucleic acid sequence encoding the attenuation protein while in a permissive environment (i.e. in vitro growth), but cease transcription of the nucleic acid sequence encoding an attenuation protein while in a non-permissive environment (i.e. during growth of the bacterium in an animal or human host). For instance, the promoter may be responsive to a physical or chemical difference between the permissive and non-permissive environment. Suitable examples of such regulatable promoters are known in the art and detailed above.

In some embodiments, the promoter may be responsive to the level of arabinose in the environment, as described above. In other embodiments, the promoter may be responsive to the level of maltose, rhamnose, or xylose in the environment, as described above. The promoters detailed herein are known in the art, and methods of operably linking them to a nucleic acid sequence encoding an attenuation protein are known in the art.

In certain embodiments, a recombinant bacterium of the invention may comprise any of the following: $\Delta P_{fur}$::TT araC $P_{BAD}$ fur, $\Delta P_{crp}$::TT araC $P_{BAD}$ crp, $\Delta P_{phoPQ}$::TT araC $P_{BAD}$ phoPQ, or a combination thereof. Growth of such strains in the presence of arabinose leads to transcription of the fur, phoPQ, and/or crp nucleic acid sequences, but nucleic acid sequence expression ceases in a host because there is no free arabinose. Attenuation develops as the products of the fur, phoPQ, and/or the crp nucleic acid sequences are diluted at each cell division. Strains with the $\Delta P_{fur}$ and/or the $\Delta P_{phoPQ}$ mutations are attenuated at oral doses of $10^9$ CFU, even in three-week old mice at weaning. Generally speaking, the concentration of arabinose necessary to induce expression is typically less than about 2%. In some embodiments, the concentration is less than about 1.5%, 1%, 0.5%, 0.2%, 0.1%, or 0.05%. In certain embodiments, the concentration may be about 0.04%, 0.03%, 0.02%, or 0.01%. In an exemplary embodiment, the concentration is about 0.05%. Higher concentrations of arabinose or other sugars may lead to acid production during growth that may inhibit desirable cell densities. The inclusion of mutations such as ΔaraBAD or mutations that block the uptake and/or breakdown of maltose, rhamnose, or xylose, however, may prevent such acid production and enable use of higher sugar concentrations with no ill effects.

When the regulatable promoter is responsive to arabinose, the onset of attenuation may be delayed by including additional mutations, such as ΔaraBAD23, which prevents use of arabinose retained in the cell cytoplasm at the time of oral immunization, and/or ΔaraE25 that enhances retention of arabinose. Thus, inclusion of these mutations may be beneficial in at least two ways: first, enabling higher culture densities, and second enabling a further delay in the display of the attenuated phenotype that may result in higher densities in effector lymphoid tissues to further enhance immunogenicity.

C. Modifications

Attenuation of the recombinant bacterium may be optimized by modifying the nucleic acid sequence encoding an attenuation protein and/or promoter. Methods of modifying a promoter and/or a nucleic acid sequence encoding an attenuation protein are the same as those detailed above with respect to repressors in Section (b).

In some embodiments, more than one modification may be performed to optimize the attenuation of the bacterium. For instance, at least one, two, three, four, five, six, seven, eight or nine modifications may be performed to optimize the attenuation of the bacterium.

In various exemplary embodiments of the invention, the SD sequences and/or the start codons for the fur and/or the phoPQ virulence nucleic acid sequences may be altered so that the production levels of these nucleic acid products are optimal for regulated attenuation. FIG. 8 depicts $\Delta P_{fur77}$::TT araC $P_{BAD}$ fur, whose start codon is changed from ATG to GTG, and $\Delta P_{fur81}$::TT araC $P_{BAD}$ fur, that has a weakened SD sequence as well as the start codon changed from ATG to GTG. FIG. 9 depicts $\Delta P_{phoPQ173}$::TT araC $P_{BAD}$ phoPQ, that has modifications to the start codon as well as the second codon, which was changed from ATG to GTG. FIG. 9 also depicts $\Delta P_{phoPQ177}$::TT araC $P_{BAD}$ phoPQ, wherein the SD sequence has been changed to the weaker AAGG sequence, the start codon was modified, and the second codon was modified from ATG to GTG.

(d) Eliciting an Immune Response Against at Least Two *Salmonella* Serotypes

A recombinant bacterium of the invention is generally capable of eliciting an immune response against at least two *Salmonella* serotypes. This may be accomplished, for instance, by eliminating the serotype-specific LPS O-antigen side chains as discussed above. The remaining LPS core will elicit an immune response, inducing the production of antibodies against the LPS core. Since this LPS core is substantially identical in the several thousand *Salmonella enterica* serotypes, the antibodies potentially provide immunity against several diverse *Salmonella enterica* serotypes, such as *Typhimurium*, Heidelberg, Newport, Infantis, Dublin, Hadar, Kentucky, Thompson, Agona, Ohio, Virchow, Typhi, Enteritidis, and Munchen.

In addition, the elimination of the LPS O-antigen provides the host immune system with better access to the outer membrane proteins of the recombinant bacterium, thereby enhancing induction of immune responses against these outer membrane proteins. In some embodiments, as described below, the outer membrane proteins may be upregulated to further enhance host immune responses to these proteins. Non-limiting examples of outer membrane proteins include proteins involved in iron and manganese uptake, as described below. Iron and manganese are essential nutrients for enteric pathogens and the induction of antibodies that inhibit iron and manganese uptake in effect starves the pathogens, conferring protective immunity on the host. Additionally, since these proteins are homologous among the enteric bacteria, such host immune responses provide immunity against multiple *Salmonella enterica* serotypes.

The elicited immune response may include, but is not limited to, an innate immune response, a humoral immune response and a cell-mediated immune response. In one embodiment, Th2-dependent mucosal and systemic antibody responses to the *C. perfringens* antigen(s) are observed. Immune responses may be measured by standard immunological assays known to one of skill in the art. In an exemplary embodiment, the immune response is protective.

(e) crp Cassette

In some embodiments, a recombinant bacterium of the invention may also comprise a $\Delta P_{crp}$::TT araC $P_{BAD}$ crp deletion-insertion mutation. Since the araC $P_{BAD}$ cassette is dependent both on the presence of arabinose and the binding of the catabolite repressor protein Crp, a $\Delta P_{crp}$::TT araC $P_{BAD}$ crp deletion-insertion mutation may be included as an additional means to reduce expression of any nucleic acid sequence under the control of the $P_{BAD}$ promoter. This means that when the bacterium is grown in a non-permissive environment (i.e. no arabinose) both the repressor itself and the Crp protein cease to be synthesized, consequently eliminating both regulating signals for the araC $P_{BAD}$ regulated nucleic acid sequence. This double shut off of araC $P_{BAD}$ may constitute an additional safety feature ensuring the genetic stability of the desired phenotypes.

Generally speaking, the activity of the Crp protein requires interaction with cAMP, but the addition of glucose, which may inhibit synthesis of cAMP, decreases the ability of the Crp protein to regulate transcription from the araC $P_{BAD}$ promoter. Consequently, to avoid the effect of glucose on cAMP, glucose may be substantially excluded from the growth media, or variants of crp may be isolated that synthesize a Crp protein that is not dependent on cAMP to regulate transcription from $P_{BAD}$. This strategy may also be used in other systems responsive to Crp, such as the systems responsive to rhamnose and xylose described above.

(f) Reduction in Fluid Secretion

In some embodiments, a recombinant bacterium of the invention may be modified so as to reduce fluid secretion in the host. For instance, the bacterium may comprise the ΔsopB1925 mutation. Alternatively, the bacterium may comprise the ΔmsbB48 mutation. For more details, see the Examples.

(g) Biological Containment

Under certain embodiments, a live recombinant bacterium may possess the potential to survive and multiply if excreted from a host. This leads to the possibility that individuals not electing to be immunized may be exposed to the recombinant bacterium. Consequently, in certain embodiments, a recombinant bacterium of the invention may comprise one or more mutations that decrease, if not preclude, the ability of *Salmonella* vaccines to persist in the GI tract of animals.

In another embodiment, a recombinant bacterium of the invention may comprise one or more of the Δ(gmd fcl)-26 or Δ(wcaL-wza)-7, ΔagfBAC811 or Δ(P$_{agfD}$agfG)-4, Δbcs-ABZC2118 or ΔbcsEFG2319 and Δ(yshA-yihW)-157 mutations that block synthesis of colanic acid, thin aggregative fimbriae (i.e., curli), cellulose and extracellular polysaccharide, respectively, all of which contribute to biofilm formation. Since the LPS O-antigen also enables biofilm formation, a strain with the Δpmi-2426, ΔP$_{rfc174}$::TT araC P$_{BAD}$ rfc, and Δ(galE-ybhC)-851 mutations with or without a Δ(gmd-fcl)-26 or Δ(wcaM-wza)-8 mutation would be expected to survive less well in nature because of a dependency on the availability of three sugars simultaneously, an unlikely occurrence. Such a strain would thus exhibit a rough phenotype making it less well to survive in soil or even in the intestinal environment. We also have mutations such as ΔyhiR36 that prevents use of DNA as a nutrient, Δ(shdA-ratB)-64, ΔmisL2 and ΔbigA3 that encode four proteins that enable Salmonella to adhere to host extracellular matrix proteins and ΔackA233 that blocks use of acetate. Some of these mutations have been reported to reduce Salmonella persistence in the intestinal tract of calves and in mice, but this is not so in the intestinal track of chickens. We have yet to put all these mutations abolishing ability to synthesize biofilms, LPS O-antigen, ability to bind to extracellular matrix proteins, and inability to use DNA and acetate as nutrients, but we surmise that such a strain would exhibit a high level of biological containment and be unable to persist in the intestinal tracks of birds or mammals and not survive in the environment if excreted. A further anticipated benefit of such a strain is the further stripping from the vaccine strain cell surface of macromolecules that might mask immunological surveillance of surface localized LPS core and cross reactive outer membrane antigens. Thus we anticipate an enhancement in levels of induced immune responses to expressed antigens. Indeed, vaccine strains with the Δ(wcaM-wza)-8 mutation synthesize five to ten percent more protective antigen and induce similarly higher antibody titers to this antigen. In exemplary embodiments, recombinant bacterium comprising a biological containment mutation are not adversely effected in their virulence or the ability to colonize mice.

In some embodiments, the recombinant bacterium may comprise a method of regulated delayed lysis in vivo that prevents bacterial persistence in vivo and survival if excreted. These mutations include: Δ(gmd-fcl)-26 that precludes synthesis of colanic acid that can protect cells undergoing cell wall-less death from lysing completely and ΔagfBAC811 that blocks synthesis of thin aggregative fimbriae (curli) that are critical for biofilm formation to enable persistent colonization on bile stones in the gall bladder, ΔasdA27::TT araC $P_{BAD}$ c2 insertion-deletion mutation to impose a requirement for the peptidoglycan constituent DAP and $ΔP_{murA12}$::TTaraC $P_{BAD}$ murA insertion-deletion mutation as a conditional-lethal mutation blocking synthesis of the peptidoglycan constituent muramic acid. The latter two mutations are typically complemented by a regulated delayed lysis plasmid vector such as pYA3681 (FIG. 2) that has an arabinose-dependent expression of asdA and murA genes. A recombinant bacterium comprising such mutations grows normally in the presence of arabinose. In vivo, however, the bacterium ceases to express any nucleic acids encoding the AsdA and MurA enzymes, such that synthesis of the peptidoglycan cell wall layer ceases, ultimately resulting in the lysis of the bacterium. This lysis may result in the release of a bolus of antigen specific for an enteric pathogen, thereby serving as a means to enhance induction of immunity against that enteric pathogen while conferring complete biological containment.

II. Vaccine Compositions and Administration

A recombinant bacterium of the invention may be particularly suited for use as a vaccine. Infection of a host with a *Salmonella* strain typically leads to colonization of the gut-associated lymphoid tissue (GALT) or Peyer's patches, which leads to the induction of a generalized mucosal immune response to the recombinant bacterium. Further penetration of the bacterium into the mesenteric lymph nodes, liver and spleen may augment the induction of systemic and cellular immune responses directed against the bacterium. Thus the use of recombinant *Salmonella* for oral immunization stimulates all three branches of the immune system, which is particularly important for immunizing against infectious disease agents that colonize on and/or invade through mucosal surfaces.

A recombinant bacterium of the invention may be administered to a host as a vaccine composition. As used herein, a vaccine composition is a composition designed to elicit an immune response to the recombinant bacterium, including any antigens that may be expressed by the bacterium. In an exemplary embodiment, the immune response is protective. As used herein, "protective" means that the immune response contributes to the lessening of any symptoms associated with infection of a host with the pathogen the antigen was derived from or designed to elicit a response against. For example, a protective antigen from a pathogen, such as *Mycobacterium*, may induce an immune response that helps to ameliorate symptoms associated with *Mycobacterium* infection or reduce the morbidity and mortality associated with infection with the pathogen. The use of the term "protective" in this invention does not necessarily require that the host is completely protected from the effects of the pathogen.

Immune responses to antigens are well studied and widely reported. A survey of immunology is given by Paul, W E, Stites D et. al. and Ogra P L. et. al. (11-13). Mucosal immunity is also described by Ogra P L et. al. (14).

Vaccine compositions of the present invention may be administered to any host capable of mounting an immune response. Such hosts may include all vertebrates, for example, mammals, including domestic animals, agricultural animals, laboratory animals, and humans, and various species of birds, including domestic birds and birds of agricultural importance, such as chickens and turkeys. Preferably, the host is a warm-blooded animal. The vaccine can be administered as a prophylactic or for treatment purposes.

In exemplary embodiments, the recombinant bacterium is alive when administered to a host in a vaccine composition of the invention. Suitable vaccine composition formulations and methods of administration are detailed below.

(a) Vaccine Composition

A vaccine composition comprising a recombinant bacterium of the invention may optionally comprise one or more possible additives, such as carriers, preservatives, stabilizers, adjuvants, and other substances.

In one embodiment, the vaccine comprises an adjuvant. Adjuvants, such as aluminum hydroxide or aluminum phosphate, are optionally added to increase the ability of the vaccine to trigger, enhance, or prolong an immune response. In exemplary embodiments, the use of a live attenuated recombinant bacterium may act as a natural adjuvant. The vaccine compositions may further comprise additional components known in the art to improve the immune response to a vaccine, such as T cell co-stimulatory molecules or antibodies, such as anti-CTLA4. Additional materials, such as cytokines, chemokines, and bacterial nucleic acid sequences naturally found in bacteria, like CpG, are also potential vaccine adjuvants.

In another embodiment, the vaccine may comprise a pharmaceutical carrier (or excipient). Such a carrier may be any solvent or solid material for encapsulation that is non-toxic to the inoculated host and compatible with the recombinant bacterium. A carrier may give form or consistency, or act as a diluent. Suitable pharmaceutical carriers may include liquid carriers, such as normal saline and other non-toxic salts at or near physiological concentrations, and solid carriers not used for humans, such as talc or sucrose, or animal feed. Carriers may also include stabilizing agents, wetting and emulsifying agents, salts for varying osmolarity, encapsulating agents, buffers, and skin penetration enhancers. Carriers and excipients as well as formulations for parenteral and nonparenteral drug delivery are set forth in Remington's Pharmaceutical Sciences 19th Ed. Mack Publishing (1995). When used for administering via the bronchial tubes, the vaccine is preferably presented in the form of an aerosol.

Care should be taken when using additives so that the live recombinant bacterium is not killed, or have its ability to effectively colonize lymphoid tissues such as the GALT, NALT and BALT compromised by the use of additives. Stabilizers, such as lactose or monosodium glutamate (MSG), may be added to stabilize the vaccine formulation against a variety of conditions, such as temperature variations or a freeze-drying process.

The dosages of a vaccine composition of the invention can and will vary depending on the recombinant bacterium, the regulated antigen, and the intended host, as will be appreciated by one of skill in the art. Generally speaking, the dosage need only be sufficient to elicit a protective immune response in a majority of hosts. Routine experimentation may readily establish the required dosage. Typical initial dosages of vaccine for oral administration could be about $1 \times 10^7$ to $1 \times 10^{10}$ CFU depending upon the age of the host to be immunized. Administering multiple dosages may also be used as needed to provide the desired level of protective immunity.

(b) Methods of Administration

In order to stimulate a preferred response of the GALT, NALT or BALT cells, administration of the vaccine composition directly into the gut, nasopharynx, or bronchus is preferred, such as by oral administration, intranasal administration, gastric intubation or in the form of aerosols, although other methods of administering the recombinant bacterium, such as intravenous, intramuscular, subcutaneous injection or intramammary, intrapenial, intrarectal, vaginal administration, or other parenteral routes, are possible.

In some embodiments, these compositions are formulated for administration by injection (e.g., intraperitoneally, intravenously, subcutaneously, intramuscularly, etc.). Accordingly, these compositions are preferably combined with pharmaceutically acceptable vehicles such as saline, Ringer's solution, dextrose solution, and the like.

In an exemplary embodiment, recombinant bacterium may be administered orally. Oral administration of a composition comprising a recombinant bacterium allows for greater ease in disseminating vaccine compositions for infectious agents to a large number of people in need thereof, for example, in Third World countries or during times of biological warfare. In addition, oral administration allows for attachment of the bacterium to, and invasion of, the gut-associated lymphoid tissues (GALT or Peyer's patches) and/or effective colonization of the mesenteric lymph nodes, liver, and spleen. This route of administration thus enhances the induction of mucosal immune responses as well as systemic and cellular immune responses.

In another embodiment, recombinant bacterium may be administered by coarse spray. The vaccines are administered by this whole-body spray route in an amount that is effective in eliciting an immune response, i.e. antibody and/or cellular immunity. Whole-body spray administration is surprisingly effective for vaccines comprising a live avirulent derivative of an enteropathogenic bacteria such as attenuated *Salmonella*. Spray administration of enteropathogenic bacteria avoids some of the disadvantages of other routes of administrations in that it does not require individual handling of chicks, it can be administered on day-of-hatch, and is easy to use under conditions normally found in commercial poultry production. The effective doses, which elicit an immune response, are roughly comparable to doses that are effective by the oral route of administration, such as administration in the drinking water.

III. Kits

The invention also encompasses kits comprising any one of the compositions above in a suitable aliquot for vaccinating a host in need thereof. In one embodiment, the kit further comprises instructions for use. In other embodiments, the composition is lyophilized such that addition of a hydrating agent (e.g., buffered saline) reconstitutes the composition to generate a vaccine composition ready to administer, preferably orally.

IV. Methods of Use

A further aspect of the invention encompasses methods of using a recombinant bacterium of the invention. For instance, in one embodiment the invention provides a method for modulating a host's immune system. The method comprises administering to the host an effective amount of a composition comprising a recombinant bacterium of the invention. One of skill in the art will appreciate that an effective amount of a composition is an amount that will generate the desired immune response (e.g., mucosal, humoral or cellular). Methods of monitoring a host's immune response are well-known to physicians, veterinarians, and other skilled practitioners. For instance, assays such as ELISA, and ELISPOT may be used. Effectiveness may be determined by monitoring the amount of the antigen of interest remaining in the host, or by measuring a decrease in disease incidence caused by a given pathogen in a host. For certain pathogens, cultures or swabs taken as biological samples from a host may be used to monitor the existence or amount of pathogen in the individual.

In another embodiment, the invention provides a method for eliciting an immune response against a *C. perfringens* antigen in a host. The method comprises administering to the host an effective amount of a composition comprising a recombinant bacterium of the invention.

In still another embodiment, a recombinant bacterium of the invention may be used in a method for eliciting an immune response against *C. perfringens* in a host in need thereof. The method comprises administrating to the host an effective amount of a composition comprising a recombinant bacterium as described herein. In a further embodiment, a recombinant bacterium described herein may be used in a method for ameliorating one or more symptoms of *C. perfringens* infection in a host in need thereof. For instance, a recombinant bacterium may be used to ameliorate one or more symptoms of necrotic enteritis. The method comprises administering an effective amount of a composition comprising a recombinant bacterium as described herein.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

The following examples illustrate various iterations of the invention.

Example 1

Alpha-Toxin Antigen Expressing Recombinant Bacteria

Materials and Methods

Bacterial strains and growth conditions. The bacterial strains used in this study are listed in Table 1. *Clostridium perfringens* CP995 and JGS4143 strains are type A strains originally isolated from the intestines of NE-affected chickens. CP995 was used for cloning the alpha toxin C-terminal domain, and JGS4143, (a hypervirulent strain), was used in the challenge experiments. Bacteria were grown in chopped meat broth (CMM) or brain heart infusion (BHI) medium with 0.04% D-cycloserine (BBL, Franklin Lakes, N.J.). Tryptose-sulfate-cycloserine (TSC) agar plates with 5% egg yolk (TSC-EY) or 5% sheep blood agar were used for colony differentiation based on lecithinase or hemolytic activity, respectively. Fluid thioglycolate medium (FTG) was used to cultivate large quantities of bacteria for animal inoculation and for bacterial resuscitation from tissue samples. All *C. perfringens* cultures were grown at 37° C. under anaerobic condition using BBL GASPAK systems. Both CP995 and JGS4143 were confirmed to be negative for $\beta_2$ toxin by PCR verification.

TABLE 1

| Bacterial strains and plasmids used in this study | |
|---|---|
| Strain or plasmid | Genotype and/or characteristics |
| Strains | |
| *S. enterica* serovar *Typhimurium* χ8914 | ΔpabA1516 ΔpabB232 ΔasdA16; vaccine vector |
| *E. coli* χ6097 | $F^-$ araD139 Δ(proAB-lac) λ-φ80dlacZΔM15 rpsL ΔasdA4 Δ(zhf-2::Tn10) thi-1; contains pYA232 ($Tc^r$, $lacI^q$); used for cloning and propagation of plasmid |
| *C. perfringens* CP995 | Type A, NE Isolate |
| JGS4143 | Type A, NE isolate, virulent strain |
| Plasmids | |
| pYA3493 | $P_{trc}$, asd, pBRori, bla SS; parent plasmid vector |
| pYA3620 | $P_{trc}$, asd, pBRori, bla SS, bla CT; parent plasmid vector pYA3493 with bla C-terminal fusions |
| pYA4101 | $P_{trc}$, asd, pBRori, ompA SS; parent plasmid vector with OmpA signal peptide fusion |
| pYA3977 | 375-bp DNA encoding PlcC in pYA3493 PlcC expression plasmid |
| pYA4110 | 375-bp DNA encoding PlcC in pYA4101 PlcC expression plasmid |
| pYA4149 | 375-bp DNA encoding PlcC in pYA3620 PlcC expression plasmid |
| pYA3910 | 375-bp DNA encoding PlcC in pBAD/HisB vector; used for His-tagged PlcC (rPlcC) expression |

*S. enterica* serovar *Typhimurium* x8914, containing defined attenuating deletions of the pabA and pabB genes, was used as the vaccine vector. χ8914 is derived from a highly virulent *S. enterica* serovar *Typhimurium* strain (χ3761). χ8914 has an oral 50% lethal dose of greater than $1\times10^9$ CFU for 1-day-old chicks, whereas the 50% lethal dose for the wild-type χ3761 is $3\times10^3$ CFU. χ8914 also has a deletion in the gene encoding aspartate β-semialdehyde dehydrogenase (asd), which renders it deficient in the synthesis of diaminopimelic acid (DAP). Since DAP is an obligate component of the cell wall peptidoglycan, in the absence of exogenously supplied DAP the growth of χ8914 strictly depends on the complementation of the asd mutation with the vaccine antigen expression plasmid that carries the *Salmonella* asd gene. This dependence on $Asd^+$ plasmid complementation is the basis for the balanced lethal host-vector system, which abrogates the need for antibiotic resistance markers. Bacteria were grown at 37° C. in Luria-Bertani (LB) culture medium containing 0.1% dextrose. When required, 50 μg/ml DAP was added.

Cloning of the *C. perfringens* pkC Gene.

*C. perfringens* DNA was isolated from a bacterial lysate prepared from colonies grown overnight on TSC agar plates. Bacteria were suspended in 150 μl 0.5 M NaOH, pH 8.5, incubated for 30 min at room temperature, and diluted with 25 μl Tris-Cl, pH 7.4, and 425 μl water. A 375-bp region of the alpha toxin gene (plc) encoding the carboxy-terminal end of the alpha toxin (amino acids 248 to 370) was PCR amplified from the CP995 lysate using standard PCR conditions with the following primer sequences: 5'-CGGAATTCGATCCATCAGTTGGAAAGAATGTA-3' (SEQ ID NO:1) and 5'-CCGAAGCTTATTATTTTATATTATAAGTTGAATTTCC-3' (SEQ ID NO:2). For the sequence analysis of the complete alpha toxin gene from CP995, primers binding to flanking regions of plc, 5' AGTTTAACAATTTAGAGTGGGTAAGGTTAGATGTG 3' (SEQ ID NO:3) and 5' GCCAGCTCCTAGGAATCCTGAAATTATATCTAC 3' (SEQ ID NO:4), were used.

rPlcC protein preparation. The PCR product of plcC, the alpha toxin C-terminal domain-encoding sequence, was first cloned into the pBAD/HisB plasmid vector (Invitrogen, Carlsbad, Calif.) for the expression of a His-tagged recombinant PlcC (rPlcC) protein. The plasmid pYA3910 (pBADHisB containing plcC) (Table 1) was electroporated into competent *Escherichia coli* TOP10 cells (Invitrogen, Carlsbad, Calif.). The expression of His-tagged rPlcC in the TOP10 cells (pYA3910) was induced by adding 0.02% L-arabinose into early-log-phase growing bacteria. Bacteria were harvested from a 250-ml culture at an optical density at 600 nm ($OD_{600}$) of 1.2 by centrifugation at 5,000×g for 15 min. The cell pellet was resuspended in 40 ml cell lysis solution (Sigma, St. Louis, Mo.), which contains lysozyme (0.2 mg/ml), benzonase (50 U/ml), and protease inhibitors. Following 15 min of incubation at room temperature in the lytic solution, the bacterial suspension was briefly sonicated (2 min) to ensure cell disruption. Insoluble material was removed by centrifugation at 16,000×g for 10 min. The supernatant containing His-tagged protein was loaded onto 0.8-by 4-cm chromatography columns (Bio-Rad, Hercules, Calif.) packed with nickel-SEPHAROSE gel (6%) (Sigma, St. Louis, Mo.). The affinity gel matrix was washed with 50 mM $NaH_2PO_4$, pH 8.0, 0.3 M NaCl solution before and after the bacterial lysate was loaded. Proteins were eluted with 200 mM $C_3H_4N_2$ (imidazole) in the washing solution. The elute was desalted and concentrated by a CENTRICON filtration system using 5,000 (5K) and 50K nominal molecular weight membranes (Millipore, Billerica, Mass.). Protein was analyzed by electrophoresis on a 12% Tris-Bis gel (see FIG. 1) and by Western blotting using 6-HisG antibody (Invitrogen, Carlsbad, Calif.). The protein concentration was determined by a Bradford assay using bovine serum albumin as the standard. To produce rabbit anti-PlcC antibody, two rabbits were injected subcutaneously (s.c.) with 100 .mu.g rPlcC protein emulsified in Freund's adjuvant. The rabbits were immunized three times, with 2-week intervals between injections, and the antiserum was tested for specific reactivity against rPlcC by immunoblot analysis (see FIG. 1).

Plasmids for PlcC Expression in the *S. enterica* Serovar Typhimurium Vaccine Strain.

Figure 2A:
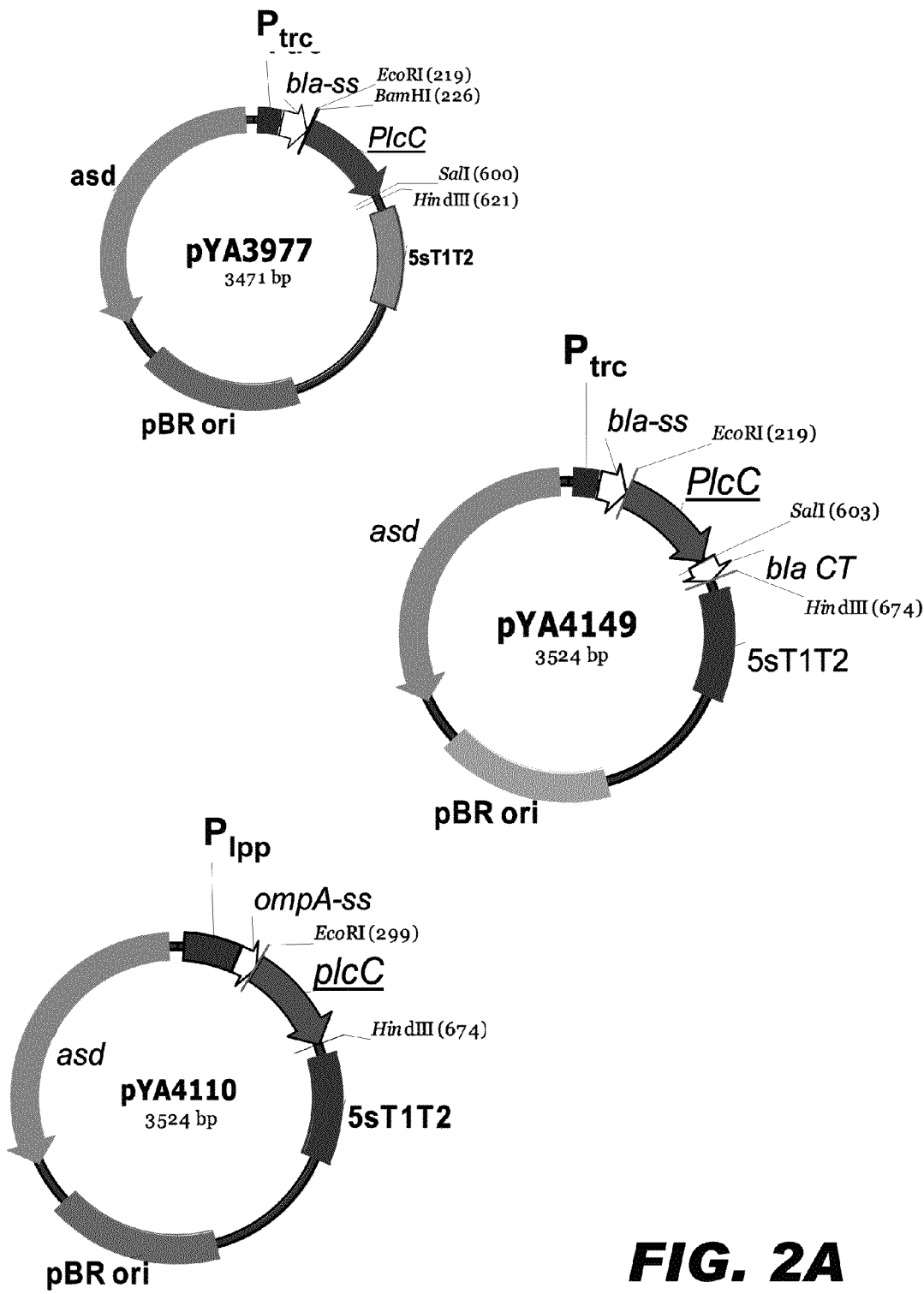
FIG. 2 depicts PlcC vaccine antigen expression plasmids. (A) Plasmid maps for the pYA3977 $P_{trc}$ bla signal peptide sequence (ss) vector, pYA4149 $P_{trc}$ bla ss and bla C-terminal sequence (CT) fusion vector, and pYA4110 $P_{lpp}$ ompA ss vector. (B) The sequences of $P_{trc}$ (SEQ ID NO:5), $P_{lpp}$ (SEQ ID NO:10), bla ss (nucleic acid SEQ ID NO:6; amino acid SEQ ID NO:7), ompA ss (nucleic acid SEQ ID NO:11; amino acid SEQ ID NO:12), and bla CT (nucleic acid SEQ ID NO:8: amino acid SEQ ID NO:9). RBS, ribosome binding site (Shine-Dalgarno sequence). Arrows show predicted signal peptide cleavage sites.

Three different recombinant gene expression plasmids, pYA3493, pYA3620, and pYA4101, were used for the expression of PlcC by the *S. enterica* serovar Typhimurium vaccine strain (Table 1). The plasmids contain a modified $P_{trc}$ or $P_{lpp}$ promoter and a signal peptide sequence from *E. coli* class A β-lactamase (bla) or the outer membrane protein A (ompA) at the translation start site for the cloned antigen (FIG. 2). The $P_{trc}$ or $P_{lpp}$ promoter directs the constitutive expression of the recombinant PlcC in *Salmonella*. The signal peptides target the protein for secretion by the type II secretion pathway into the periplasm, with subsequent release into the culture supernatant. In addition to the β-lactamase signal peptide sequence, pYA3620 also has the β-lactamase C-terminal protein-coding sequence at the 3' end of the recombinant gene. Such a fusion of the C-terminal peptide sequence of β-lactamase to the recombinant protein has been reported to facilitate the transport of recombinant protein across membranes. PlcC expression plasmids pYA3977, pYA4110, and pYA4149 (Table 1) were propagated, and PlcC expression was confirmed first in *E. coli* strain χ6097. Protein expression in χ6097 was induced by 0.5 mM isopropyl-β-D-thiogalactopyranoside. Once PlcC expression was confirmed by sodium dodecyl sulfate-polyacrylamide gel electrophoresis (SDS-PAGE) and Western blot analysis, the plasmids were recovered from *E. coli* and introduced into competent χ8914 by electroporation. As a vaccine control strain (designated the RAS control), the parent plasmid pYA3493 was similarly introduced into χ8914. To verify plasmid stability, the vaccine strain harboring the expression plasmid was grown for more than 50 generations under nonselective conditions (i.e., in the presence of DAP) and then was tested for growth on medium without DAP.

Expression of PlcC protein by the *S. enterica* serovar Typhimurium vaccine vector. RASV strains were grown overnight in 5 ml LB broth. The next day, cultures were inoculated into 100 ml LB broth and grown with aeration at 200 rpm until the culture reached an $OD_{600}$ of 0.8. To test the expression of rPlcC as a cytoplasmic soluble protein, 1 ml of the culture was transferred to a microcentrifuge tube and centrifuged for 3 min at 14,000×g, and the pellet was resuspended in 500 .mu.l Tris-HCl buffer (50 mM Tris-HCl, 100 mM NaCl, pH 7.2, 10 mM β-mercaptoethanol, and 2 mM phenylmethylsulfonyl fluoride). Bacteria were lysed by sonication, and insoluble protein was removed by centrifugation at 14,000×g for 2 min. The supernatant was tested for rPlcC. To evaluate PlcC protein localization in the periplasm and secretion into culture supernatant, bacteria were harvested from a 100-ml culture by centrifugation at 4,000×g for 15 min at 4° C. Subcellular fractionation for periplasm contents was performed using the lysozyme digestion of the bacterial pellet by osmotic shock with sucrose as previously described. The culture supernatant was filtered through a 0.22-μm filter and concentrated by precipitation overnight at 4° C. in a 10% trichloroacetic acid (TCA) solution. The protein samples were analyzed by SDS-PAGE and Western blotting. Specific protein bands with the predicted molecular masses were distinguished by the COOMASSIE blue staining of the SDS-PAGE and the immunoblots using rabbit anti-PlcC hyperimmune serum. The amount of PlcC expression was estimated from the SDS-PAGE bands based on comparisons of their densitometry data to those of a known concentration of bovine serum albumin. To ensure the absence of cell lysis that could confound the secreted proteins recovered from culture supernatants and to control the preparation of periplasmic protein, β-galactosidase was used as a cytoplasm protein marker. The MudJ allele (atrB13::MudJ) was inserted into the *S. enterica* serovar Typhimurium vaccine strain [χ8914(pYA3977)]chromosome by transduction. β-Galactosidase production by the χ8914(pYA3977) atrB13::MudJ construct was used as a cytoplasm protein marker. The culture supernatant, periplasm, and cytoplasm fractions from this construct were analyzed by Western blotting using anti-β-galactosidase antibody (Sigma, St. Louis, Mo.).

RASV Inoculum Preparation.

RASV strains from −80° C. stock were spread on LB agar. Five colonies were inoculated into 5 ml broth and grown statically overnight at 37° C. The following day, the whole culture was inoculated into 100 ml prewarmed LB broth in a 500-ml culture flask and grown with constant shaking at 200 rpm to an $OD_{600}$ of 0.8 (about 5 h of culture). Bacteria were harvested by centrifugation at 4,000×g for 15 min at room temperature, and the pellet was resuspended in buffered saline with 1% gelatin (BSG) solution. The volume of the bacterial culture and BSG for resuspension was calculated to yield a bacterial concentration of $2\times10^9$ CFU/ml. Chickens were inoculated orally with 0.5 ml of the suspension, which contained $1\times10^9$ CFU.

Chicken Immunization.

One-day-old Cornish×Rock chicks were purchased from McMurray Hatchery (Webster City, Iowa). On arrival three chicks were euthanized, and samples of internal organs were aseptically collected to test for *S. enterica* serovar Typhimurium infection by bacterial culture on MacConkey agar plates. Chicks were divided into separate Horsfall isolators, with 10 chicks per Horsfall. On the second day (3 days of age), all chicks, except for those of one group, were orally inoculated (using an oral gavage needle) with 0.5 ml bacterial suspension containing $10^9$ CFU of either RASVs or the RAS control strain [χ8914(pYA3493)]. To facilitate the passage of the inoculum to the intestines, chickens were deprived of feed and water for 8 h prior to inoculation, and feed and water were returned 1 h after the RASV inoculation. Ten days later, a similar second dose was given as a boost immunization. One group of chickens was injected s.c. in the neck with 50 μg rPlcC protein in a 100-μl suspension of complete Freund's adjuvant. These chickens received a boost immunization 14 days later with the same dose but with incomplete Freund's adjuvant.

In a prior experiment, chickens were immunized with two doses of RASV χ8914(pYA3977), χ8914(pYA4110), or χ8914(pYA3493) and by s.c. rPlcC injection, and 5 weeks later (7 weeks of age) all the chickens were given a late boost immunization with rPlcC by s.c. injection. The chickens were administered 50 μg protein in a 100-μl volume suspension emulsified in incomplete Freund's adjuvant. This experiment, oral RASV priming followed by a parenteral protein boost immunization, was carried out to evaluate the effect of primary immunization with RASV ora subunit vaccine on antibody titers. RASV-3 was not included in this experiment.

Chickens were fed an antibiotic-free corn-based starter diet or a wheat/barley-based grower's diet (Purina Mills, St. Louis, Mo.). Feed and water were provided ad libitum. In the first week, chicks were reared at a brooding temperature of 32° C. with 24 h of light. Subsequently, the cage temperature was kept at 25° C. and the light schedule modified to 16 h of light and 8 h of dark.

All of the animal experiments detailed above were conducted with the permission and under the guidelines of the Arizona State University Institutional Animal Care and Use Committee.

*Clostridium perfringens* Challenge.

Two weeks after RASV immunization, the chicken feed was replaced by a wheat- and barley-based formulated growers' diet, which has higher crude protein and neutral fiber content. After 1 week on the grower diet, chickens were challenged by oral inoculation and repeated infection through contaminated feed with *C. perfringens* strain JGS4143. On the first day of the challenge, chickens were orally gavaged with 2 ml of an overnight culture of *C. perfringens* in CMM. Contaminated feed was prepared by mixing an overnight culture with feed as formerly described. Briefly, *C. perfringens* was grown in 10 ml CMM broth for 18 h at 37° C., which then was inoculated into 1 liter of FTG and grown for 18 h. The FTG culture was mixed with feed at a wt/vol ratio of 1:1. The bacterial feed mix was freshly prepared twice per day and was provided to the chickens for four consecutive days. The average number of bacteria in the 18-h FTG culture was $1 \times 10^9$ CFU/ml, and shortly after being mixed with feed, $10^7$ CFU/g feed was recovered, which declined to $10^2$ to $10^3$ CFU/g feed after 10 h on the feeder. One day after the end of the challenge infection, five birds were euthanized by $CO_2$ inhalation for postmortem examination. The remaining five chickens were used for delayed-type hypersensitivity (DTH) assays and euthanized five days later. Individual body weights were measured before and after challenge infections.

*S. enterica* Serovar *Typhimurium* Vaccine Strain and *C. perfringens* Isolation from Chickens.

One week after RASV boost immunization, cloacal swabs were collected for bacteriology to assess RASV shedding. Dilutions of cloacal swabs were spread on MacConkey agar plates with 1% lactose. The RASV strain was identified by PCR on randomly selected *S. enterica* serovar *Typhimurium* colonies using primers that anneal to plcC and the promoter region of the expression plasmid. The cloacal swab preparations also were spread on TSC-EY agar plates and incubated in an anaerobic jar to identify lecithinase-positive (*C. perfringens*) colonies. After challenge infection with *C. perfringens*, segments of the ileum and cecum with the intestinal contents were aseptically collected and homogenized in BSG. Tissue homogenates were diluted in BSG and spread on MacConkey agar plates for *S. enterica* serovar *Typhimurium* detection and on TSC agar plates for *C. perfringens* detection.

Measuring antibody responses. Blood samples were collected weekly by wing vein puncture, and bile samples were collected during autopsy. Serum immunoglobulin G (IgG) and bile IgA responses were measured by indirect enzyme-linked immunosorbent assay (ELISA). Briefly, microtiter plates (Nunc, Roskilde, Denmark) were coated with 10 μ/ml (1 μg/well) of purified rPlcC protein diluted in coating solution ($Na_2CO_3$, 1.6 g; $NaHCO_3$, 2.9 g; $NaN_3$, 0.2 g; all in 1 liter distilled $H_2O$). Plates were incubated overnight at 4° C., dried, and washed in phosphate-buffered saline (PBS)-0.2% TWEEN 20 (washing solution). Nonspecific binding was blocked by using SEA BLOCK blocking buffer (Pierce, Rockford, Ill.) for 1 h at 37° C. Test samples (serum or bile) were twofold diluted in blocking buffer, added in duplicate, and incubated at 37° C. with agitation. After repeat washes, biotinylated goat anti-chicken IgG or IgA heavy plus light chain antibody (Bethyl Laboratories, Montgomery, Tex.) was added (1:5,000 dilution) and incubated for 1 h at 37° C. Plates were washed, streptavidin-horseradish peroxidase solution (Southern Biotech, Birmingham, Ala.) (1:5,000 dilution) was added, and the plates were incubated for an extra 1 h at 37° C. Peroxidase activity and color development were detected by 2-2'-azino-di-(3-ethylbenzthiazoline sulfuric acid) (ABTS) substrate (Sigma, St. Louis, Mo.) containing 0.03% $H_2O_2$ in citrate buffer, pH 4.35. Plates were incubated for 10 min at 37° C. for color development, and the reaction was stopped with 1% SDS solution. The OD of each well's contents was measured at 405 nm using a microplate reader (Molecular Devices, Sunnyvale, Calif.). A volume of 100 μl/well of the test samples, antibodies, or washing solutions was used in each steps. The antibody response in the serum also was tested by the immunoblot analysis of immunized chicken sera against alpha toxin obtained from concentrated culture supernatant of *C. perfringens* and rPlcC proteins.

Alpha toxin neutralization test. The neutralization of alpha toxin by serum antibody was determined by the inhibition of red blood cell (RBC) hemolysis by alpha toxin. RBCs were prepared by washing samples of freshly collected rabbit blood twice in PBS and diluting them to 2% (vol/vol) in PBS containing 3 mM $CaCl_2$. Alpha toxin was obtained from the supernatant of a *C. perfringens* culture grown overnight by sequential filtration through 100- and 10-kDa AMICON Ultra filters (Millipore, Billerica, Mass.). The enzymatic activity of the culture supernatant concentrate was evaluated and quantified using a phosphatidylcholine-phospholipase C assay kit (Invitrogen, Carlsbad, Calif.). The concentrated culture supernatant was diluted in PBS containing 0.1 mM $CaCl_2$, and 100 μl aliquots containing an estimated 250 ng protein (about 200 U) were distributed into a 96-well dilution plate. Purified recombinant alpha toxin (250 ng) (Sigma, St. Louis, Mo.) was included as a control. Test sera (pooled serum samples) were twofold diluted in PBS (1:10, 1:20, and 1:40), and 100 μl was added into wells. Control wells contained either serum with no toxin or alpha toxin alone. Well contents were mixed and incubated for 1 h at 37° C. with slow agitation. After 1 h, 100 μl of the 2% RBC solution was added into each well. After incubation for 2 h at 37° C., plates were chilled for 15 min at 4° C. and briefly centrifuged at 500×g to sediment intact cells (i.e., RBCs). The absorbance of well contents was measured at 540 nm using a microtiter plate reader. As a reference, 100% RBC lysis was obtained by adding 50 μl of 1% TRITON X-100 to wells containing serum and RBCs, while 100% lysis inhibition was recorded from wells without alpha toxin. The hemolysis or inhibition of cell lysis was expressed as the percent difference of the absorbance of wells with test sample, and control wells with half-diluted alpha toxin without a test sample.

DTH Assay.

Four weeks after the RASV boost immunization and 3 days after the challenge infection, five chickens per group were injected intradermally with 20 μg of the rPlcC protein in 50 μl saline into the left footpad at the toe web between the first and second digits. The right foot was injected with sterile saline as a negative control. The thickness of the toe web was measured with a digital micrometric caliper at 48 and 72 h after antigen or saline injection. Data were expressed as the difference between results for the left foot and the right foot (control).

Serum Bacteriostatic (Growth Inhibition) Assay.

Figure 4:
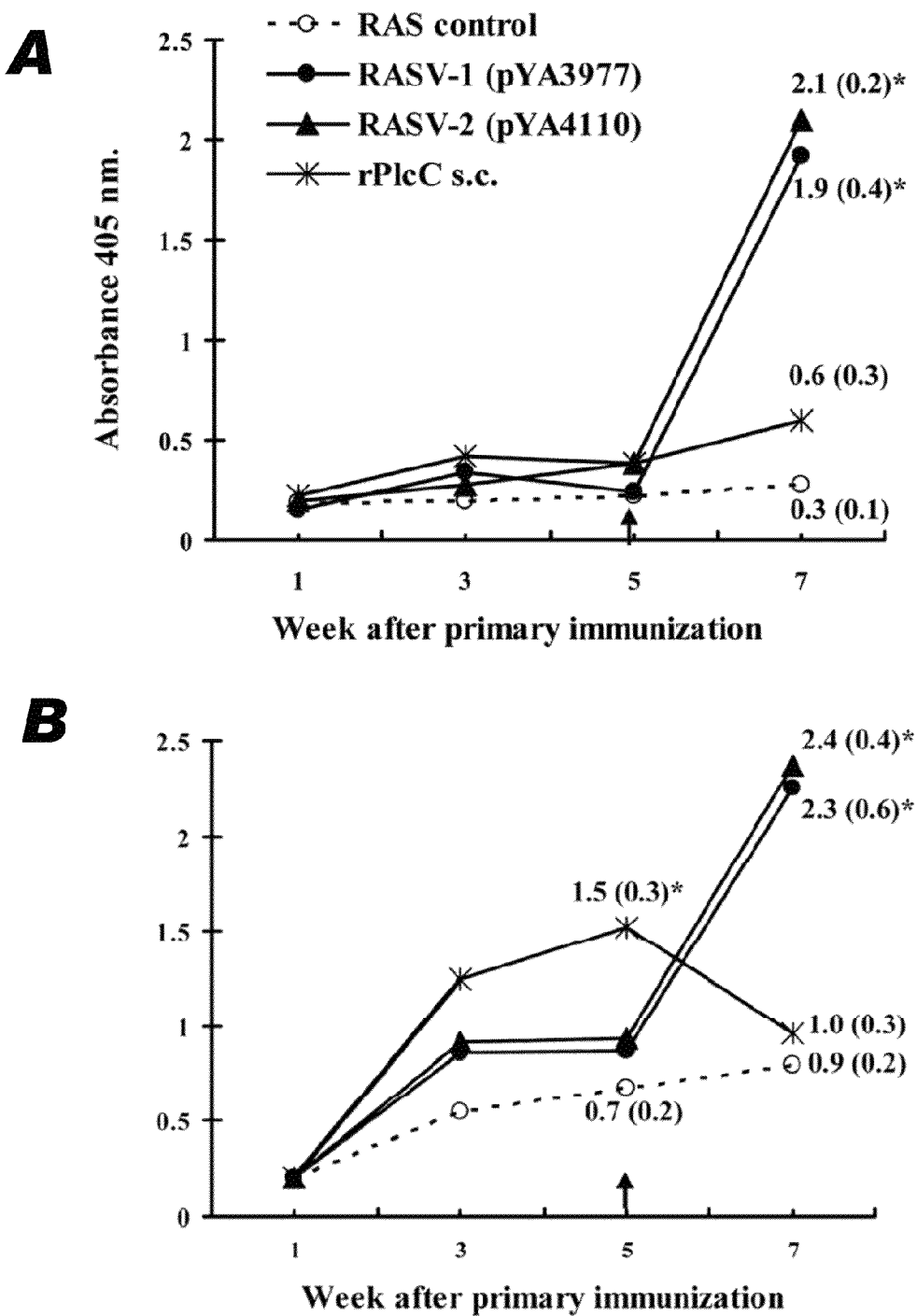
FIG. 4 depicts ELISA results of anti-PicC serum IgG (A) and bile IgA (B) responses in chickens immunized with oral RASV or s.c. rPlcC emulsified in 100 μl Freund's complete adjuvant. Five weeks after the primary immunization with either RASV or s.c. rPlcC, all of the chickens were given an s.c. boost injection with 50 μg purified rPlcC protein emulsified in 100 μl incomplete Freund's adjuvant. Arrows point to the time of injection with rPlcC protein. Sera were tested at 1:80 dilutions, and bile samples were tested at 1:100 dilutions. The average absorbance of serum or bile samples from five chickens per group at each time point is shown. Values are indicated, with standard deviations in parentheses, for points that show significant mean differences from results for the RAS control group [χ8914(pYA3493)]. *, P<0.05.
Figure 5:
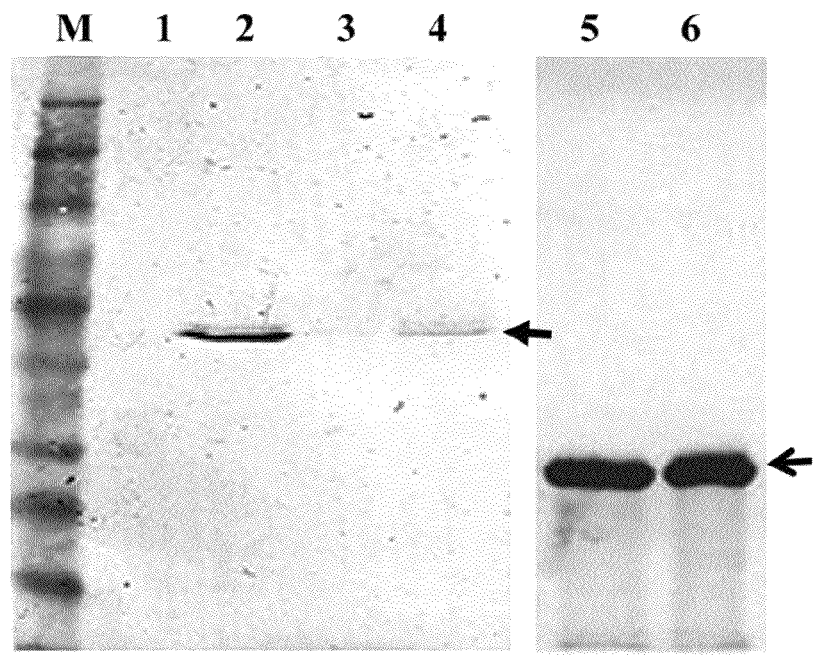
FIG. 5 depicts an immunoblot of *C. perfringens* culture supernatant and rPlcC with χ8914(pYA3977)-immunized chicken serum. Sera collected at 2 weeks after the boost immunization were pooled and used at a 1:40 dilution. *C. perfringens* culture supernatant was concentrated in 10% TCA (denaturing condition) or concentrated by fil FIG. 18A,B depicts the optimized GDP sequence (SEQ ID NO:27 is the sense nucleic acid; SEQ ID NO:28 is the reverse complement; SEQ ID NO:29 is the amino acid sequence).
Figure 6:
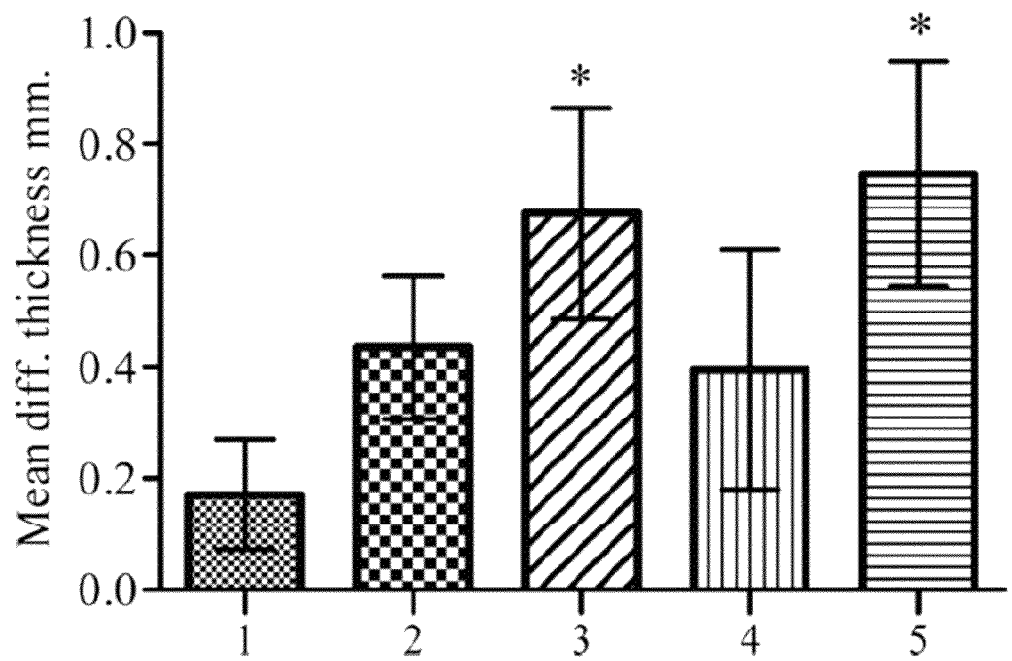
Figure 7:
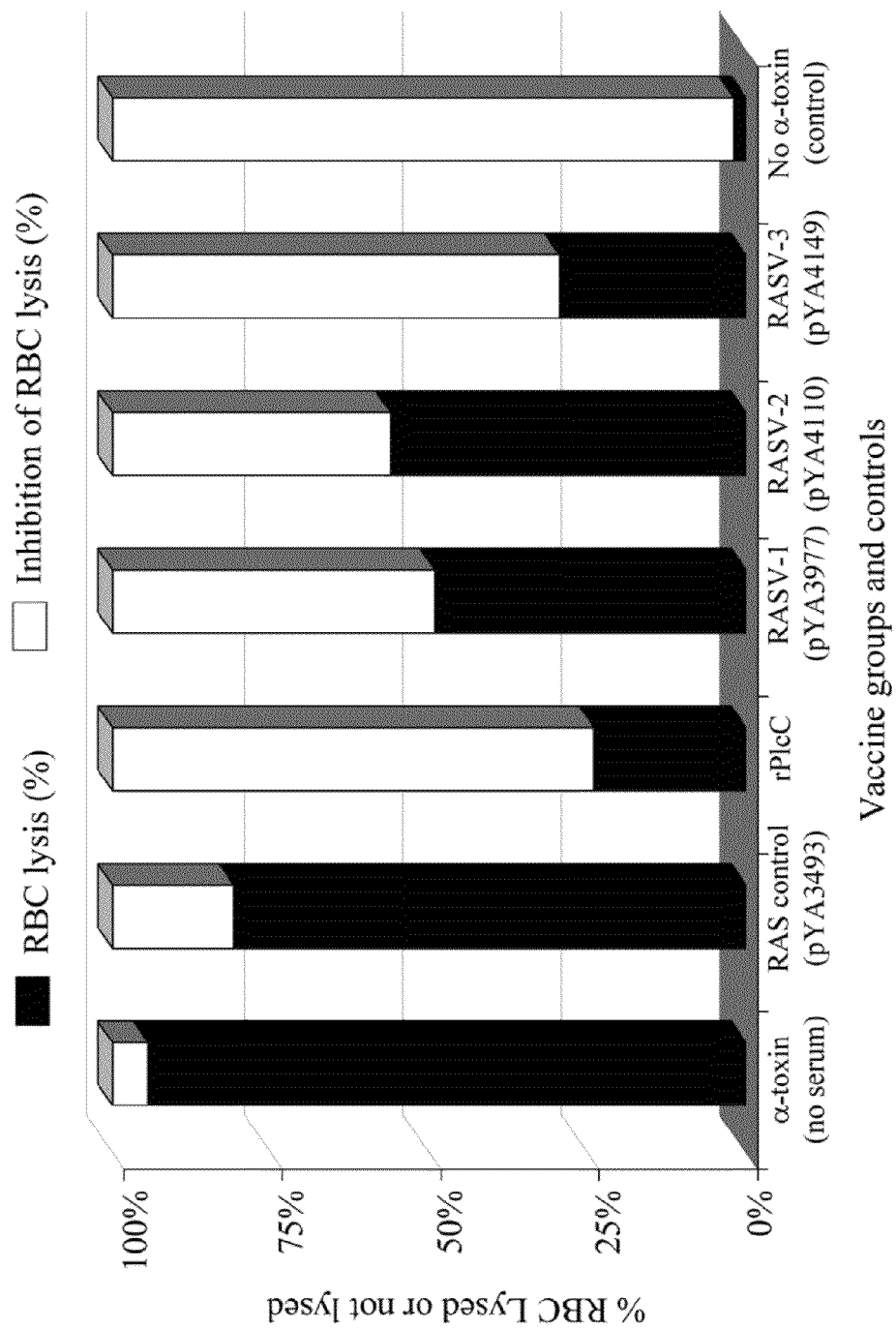

Sera from immunized or control chickens were filtered through 0.45-μm pore filters, decomplemented by being heated at 56° C. in a water bath for 30 min, and added into the CMM broth culture at 1:20 and 1:40 final dilutions. A volume of 100 μl overnight culture of *C. perfringens* diluted to a concentration of $10^5$ CFU per ml was added into 1 ml of culture medium containing serum, and the cultures were incubated anaerobically at 37° C. The growth of bacteria was monitored by the culture OD, and the number of CFU was monitored by plating serial dilutions on TSC-EY agar plates at 12 and 18 h.

Immunofluorescence microscopy. An indirect immunofluorescence test was performed to determine if antibody against PlcC binds to the bacterial cell surface. Formalin-inactivated bacteria or a fresh colony of *C. perfringens* from an overnight TSC-EY plate was spread on microscope slides. The formalin inactivation of bacteria was carried out by incubating washed bacterial cells (from a 24-h culture of JGS4143 in BHI broth) in 3 mM formaldehyde solution in PBS for 2 h at 37° C., followed by overnight incubation at room temperature with slow agitation. The suspension (10 ml) was centrifuged at 5,000×g for 15 min, and the pellet was washed twice and resuspended in PBS. Live cells were spread on slides from colonies and were killed and fixed by being heated. Slides were dried and covered with PBS containing 1% bovine serum albumin and incubated for 1 h at room temperature in a humidified box. The blocking solution was removed, and 200 μl of the test serum from immunized or control chickens diluted 1:50 in PBS was spread onto the slide and covered with a coverslip. Slides were incubated overnight at 4° C. After being washed with PBS-0.1% TWEEN 20, goat anti-chicken IgG antibody conjugated with fluorescein isothiocyanate (Southern Biotech, Birmingham, Ala.) was added, and the solution was incubated for an extra 2 h at room temperature. Slides then were washed three times in PBS-0.1% TWEEN 20, dried, and observed under a fluorescence microscope.

Pathological Examination.

Autopsies were performed 24 h after the last day (i.e., the fourth day) of the challenge infections. The whole intestines were examined for gross lesions such as hemorrhagic spots, mucosal paleness or discoloration, swelling, feebleness of the intestinal wall, and the nature of the contents. Tissue samples of the duodenum, midjejunum, and ileum from similar segments (i.e., located at identical distances from the Meckel diverticulum mark) were collected in buffered 4% formaldehyde for histopathology. Sections of the intestinal tissues were stained with hematoxylin and eosin and were examined for microscopic lesions of enteritis and tissue morphological alterations. Villus epithelial degeneration, sloughing, and inflammatory leukocyte infiltration into lamina propria and submucosa were examined, as was villus shortening. The severity and distribution of lesions were graded semiquantitatively by using a scale (0 to 5) that considers the severity and distribution of the lesions based on prior knowledge of normal histology and severe NE lesions. The scores were given as follows: 0, no lesion; 1, scattered mild degeneration of villus tip epithelium; 2, mild degeneration detected uniformly in several microscopic fields; 3, moderate necrotic lesions with epithelial sloughing, degeneration, and leukocyte infiltrations; 4, severe epithelial degeneration and necrosis dispersed in several microscopic fields; and 5, severe and frequent necrotic lesions, often with villus shortening or atrophy.

Statistical Analysis.

The differences in body weights were evaluated by two-way analysis of variance with the Bonferroni posttest method. One-way analysis of variance and the Bonferroni posttest were used to compare the differences in ELISA (absorbance) and DTH data. A P value of less than 0.05 was considered significant. The analyses were performed using the GraphPad Prism program.

Amino Acid Sequence of Alpha Toxin.

The primary structure of alpha toxin from NE isolate CP995 shows 98% sequence identity to the type A reference strain ATCC 13124 (GenBank accession no. M24904), with a few amino acid substitutions ($Leu_{16}$ to Thr, $Lys_{17}$ to Gln, $Ala_{174}$ to Asp, $Thr_{177}$ to Pro, $Ser_{335}$ to Pro, $Gly_{363}$ to Arg, and $Asn_{364}$ to Lys) and a deletion of $Ile_{21}$ (FIG. 3). Except for the absence of $Ile_{21}$, the amino acid substitutions at the specific sites are common variations among type A isolates from humans and animals. These variations do not affect alpha toxin's phospholipase C and hemolytic activities or hinder the neutralizing ability of C terminus-specific antibody against alpha toxin.

PlcC expression in *S. enterica* serovar *Typhimurium* vaccine vector. The expression of the PlcC protein in the *S. enterica* serovar *Typhimurium* vaccine strain was detected on the SDS-PAGE gel stained with COOMASSIE blue (FIG. 1). High levels of PlcC expression were obtained with all three plasmid constructs. The PlcC protein concentration was estimated at roughly 100 ng/μl bacterial lysate, as measured by a densitometry analysis that compared the results to those for a standard concentration of bovine serum albumin CHEMIDOC XRS; Bio-Rad, Hercules, Calif.). PlcC was effectively secreted by the *S. enterica* serovar *Typhimurium* vaccine strains through a type II secretion system. The fusion with the OmpA or Bla signal peptide sufficiently enabled the transport of PlcC into the periplasm, which then was secreted across the outer membrane into the culture supernatant. No β-galactosidase was detected in the culture supernatant of the RASV χ8914 (pYA9977)atrB13::MudJ strain, thus indicating that bacterial lysis had not occurred.

The molecular masses of PlcC expressed from the three constructs appear different due to differences in the sizes of the signal peptides, the linker amino acids, and the β-lactamase C-terminal fusion in pYA4149 constructs (FIG. 2). Accordingly, the molecular mass of PlcC was 16 kDa in χ8914(pYA3977), 14 kDa in χ8914(pYA4110), and 18 kDa in χ8914(pYA4149). The molecular mass of the His-tagged rPlcC was 19 kDa.

Antibody Responses in Immunized Chickens.

RASV-immunized chickens generally had low serum antibody responses, as measured by ELISA, at serum dilutions as low as 1:40. Unexpectedly, chickens that received s.c. immunization with rPlcC also showed a low serum IgG response similar to that of RASV-immunized chickens. Formerly, we tested whether RASV or rPlcC immunization gives some priming effect when followed by a boost protein immunization at a later time point. When the chickens were injected with 50 µg of purified rPlcC protein 5 weeks after the primary immunization (i.e., at 7 weeks of age), chickens that first were immunized with RASV developed a significant and rapid increase in antibody titers (i.e., in comparison to the typical response pattern), whereas those immunized with rPlcC injection had low titers compared to those of the RASV groups (FIG. 4A). The rPlcC-immunized chickens had a higher initial bile IgA titer, which abruptly declined after the final boost with rPlcC. In the RASV-immunized chickens, the IgA titers increased significantly after the rPlcC boost (FIG. 4B). This strong antibody response in the RASV prime and protein boost approach shows that although there were low levels of serum antibody titers generated by the primary immunization, RASV stimulates an immune reaction that produces a better memory response than repeated immunization with protein alone.

Because our goal is to develop an oral RASV, we immunized a second group of birds with RASV and performed a more complete evaluation of immune responses and *C. perfringens* challenge to assess the protective efficacy. Sera from the RASV-immunized chickens were tested by Western blotting on SDS-PAGE-separated rPlcC and the whole alpha toxin, and both PlcC protein and the complete alpha toxin obtained from the culture supernatant of *C. perfringens* were detected (FIG. 5). This confirmed the presence of serum antibody responses in RASV-immunized chickens. Sera from the RASV- or rPlcC-vaccinated chickens reacted positively with the whole alpha toxin, whether it was denatured by TCA precipitation or not (i.e., concentrated by filtration) prior to separation on SDS-PAGE.

DTH Reaction.

RASV-immunized chickens showed an increase in DTH responses compared to those of the chickens inoculated with the control *S. enterica* serovar *Typhimurium* vector strain (FIG. 6). The highest DTH reaction level ($P<0.05$) was induced in chickens immunized with χ8914(pYA4110) or s.c. rPlcC at 48 h after PlcC injection. At 72 h after PlcC injection, the DTH responses in all immunized chickens were similar to each other and were higher than those of the control chickens ($P>0.05$). The role of cell-mediated immunity in NE is not clear; however, since *S. enterica* serovar *Typhimurium* replicates intracellularly within antigen-presenting cells, it presumably facilitates the delivery of recombinant antigens by the endogenous antigen presentation pathway to prime $CD4^+$ T cells and the cell-mediated response. DTH is commonly used as an index for cellular responses.

Alpha Toxin Neutralization.

Toxin neutralization by serum antibody was measured as a function of alpha toxin-induced RBC lysis. Pooled sera from chickens immunized with RASV or rPlcC inhibited the hemolytic effect of the alpha toxin in a *C. perfringens* culture supernatant (FIG. 7). The highest level of RBC lysis inhibition was observed with sera from birds vaccinated with rPlcC and RASV-3 [χ8914(pYA4149)], with inhibitions of 76 and 71%, respectively. The sera from chickens immunized with the other RASVs (RASV-1 and RASV-2) also showed more than 50% reductions in RBC lysis compared to that of the RAS-immunized (control) chicken serum. These results indicate the presence of alpha toxin-neutralizing antibodies in RASV-immunized chickens.

*C. perfringens* Growth Inhibition by Immunized Chicken Serum.

Decomplemented sera from immunized chickens inhibited the proliferation of *C. perfringens* growth in culture (Table 2). Bacterial growth in cultures containing serum from either RASV- or rPlcC-immunized chickens was suppressed by up to 1,000-fold compared to that of cultures with serum from control nonimmunized chickens.

Immunofluorescence Microscopy.

Antibodies binding to bacterial surface proteins or capsules are known to inhibit bacterial growth and to facilitate opsonophagocytosis. To investigate the inhibitory effects of the sera from immunized chickens, we evaluated the possibility of surface binding by serum antibody by using an indirect immunofluorescence assay. Remarkably, serum antibody against PlcC from immunized chickens showed binding to the surface of whole bacteria (FIG. 8). Higher levels of fluorescence were frequently detected at bacterial poles.

Isolation of the RASV Strain and *C. perfringens* from Chickens.

The *S. enterica* serovar *Typhimurium* vaccine strain was readily detected in cloacal swabs collected 1 week after the boost immunization and in the intestinal segments (from the ileum and cecum) collected during autopsy at 3 weeks after immunization. The average *S. enterica* serovar *Typhimurium* numbers in cloacal swabs were $1\times10^4$ CFU/g of fecal material, and 3 weeks later the numbers in the ileum and in the cecum were, on average, $1\times10^2$ and $1\times10^4$ CFU per gram of tissue, respectively. No *S. enterica* serovar *Typhimurium* was detected in the liver or spleen at 3 weeks after immunization.

*C. perfringens* could not be detected from cloacal swab samples collected prior to the challenge infection. Usually, a small number of *C. perfringens* (resident flora) cells are identified by culture from healthy young birds, especially in birds reared under experimental conditions. After the challenge infection, generally smaller numbers of *C. perfringens* were detected from intestines, even at 1 day after the challenge infection. The average numbers of *C. perfringens* cells detected in the intestines were less than $1\times10^3$ and $1\times10^5$ CFU/g in the ileum and cecum, respectively. Five days after the end of the challenge infection, the numbers in cecum declined to less than $10^3$ CFU/g, and none could be recovered from the ileum. The numbers of *C. perfringens* cells recovered were highly variable among chickens in all groups, and there was no correlation between the number of bacteria isolated from an intestinal segment and lesion development.

Intestinal Mucosal Lesion Development after Challenge Infection.

Gross lesions with mucoid intestinal luminal content, feeble intestinal walls, mucosal edema, and hemorrhagic spots were found in the duodenum and proximal jejunum of nonimmunized chickens (FIG. 9A). Overall, few chickens showed overt gross lesions and diarrhea. Histopathology lesions such as hyperemia of the lamina propria, villus tip epithelium degeneration, villus shortening, disruption of the structural integrity of enterocytes with the basement membrane, and inflammatory leukocyte infiltration were observed mainly in the jejunum. These lesions were observed 1 day after challenge predominantly in nonimmunized chickens. The hematoxylin- and eosin-stained sections also revealed clusters of *C. perfringens* in the intestinal lumen and mucosal surfaces that were seldom attached to epithelial surfaces (FIG. 9E). Sites with bacterial clumps often depicted a mild defect of the epithelial surface and microvilli mostly in nonimmunized or control RAS-immunized chickens. The lesions were severe and more frequent in nonimmunized (control) chickens, while immunized chickens had minimal lesions in a few chickens (Table 3). The histopathological lesions had receded by 4 days after challenge. RASV-immunized chickens showed significantly higher percentages of body weight gain at 10 days after challenge with *C. perfringens* compared to the average body weight gain for nonimmunized chickens (Table 3).

A subunit vaccine consisting of the C-terminal domain of alpha toxin (PlcC) protects mice against gas gangrene. However, no injectable PlcC subunit vaccine or live attenuated *S. enterica* serovar *Typhimurium*-delivered PlcC vaccine to induce protective immunity against *C. perfringens* type A strain-caused enteric disease has been evaluated before. The current study showed that an RASV expressing PlcC or an rPlcC subunit vaccine induced toxin-neutralizing antibodies and reduced intestinal lesion development and body weight loss in chickens challenged with virulent *C. perfringens*. Formerly, many investigators showed protection against NE by vaccination with a toxoid vaccine that consisted of an inactivated whole alpha toxin. The delivery of such a vaccine by repeated parenteral injections is not a feasible approach in commercial broilers and layers.

Figure 12:
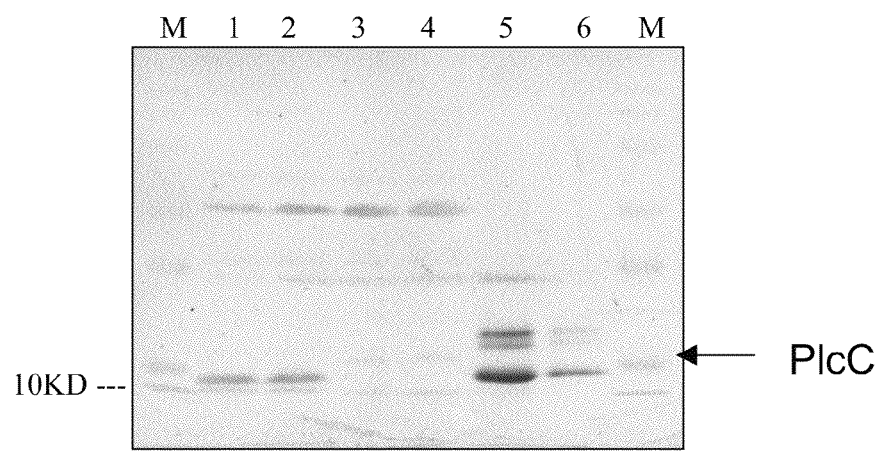

The expression of *C. perfringens* genes in *Salmonella* can be problematic and lead to strain instability due to the low G+C content in the DNA of *C. perfringens* (24-27%) compared to the G+C content of *Salmonella* (50-53%). In addition, the codon usage in *C. perfringens* is different from *Salmonella*, which can lead to poor expression due to the presence of codons in the coding sequences that are rare in highly expressed genes of *Salmonella*. We have optimized the sequence of plcC for codon usage and G+C content (FIG. 10). The G+C content was increased from 30% to 45%. We cloned this modified gene into Asd+ expression vector pYA4538 (FIG. 11B), fusing the optimized plcC gene to the dsbA signal sequence. The plasmid was moved into *Salmonella* vaccine strain χ9352 (Δpmi-2426 Δ(gmd-fcl)-26 ΔP$_{fur77}$::TT araC P$_{BAD}$ fur ΔP$_{crp527}$::TT araC P$_{BAD}$ crp ΔasdA21::TTaraC P$_{BAD}$ c2 ΔaraE25 ΔaraBAD23 ΔrelA198::araC P$_{BAD}$ lac/TT) and expression of the fusion protein was confirmed by western blot (FIG. 12). We are performing immunological evaluations using *Salmonella* vaccine strain χ9352 or χ9345 (Δpmi-2426 Δ(gmd-fcl)-26 ΔP$_{fur77}$::TT araC P$_{BAD}$ fur ΔP$_{crp527}$::TT araC P$_{BAD}$ crp ΔasdA18::TTaraC P$_{BAD}$ c2 ΔaraE25 ΔaraBAD23 ΔrelA198::araCP$_{BAD}$lacITT) carrying these plasmids.

Example 2

NetB Antigen Expressing Recombinant Bacteria

The netB gene encodes a protein that shows limited homology with *C. perfringens* β-toxin. It is found primarily in *C. perfringens* isolated from birds suffering from necrotic enteritis, but not from healthy animals. NetB is cytotoxic to chicken leghorn male hepatoma cells in vitro and it is required for the induction of necrotic enteritis symptoms in chickens. We have cloned the naturally occurring netB gene into a number of our Asd+ expression vectors and are performing immunological evaluations on *Salmonella* vaccine strains carrying these plasmids.

Figure 14:
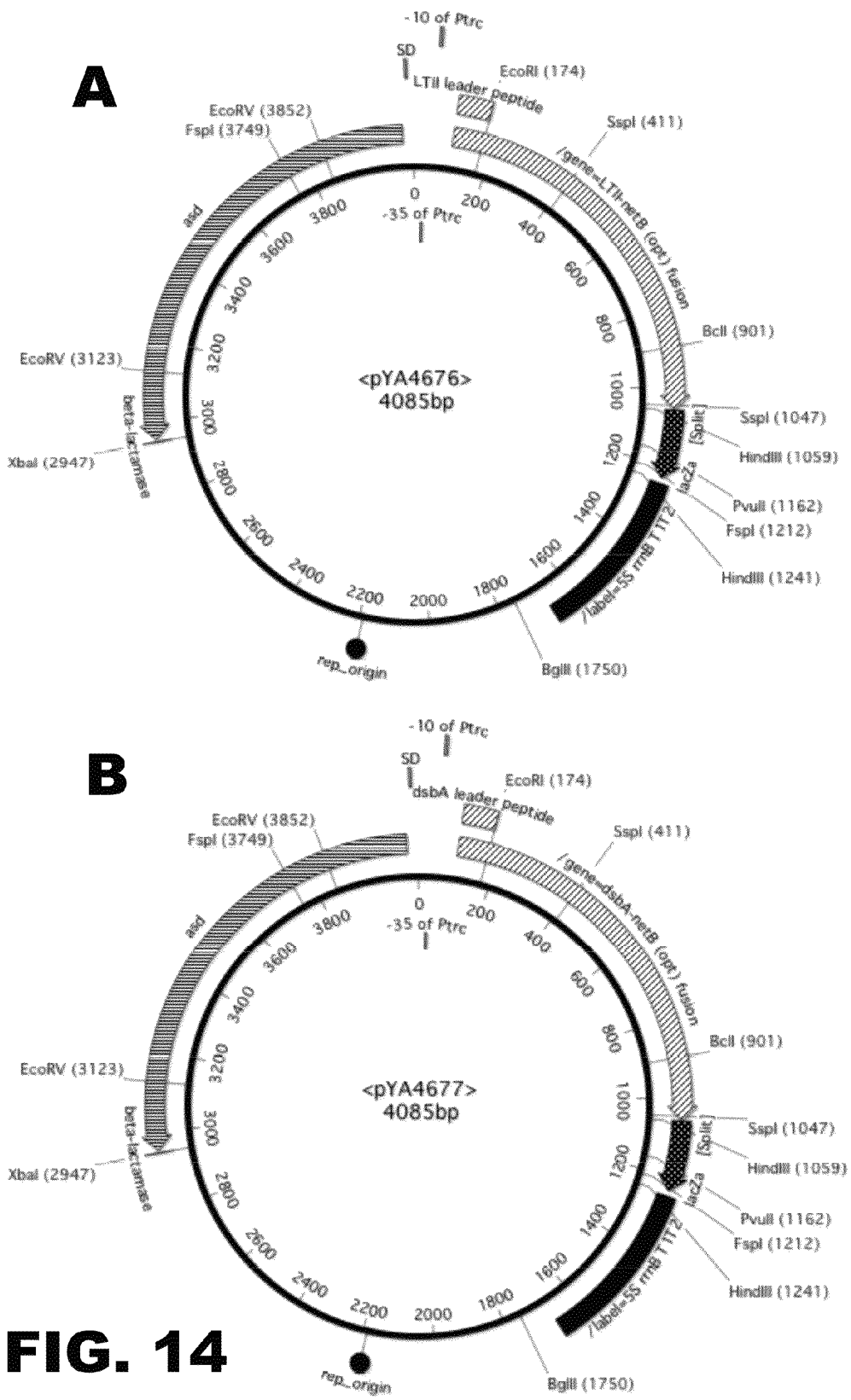
Figure 15:
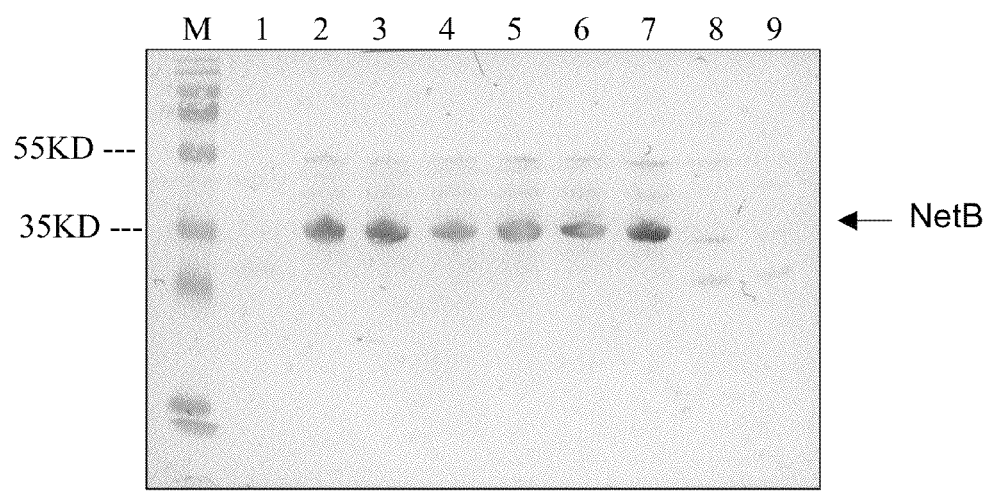

We have optimized the nucleic acid sequence of netB for codon usage and G+C content to allow optimal expression in *Salmonella* (FIG. 13). The G+C content in the optimized sequence was increased from 27% to 45%. The optimized nucleic acid sequence was cloned into Asd$^+$ gene expression vectors pYA4531 (FIG. 11A) and pYA4538 (FIG. 11B), fused to the signal sequences for eltII-B and dsbA, respectively, to yield plasmids pYA4676 (FIG. 14A) and pYA4677 (FIG. 14B). These plasmids were introduced into *Salmonella* vaccine strain χ9352 and expression of NetB was confirmed by western blot (FIG. 15). We are performing immunological evaluations. The optimized netB gene is being inserted into plasmid vectors pYA3493 and pYA3620.

Example 3

Additional Protective Antigens for Expression in Recombinant Attenuated *Salmonella* Vaccines Additional *C. perfringens* antigens that provide protection against necrotic enteritis when administered to chickens by injection into muscle tissue or when delivered by attenuated *Salmonella* include glyceraldehyde 3-phosphate dehydrogenase (GDP), pyruvate:ferredoxin oxidoreductase (PFOR), truncated pyruvate:ferredoxin oxidoreductase (tPFOR), fructose 1,6-biphosphate aldolase (FBA), a hypothetical protein (HP), and a truncated form of hypothetical protein (tHP). We have optimized the nucleic acid sequences for the genes encoding tPFOR (FIG. 16), tHP (FIG. 17), GDP (FIG. 18) or FBA (FIG. 19) for codon usage and G+C content for expression in *Salmonella*. The optimized genes are fused to a secretion signal such as bla SS, ompA SS, bla SS+CT, eltII-B SS or dsbA SS by cloning the optimized gene into AsdA+ expression plasmid pYA3493, pYA4101, pYA3620, pYA4531 or pYA4538, respectively and expressed in an attenuated *S. Typhimurium* strain such as χ9352.

Example 4

Expression of Two or More Antigens in a Single *Salmonella* Vaccine Strain

The incorporation of two or more antigens encoded by genes that have been optimized for G+C content and codon usage for expression in *Salmonella*, into the vaccine may provide enhanced protection against necrotic enteritis caused by *C. perfringens*. In one example, a bla SS-plcC fusion gene and a bla SS-netB fusion gene are cloned into the same Asd+ plasmid vector as an operon fusion. Expression is driven from a single, regulatable promoter, such as the P$_{trc}$ promoter. Both genes are expressed in the same attenuated Δasd *Salmonella* strain in amounts adequate to induce a protective immune response. In another example, each gene is transcribed from its own, regulatable promoter.

Figure 20:
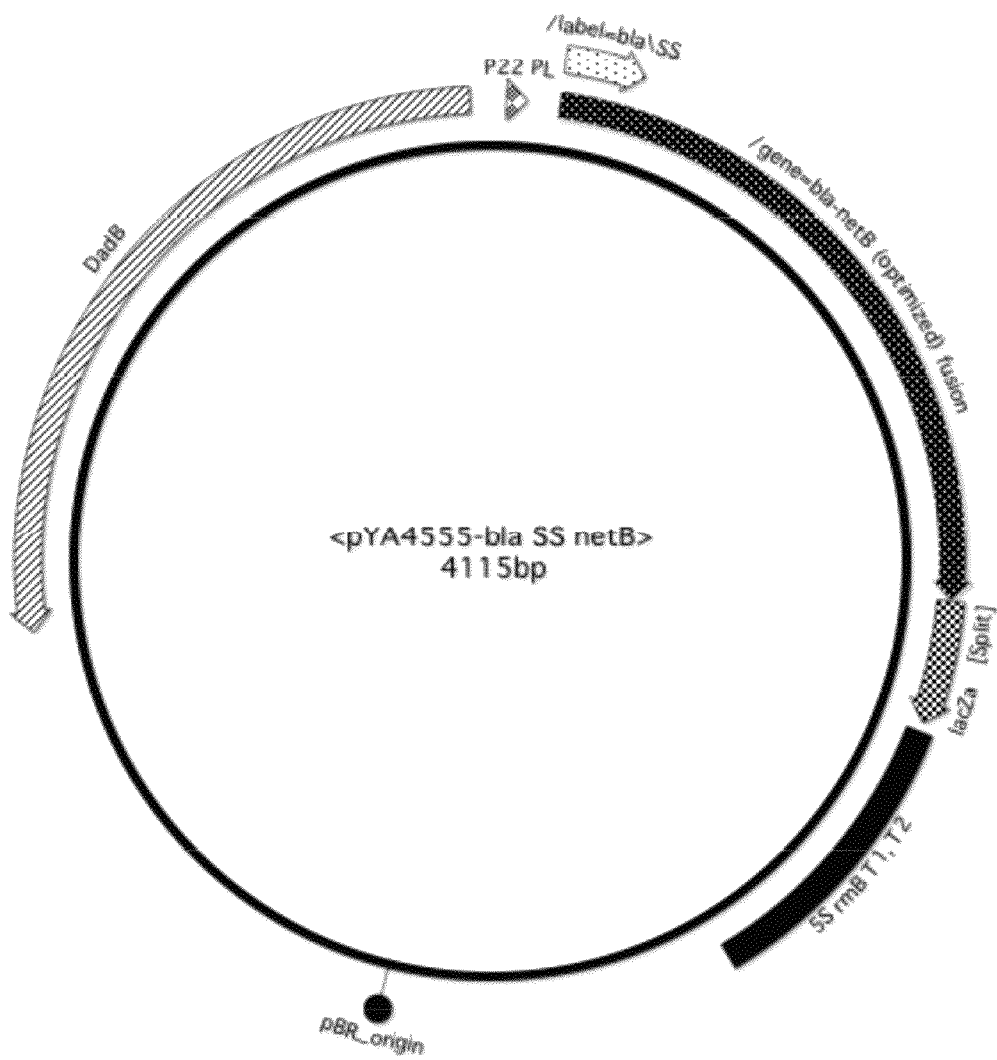
FIG. 20 depicts a diagram of vector pYA4555.
Figure 21:
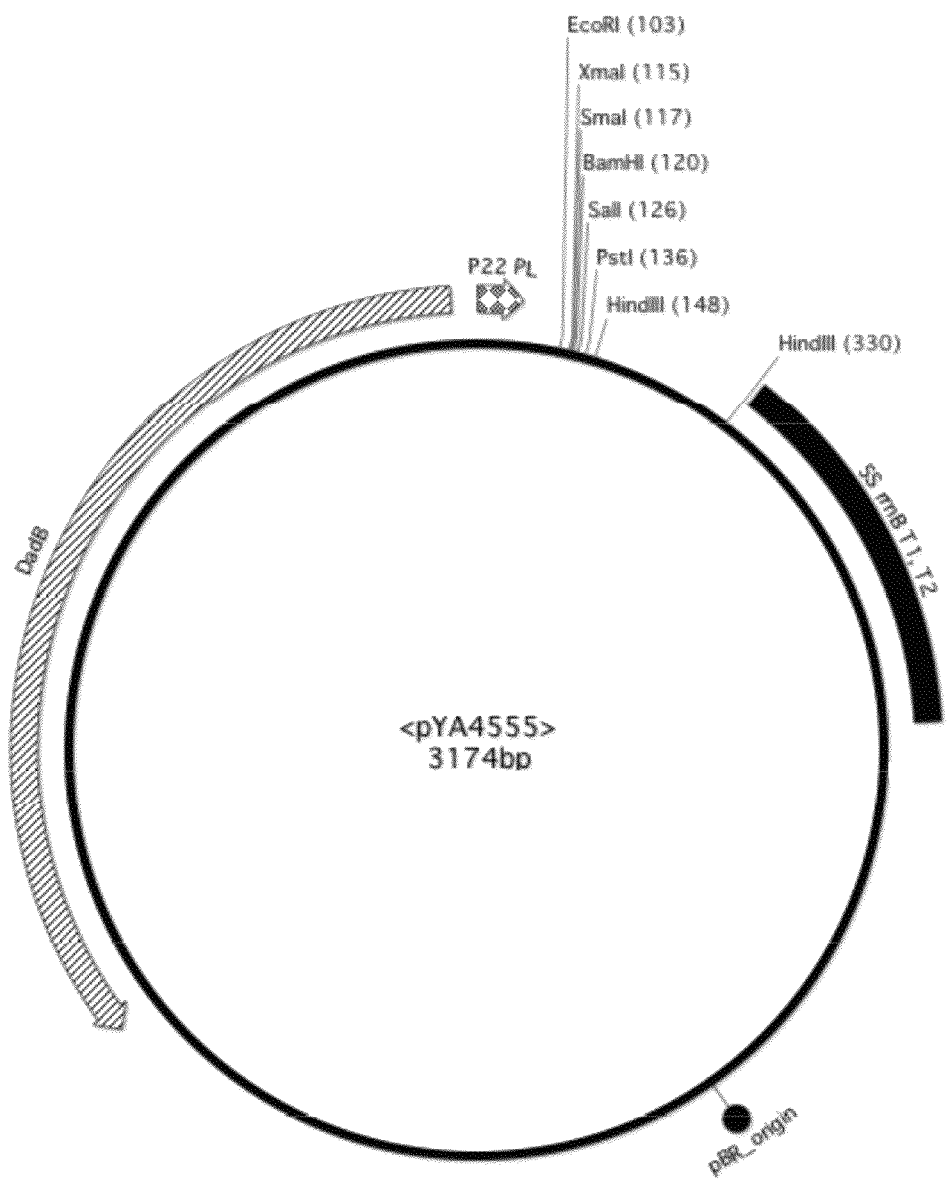
FIG. 21 depicts a diagram of vector pYA4555+bla SS netB (optimized).
Figure 22:
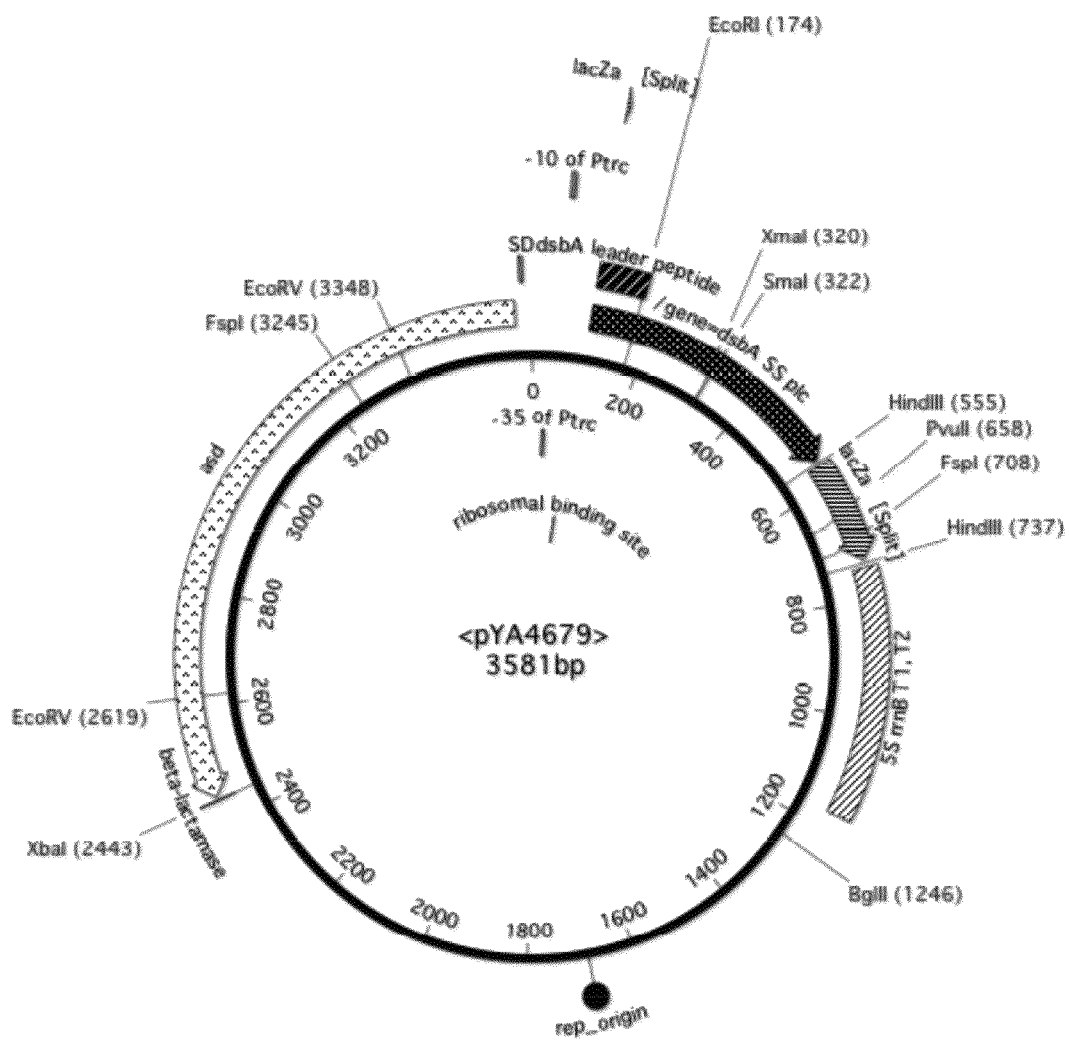
FIG. 22 depicts a diagram of vector pYA4679.

In another embodiment, each gene is cloned into a different expression plasmid, one with an Asd+ selectable marker and the other with a different selectable marker, such as DadB+. The bla SS netB (optimized) fusion protein is cloned into DadB+ expression vector pYA4555 (FIG. 20) to yield pYA4555+ bla SS netB (optimized) (FIG. 21). In this plasmid, the bla SS netB (optimized) gene is transcribed from the regulatable P22 P$_L$ promoter. Plasmid pYA4555+ bla SS netB (optimized) and plasmid pYA4679 (FIG. 22) are introduced into strain such as χ9590 (Δpmi-2426 Δ(gmd-fcl)-26 ΔP$_{fur81}$::TT araC P$_{BAD}$ fur ΔP$_{crp527}$::TT araC P$_{BAD}$ crp ΔasdA27::TT araC P$_{BAD}$ c2 ΔaraE25 ΔaraBAD23 ΔrelA198:: araC P$_{BAD}$ lacI TT ΔsopB1925 ΔagfBAC811 Δalr-3 ΔdadB4), which carries deletions in the asdA, alr-3 and dadB4 genes, allowing for selection of both AsdA+ plasmids and DadB+ plasmids. In addition, this strain produces both the C2 repressor and the LacI repressor, each transcribed from its own arabinose-regulated P$_{BAD}$ promoter, providing regulatable expression of netB from the P22 P$_L$ promoter (pYA4555+bla SS netB (optimized)) and plcC from the P$_{trc}$ promoter (pYA4679), respectively. Two antigens, PlcC and NetB are synthesized in a single bacterium in amounts adequate to induce an immune response against *C. perfringens*. Other attenuated *Salmonella* strains that can support the presence of two plasmids may also be used. Other plasmid selectable markers that are used include murA, aroA, aroC, aroD, ilvC or ilvE. Plasmids carrying these markers are maintained in strains carrying a deletion of the selectable marker gene.

We recently constructed derivatives of χ9590 with various types of rec mutations to investigate possible difficulties in the stable maintenance of two plasmids specifying two different protective antigens and with either the AsdA+ or DadB+ selective marker but with some DNA sequences in common due to using the same $P_{trc}$ promoter, termination sequence and pBR ori. Although we determined that recombination between plasmids as well as within plasmids was exceedingly rare (frequency of no more than $10^{-3}$ after full growth of a culture for some 30 generations), we found even greater stability in the χ9590 derivative strain χ9760 that has the ΔrecF126 allele in which recombination between plasmids was reduced another 10-fold. The inclusion of the ΔrecF126 deletion mutation in the wild-type S. Typhimurium UK-1 strain χ3761 has no effect on virulence having the same $LD_{50}$. We will therefore include the ΔrecF126 mutation in strains to maintain multiple plasmids specifying synthesis and delivery of multiple protective antigens from Clostridium perfringens.

In other embodiments, the genes for other protective antigens are codon-optimized and optimized for G+C content are used. The genes encoding tPFOR (FIG. 16), tHP (FIG. 17), GDP (FIG. 18) or FBA (FIG. 19) are cloned into separate plasmids or as operon fusions or as protein fusions and are expressed from one or more plasmids.

In another embodiment, one plasmid carries an operon fusion of two antigens, such as plcC and netB, and another plasmid directs the synthesis of a third antigen, such as tPFOR.

Example 5

Expression of One or More Antigens Host-Adapted Salmonella

Clostridium perfringens causes necrotizing enteritis in the small intestines of a variety of species, including cattle (Jejunal hemorrhagic syndrome, necrotic enteritis), swine and even humans, which occurs sporadically in underdeveloped countries. Some factors that predispose to C. perfringens induced necrotic enteritis include protozoan and helminth infections. C. perfringens type A, associated diarrhea is one of the top 5 causes of food borne bacterial diarrheal disease ranked by CDC in the U.S. α-toxin is particularly responsible for sublethal effects on enterocytes that could lead to malabsorption and stunting in children in developing countries. Studies also show the possible etiologic significance of early intestinal C. perfringens colonization and development of necrotizing enterocolitis in newborns. Therefore, it may be advantageous to formulate this vaccine for use in other species. Host-adapted Salmonella may be attenuated and further modified for this purpose as described above. Attenuated Salmonella Typhi and Salmonella Paratyphi A can be used as the antigen delivery vector for a human vaccine, attenuated Salmonella Choleraesuis can be used for a swine vaccine and attenuated Salmonella Dublin can be used for a bovine vaccine. In addition, attenuated Salmonella Gallinarum may be used for a poultry vaccine.

What is claimed is:

1. A recombinant attenuated *Salmonella enterica* bacterium, wherein the bacterium is capable of expression of one nucleic acid encoding at least two protein antigens of *Clostridium perfringens*, or wherein the bacterium is capable of expression of more than one nucleic acid, each encoding a *Clostridium perfringens* protein antigen, wherein the C. perfringens protein antigen(s) are selected from PlcC (C-terminal domain of C. perfringens alpha toxin), NetB, GDP (glyceraldehyde 3-phosphate dehydrogenase), PFOR (pyruvate:ferredoxin oxidoreductase), FBA (fructose 1,6-biphosphate aldolase), HP (a C. perfringens hypothetical protein), and a fragment thereof that is capable of eliciting an immune response, wherein the bacterium upon administration to a mammal or a bird, elicits an immune response against C. perfringens in the mammal or the bird.

2. The recombinant attenuated *Salmonella enterica* bacterium of claim 1, wherein the bacterium is capable of colonizing the gut of the mammal or the bird upon oral administration.

3. The recombinant attenuated *Salmonella enterica* bacterium of claim 1, wherein the bacterium further comprises the □pmi-2426 mutation and is capable of eliciting an immune response against at least two *Salmonella enterica* serotypes.

4. The recombinant attenuated *Salmonella enterica* bacterium of claim 1, wherein the codons of the nucleic acid encoding the antigen(s) have been modified so as to optimize the expression level of the antigen(s).

5. A vaccine composition comprising the recombinant attenuated *Salmonella enterica* bacterium of claim 1.

6. A method of inducing an immune response against *Clostridium perfringens*, the method comprising administering the vaccine composition of claim 5 to a mammal or a bird.

7. The method of claim 6, wherein the recombinant attenuated *Salmonella enterica* bacterium is *Salmonella enterica* serovar *Typhimurium* and the bird is a commercial poultry bird.

8. A recombinant attenuated *Salmonella enterica* bacterium, wherein the bacterium is capable of expression of one nucleic acid encoding at least three protein antigens of *Clostridium perfringens*, or wherein the bacterium is capable of expression of more than two nucleic acids, each encoding a *Clostridium perfringens* protein antigen, wherein the *C. perfringens* protein antigen(s) are selected from PlcC (C-terminal domain of *C. perfringens* alpha toxin), NetB, GDP (glyceraldehyde 3-phosphate dehydrogenase), PFOR (pyruvate:ferredoxin oxidoreductase), FBA (fructose 1,6-biphosphate aldolase), HP (a *C. perfringens* hypothetical protein), and a fragment thereof that is capable of eliciting an immune response, wherein the bacterium upon administration to a mammal or a bird, elicits an immune response against *C. perfringens* in the mammal or the bird.

9. A recombinant attenuated *Salmonella enterica* bacterium, wherein the bacterium is capable of expression of one or more than one nucleic acid, which encodes at least three protein antigens of *Clostridium perfringens*, wherein the protein antigens are PlcC (C-terminal domain of *C. perfringens* alpha toxin), NetB, and FBA (fructose 1,6-biphosphate aldolase) and wherein the bacterium upon administration to a mammal or a bird, elicits an immune response against *C. perfringens* in the mammal or the bird.

* * * * *

UNITED STATES PATENT AND TRADEMARK OFFICE
CERTIFICATE OF CORRECTION

PATENT NO.        : 9,040,059 B2
APPLICATION NO.   : 12/681711
DATED             : May 26, 2015
INVENTOR(S)       : Roy Curtiss, III et al.

It is certified that error appears in the above-identified patent and that said Letters Patent is hereby corrected as shown below:

In the Claims:

In claim 3 (column 71, line 7), delete "☐pmi-2426 mutation" and replace with --Δpmi-2426 mutation--

Signed and Sealed this
Sixteenth Day of August, 2016

Michelle K. Lee
*Director of the United States Patent and Trademark Office*